United States Patent

Chabert et al.

[11] Patent Number: 5,939,411
[45] Date of Patent: Aug. 17, 1999

[54] PIPERIDINE DERIVATIVES PROCESS FOR OBTAINING THEM AND PHARMACEUTICAL COMPOSITIONS CONTAINING THEM

[75] Inventors: Nathalie Chabert, Cournonterral; Jean-Philippe Ducoux, Montpellier; Xavier Emonds-Alt, Combaillaux; Patrick Gueule, Teyran; Vincenzo Proietto, Saint Georges D'Orques; Didier Van Broeck, Murviel Les Montpellier, all of France

[73] Assignee: Sanofi, Paris, France

[21] Appl. No.: 08/916,952

[22] Filed: Aug. 25, 1997

Related U.S. Application Data

[62] Division of application No. 08/703,952, Aug. 28, 1996.

[30] Foreign Application Priority Data

Aug. 28, 1995 [FR] France .................................. 95 10142

[51] Int. Cl.⁶ ........................ A61K 31/445; A61K 31/55; C07D 211/32; C07D 409/00
[52] U.S. Cl. ........................... 514/212; 514/316; 514/317; 514/318; 514/326; 514/327; 514/329; 514/330; 546/187; 546/188; 546/189; 546/190; 546/191; 540/531

[58] Field of Search ..................... 546/187, 188, 546/189, 190, 191; 514/316, 317, 318, 326, 327, 329, 330, 212; 540/531

[56] References Cited

U.S. PATENT DOCUMENTS 5,635,510  6/1997  Burkholder et al. ............... 514/278
5,830,906  11/1998  Chabert et al. .................... 514/329

*Primary Examiner*—Mukund J. Shah
*Assistant Examiner*—Bruck Kifle
*Attorney, Agent, or Firm*—Bacon & Thomas

[57] ABSTRACT

Piperidine derivatives, process for obtaining them and pharmaceutical compositions containing them, of formula

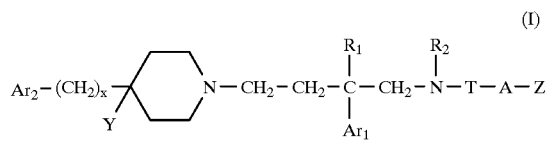

used as neurokinin receptor antagonists, which are, in particular, useful for the treatment of all substance P- and neurokinin-dependent pathologies.

21 Claims, No Drawings

PIPERIDINE DERIVATIVES PROCESS FOR OBTAINING THEM AND PHARMACEUTICAL COMPOSITIONS CONTAINING THEM

This application is a Division of application Ser. No. 08/703,952, filed Aug. 28, 1996, currently pending.

The present invention relates to new piperidine derivatives, to a process for preparing them and to pharmaceutical compositions containing them as active principle.

More especially, the present invention relates to a new class of piperidine derivatives for therapeutic use in the pathological phenomena which involve the tachykinin system, such as, for example, without limitation and not exclusively: pain (D. Regoli et al., Life Sciences, 1987, 40, 109–117), allergy and inflammation (J. E. Morlay et al., Life Sciences, 1987, 41, 527–544), circulatory insufficiency (J. Losay et al., 1977, Substance P, Von Euler, U. S. and Pernow ed. 287–293, Raven Press, New York), gastrointestinal disorders (D. Regoli et al., Trends Pharmacol, Sci., 1985, 6, 481–484), respiratory disorders (J. Mizrahi et al., Pharmacology, 1982, 25, 39–50), neurological disorders and neuropsychiatric disorders (C. A. Maggi et al., J. Autonomic Pharmacol., 1993, 13, 23–93).

In recent years, a large amount of research work has been performed on tachykinins and their receptors. Tachykinins are distributed both in the central nervous system and in the peripheral nervous system. The tachykinin receptors have been recognized and have been classified in three types: $NK_1$, $NK_2$, $NK_3$. Substance P (SP) is the endogenous ligand for the $NK_1$ receptors, neurokinin A ($NK_A$) that for the $NK_2$ receptors and neurokinin B ($NK_B$) that for the $NK_3$ receptors.

$NK_1$, $NK_2$ and $NK_3$ receptors have been demonstrated in various species.

A recent review by C.A. Maggi et al. surveys the tachykinin receptors and their antagonists and describes the pharmacological studies and applications in human therapy (J. Autonomic Pharmacol., 1993, 13, 23–93).

Among specific antagonists for the $NK_1$ receptor, the following non-peptide compounds may be mentioned: CP-96345 (J. Med. Chem., 1992, 35, 2591–2600), RP-68651 (Proc. Natl. Acad. Sci. USA, 1991, 88, 10208–10212), SR 140333 (Curr. J. Pharmacol., 1993, 250, 403–413).

For the $NK_2$ receptor, a non-peptide selective antagonist, SR 48968, has been described in detail (Life Sci., 1992, 50, PL101–PL106).

As regards the $NK_3$ receptor, some non-peptide compounds have been described as having an affinity for the $NK_3$ receptor of rat and guinea pig brain (FASEB J., 1993, 7 (4), A710, 4104); a peptide antagonist [$Trp^7,\beta Ala^8$]$NK_A$, weakly specific for the $NK_3$ receptor of rat brain, has also been described (J. Autonomic Pharmacol., 1993, 13, 23–93).

Patent Application EP-A-336230 describes peptide derivatives which are substance P and neurokinin A antagonists and are useful for the treatment and prevention of asthma.

International Patent Applications WO 90/05525, WO 90/05729, WO 91/09844 and WO 91/18899 and European Patent Applications EP-A-0436334, EP-A-0429466 and EP-A-0430771 describe substance P antagonists.

European Patent Applications EP-A-0428434, EP-A-0515240, EP-A-0559538, EP-A-591040, EP-A-0625509, EP-A-0630887 and International Patent Applications WO 94/10146, WO 94/29309, WO 94/26735, wo 95/05377, WO 95/12577 and WO 95/16682 describe neurokinin receptor antagonists.

Patent Appliction EP-A-0474561 relates to ompounds of formula:

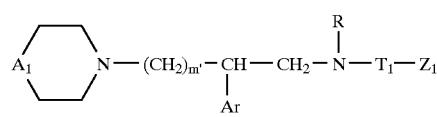

in which, in particular,
m' is two or three;
R represents hydrogen or a ($C_1$–$C_6$)alkyl;
$A_1$ can represent a group:

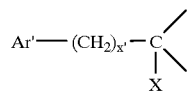

in which:
Ar' represents an unsubstituted or substituted phenyl; a pyridyl; a thienyl;
x' is zero or one;
x represents a hydroxyl; a ($C_1$–$C_4$)alkoxy; a ($C_1$–$C_3$) alkyl-OH; a ($C_1$–$C_4$)acyloxy; a phenacyloxy; a carboxyl; a ($C_1$–$C_4$) alkoxycarbonyl; a cyano; an amino-($C_1$–$C_3$)alkylene; a group —$N(X_1)_2$ in which the groups $X_1$ independently represent hydrogen, a ($C_1$–$C_4$)alkyl; a group —NHCO—($C_1$–$C_6$)alkyl; a group —($C_1$–$C_3$)alkylene-NHCO-($C_1$–$C_3$)alkyl; a ($C_1$–$C_4$)acyl; a group —S—$X_2$ in which $X_2$ represents hydrogen or a ($C_1$–$C_4$)alkyl.

Patent Application EP-A-0512901 relates to compounds of formula:

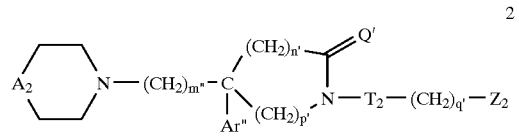

in which, in particular:
m" is two or three;
Q' represents an oxygen atom or two hydrogen atoms;
$A_2$ can represent a group:

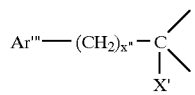

in which:
Ar''' represents an unsubstituted or substituted phenyl; a pyridyl; a thienyl;
x" is zero or one;
X' represents a hydrogen; a hydroxyl; a ($C_1$–$C_4$)alkoxy; a carboxyl; a ($C_1$–$C_4$)alkoxycarbonyl; a cyano; a group —N(X'₁)₂ in which the groups X'₁ independently represent hydrogen, a (C₁–C₄)alkyl, a hydroxy-(C₁–C₄) alkyl, a (C₁–C₄)acyl, or alternatively —(X'₁)₂, with the nitrogen atom to which it is linked, constitutes a heterocycle chosen from pyrrolidine, piperidine and morpholine; a group —S—X'₂ in which X'₂ represents hydrogen or a (C₁–C₄)alkyl group.

It has now been found that new piperidine derivatives possess advantageous pharmacological properties as neurokinin receptor antagonists, and are, in particular, useful for the treatment of all substance P- and neurokinin-dependent pathologies.

Furthermore, it has been found that these new piperidine derivatives which are substitued at position 4 with new functions other than those described previously for the compounds of formula 1 or the compounds of formula 2 possess a very high affinity for the neurokinin receptors.

Thus, according to one of its aspects, the present invention relates to compounds of formula:

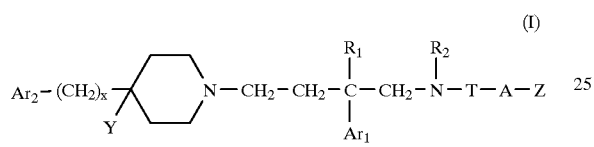

(I)

in which:
x is zero or one;
R₁ represents hydrogen;
R₂ represents a hydrogen or a (C₁–C₇)alkyl;
or alternatively R₁ and R₂ together constitute a group —(CH₂)ₙCQ— in which Q represents an oxygen atom or two hydrogen atoms and n is one, two or three;
Y represents a group chosen from:
Y₁) (C₁–C₇)alkyl;
Y₂) —(CH₂)ₚ—OR₃;
Y₃) —O—CH₂CH₂—OR₄;
Y₄) —OCOR₅;
Y₅) —(CH₂)ₚ—OCOR₆;
Y₆) —(CH₂)q—OCONH—(C₁–C₇) alkyl;
Y₇) —NR₇R₈;
Y₈) —(CH₂)ₚ—NR₉R₁₀;
Y₉) —NR₁₁C (=W₁) R₁₂;
Y₁₀) —(CH₂)ₚ—NR₁₃C (=W₁) R₁₄;
Y₁₁) —(CH₂)q—NR₁₃COOR₁₅;
Y₁₂) —(CH₂)q—NR₁₃SO₂R₁₆;
Y₁₃) —(CH₂)q—NR₁₃C (=W₁) NR₁₇R₁₈;
Y₁₄) —C(=W₁) NR₁₉R₂₀;
Y₁₅) —CH₂—COOR₂₁;
Y₁₆) —CH₂—C(=W₁) NR₁₇R₁₈;

Y₁₇) 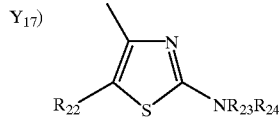

Y₁₈) 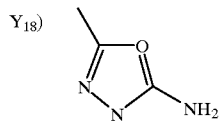

Y₁₉) —CO—NR₂₅—NR₂₆R₂₇;

Y₂₀) —NR₂₅COCOR₂₉;

Y₂₁) 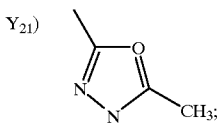

in which groups:
p is one or two;
q is zero, one or two;
W₁ represents an oxygen atom or a sulphur atom;
R₃ represents a (C₁–C₇)alkyl; R₃ can, in addition, represent hydrogen when R₁ and R₂ together constitute a group —(CH₂)ₙ—CQ—;
R₄ represents a hydrogen; (C₁–C₇)alkyl; a formyl; a (C₁–C₇) alkylcarbonyl;
R₅ represents a pyridyl or a (C₃–C₇)cycloalkyl unsubstituted or substituted with one or more methyls; R₅ can, in addition, represent a phenyl when R₁ and R₂ together constitute a group —(CH₂)ₙ—CQ—;
R₆ represents hydrogen; a (C₁–C₇)alkyl; a (C₃–C₇) cycloalkyl unsubstituted or substituted with one or more methyls; a phenyl; a pyridyl;
R₇ represents a hydrogen or a (C₁–C₇)alkyl;
R₈ represents a (C₃–C₇)cycloalkylmethyl; a benzyl;
or alternately R₇ and R₈, together with the nitrogen atom to which they are linked, constitute a heterocycle chosen from: azetidine, thiomorpholine, perhydroazepine, piperazine unsubstituted or substituted at position 4 with a (C₁–C₄)alkyl; R₇ and R₈, together with the nitrogen atom to which they are linked, can, in addition, constitute a heterocycle chosen from pyrrolidine, piperidine and morpholine when R₁ represents hydrogen;
R₉ represents a hydrogen or a (C₁–C₇)alkyl;
R₁₀ represents a (C₁–C₇)alkyl; a (C₃–C₇) cycloalkylmethyl; a benzyl; R₁₀ can, in addition, represent hydrogen when R₁ and R₂ together constitute a group —(CH₂)ₙ—CQ—;
R₁₁ represents a hydrogen or a (C₁–C₇)alkyl;
R₁₂ represents a (C₃–C₇)cycloalkyl unsubstituted or substituted with one or more methyls; a phenyl; a benzyl; a vinyl; a pyridyl; a furyl; a thienyl; a pyrrolyl; an imidazolyl; R₁₂ can, in addition, represent hydrogen when R₁ represents hydrogen; R₁₂ can, in addition, represent a (C₁–C₇)alkyl when both R₁₁ represents a (C₁–C₇)alkyl and R₁ represents hydrogen;
or alternatively R₁₁ and R₁₂ together represent a group —(CH₂)ₘ— in which m is three or four;
R₁₃ represents a hydrogen or a (C₁–C₇) alkyl;
R₁₄ represents a hydrogen; a (C₃–C₇) cycloalkyl unsubstituted or substituted with one or more methyls; a phenyl, a benzyl, a vinyl; a pyridyl; a furyl; a thienyl; a pyrrolyl; an imidazolyl; R₁₄ can, in addition, represent a (C₁–C₇)alkyl when R₁ and R₂ together constitute a group —(CH₂)ₙ—CQ—; R₁₄ can, in addition, represent a (C₁–C₇)alkyl when both R₁₃ represents a (C₁–C₇)alkyl and R₁ represents hydrogen;
R₁₅ represents a (C₁–C₇) alkyl or a phenyl;
R₁₆ represents a (C₁–C₇)alkyl; an amino, free or substituted with one or two (C₁–C₇)alkyls; a phenyl unsubstituted or substituted one or more times with a substituent chosen from: a halogen atom, a $(C_1-C_7)$alkyl, a trifluoromethyl, a hydroxyl, a $(C_1-C_7)$alkoxy, a carboxyl, a $(C_1-C_7)$alkoxycarbonyl, a $(C_1-C_7)$ alkylcarbonyloxy, a cyano, a nitro, an amino, free or substituted with one or two $(C_1-C_7)$alkyls, the said substituents being identical or different;

$R_{17}$ and $R_{18}$ each independently represent a hydrogen or a $(C_1-C_7)$alkyl; $R_{18}$ can, in addition, represent a $(C_3-C_7)$ cycloalkyl, a $(C_3-C_7)$ cycloalkylmethyl, a hydroxyl, a $(C_1-C_4)$alkoxy, a benzyl or a phenyl;

or alternatively $R_{17}$ and $R_{18}$, together with the nitrogen atom to which they are linked, constitute a heterocycle chosen from azetidine, pyrrolidine, piperidine, morpholine, thiomorpholine, perhydroazepine and piperazine unsubstituted or substituted at position 4 with a $(C_1-C_4)$ alkyl;

$R_{19}$ represents a hydrogen or a $(C_1-C_7)$alkyl;

$R_{20}$ represents a $(C_3-C_7)$ cycloalkyl; a $(C_3-C_7)$ cycloalkylmethyl; a hydroxyl; a $(C_1-C_4)$alkoxy; a benzyl; a phenyl; $R_{20}$ can, in addition, represent a hydrogen or a $(C_1-C_7)$alkyl when $R_1$ represents hydrogen or when $R_1$ and $R_2$ together constitute a group —$(CH_2)_n$—CQ— in which n is two or three;

or alternatively $R_{19}$ and $R_{20}$, together with the nitrogen atom to which they are linked, constitute a heterocycle chosen from azetidine, thiomorpholine, perhydroazepine, piperazine and isoxazolidine; $R_{19}$ and $R_{20}$, together with the nitrogen atom to which they are linked, can, in addition, constitute a heterocycle chosen from pyrrolidine, piperidine, morpholine and piperazine substituted at position 4 with a $(C_1-C_4)$alkyl when $R_1$ represents hydrogen or when $R_1$ and $R_2$ together constitute a group $(CH_2)_n$—CQ— in which n is two or three;

$R_{21}$ represents a hydrogen or a $(C_1-C_7)$alkyl;

$R_{22}$ represents a hydrogen or a $(C_1-C_7)$alkyl;

$R_{23}$ and $R_{24}$ each independently represent a hydrogen or a $(C_1-C_7)$alkyl; $R_{24}$ can, in addition, represent a formyl or a $(C_1-C_7)$alkylcarbonyl;

$R_{25}$ represents a hydrogen or a $(C_1-C_7)$alkyl;

$R_{26}$ and $R_{27}$ each independently represent a hydrogen or a $(C_1-C_7)$alkyl; $R_{27}$ can, in addition, represent a $(C_1-C_7)$ alkylcarbonyl;

or alternatively $R_{26}$ and $R_{27}$, together with the nitrogen atom to which they are linked, constitute a heterocycle chosen from azetidine, pyrrolidine, piperidine, morpholine, thiomorpholine or perhydroazepine;

$R_{29}$ represents a $(C_1-C_4)$alkoxy;

$Ar_1$ represents a phenyl unsubstituted or substituted one or more times with a substituent chosen from: a halogen atom, a hydroxyl, a $(C_1-C_4)$alkoxy, a $(C_1-C_4)$alkyl, a trifluoromethyl, a methylenedioxy, the said substituents being identical or different; a thienyl unsubstituted or substituted with a halogen atom; a benzothienyl unsubstituted or substituted with a halogen atom; a naphthyl unsubstituted or substituted with a halogen atom; an indolyl unsubstituted or N-substituted with a $(C_1-C_4)$alkyl or a benzyl; an imidazolyl unsubstituted or substituted with a halogen atom; a pyridyl unsubstituted or substituted with a halogen atom; a biphenyl;

$Ar_2$ represents a phenyl unsubstituted or substituted one or more times with a substituent chosen from: a halogen atom, a hydroxyl, a $(C_1-C_4)$alkoxy, a $(C_1-C_4)$alkyl, a trifluoromethyl, a methylenedioxy, the said substituents being identical or different; a pyridyl; a thienyl, a pyrimidinyl; an imidazolyl unsubstituted or substituted with a $(C_1-C_4)$alkyl;

T represents a —$CH_2$— group; a —CO— group; a —COO— group; a group —$CONR_{28}$— in which $R_{28}$ represents a hydrogen or a $(C_1-C_4)$alkyl; on the condition that T represents a —$CH_2$— group when Q represents an oxygen atom and T represents one of the groups —CO—, —COO— or —$CONR_{28}$— when Q represents two hydrogen atoms;

A represents a direct bond or a group —$(CH_2)_t$— in which t is one, two or three;

Z represents an optionally substituted mono-, di- or tricyclic aromatic or heteroaromatic group; as well as their possible salts with inorganic or organic acids.

The compounds of formula (I) according to the invention comprise both the optically pure isomers and the racemates.

Salts of the compounds of formula (I) may be formed. These salts comprise both those with inorganic or organic acids which permit an appropriate separation or crystallization of the compounds of formula (I), such as picric acid or oxalic acid or an optically active acid, for example a mandelic or camphorsulphonic acid, and those which form pharmaceutically acceptable salts such as the hydrochloride, hydrobromide, sulphate, hydrogen sulphate, dihydrogen phosphate, methanesulphonate, methyl sulphate, maleate, fumarate, 2-naphthalenesulphonate, gluconate, citrate, isethionate, benzenesulphonate and paratoluenesulphonate.

Depending on the meaning of $R_1$ and $R_2$, the compounds of the invention belong to one of the families described below, of formula (Ia), (Ib) or (Ic).

The family (Ia) consists of the compounds of formula:

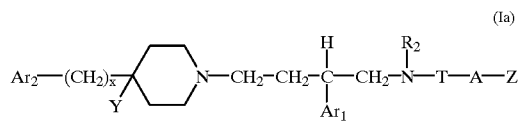

(Ia)

in which:

x, $Ar_1$, $Ar_2$, T, A and Z have the meanings given above for (I);

$R_2$ represents a hydrogen or a $(C_1-C_7)$alkyl;

Y represents a group chosen from:

$Y_1$) $(C_1-C_7)$alkyl;
$Y_2$) —$(CH_2)_p$—$OR_3$;
$Y_3$) —O—$CH_2CH_2$—$OR_4$;
$Y_4$) —$OCOR_5$;
$Y_5$) —$(CH_2)_p$—$OCOR_6$;
$Y_6$) —$(CH_2)_q$—OCONH—$(C_1-C_7)$alkyl;
$Y_7$) —$NR_7R_8$;
$Y_8$) —$(CH_2)_p$—$NR_9R_{10}$;
$Y_9$) —$NR_{11}C$ (=$W_1$) $R_{12}$;
$Y_{10}$) —$(CH_2)_p$—$NR_{13}C$ (=$W_1$) $R_{14}$;
$Y_{11}$) —$(CH_2)_q$—$NR_{13}COOR_{15}$;
$Y_{12}$) —$(CH_2)_q$—$NR_{13}SO_2R_{16}$;
$Y_{13}$) —$(CH_2)_q$—$NR_{13}C$ (=$W_1$) $NR_{17}R_{18}$;
$Y_{14}$) —C(=$W_1$)$NR_{19}R_{20}$;

$Y_{15}$) —$CH_2$—$COOR_{21}$;
$Y_{16}$) —$CH_2$—$C(=W_1)$ $NR_{17}R_{18}$;

$Y_{17}$) 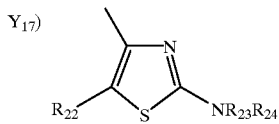

$Y_{18}$) 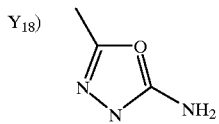

$Y_{19}$) 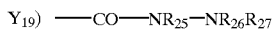 —CO—$NR_{25}$—$NR_{26}R_{27}$ $Y_{20}$)  —$NR_{25}COCOR_{29}$;

$Y_{21}$) 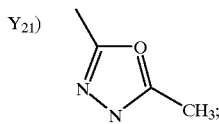

in which groups:
p is one or two;
q is zero, one or two;
$W_1$ represents an oxygen atom or a sulphur atom;
$R_3$ represents a $(C_1-C_7)$alkyl;
$R_4$ represents a hydrogen; a $(C_1-C_7)$alkyl; a formyl; a $(C_1-C_7)$ alkylcarbonyl;
$R_5$ represents a pyridyl or a $(C_3-C_7)$cycloalkyl unsubstituted or substituted with one or more methyls;
$R_6$ represents hydrogen; a $(C_1-C_7)$alkyl; a $(C_3-C_7)$ cycloalkyl unsubstituted or substituted with one or more methyls; a phenyl; a pyridyl;
$R_7$ represents a hydrogen or a $(C_1-C_7)$alkyl;
$R_8$ represents a $(C_3-C_7)$cycloalkylmethyl; a benzyl;
or alternately $R_7$ and $R_8$, together with the nitrogen atom to which they are linked, constitute a heterocycle chosen from: azetidine, thiomorpholine, perhydroazepine, piperazine unsubstituted or substituted at position 4 with a $(C_1-C_4)$alkyl, pyrrolidine, piperidine or morpholine;
$R_9$ represents a hydrogen or a $(C_1-C_7)$alkyl;
$R_{10}$ represents a $(C_1-C_7)$ alkyl; a $(C_3-C_7)$ cycloalkylmethyl; a benzyl;
$R_{11}$ represents a hydrogen or a $(C_1-C_7)$alkyl;
$R_{12}$ represents a $(C_3-C_7)$cycloalkyl unsubstituted or substituted with one or more methyls; a phenyl; a benzyl; a vinyl; a pyridyl; a furyl; a thienyl; a pyrrolyl; an imidazolyl; a hydrogen; $R_{12}$ can, in addition, represent a $(C_1-C_7)$alkyl when $R_{11}$ represents a $(C_1-C_7)$alkyl;
or alternatively $R_{11}$ and $R_{12}$ together represent a group —$(CH_2)_m$— in which m is three or four;
$R_{13}$ represents a hydrogen or a $(C_1-C_7)$alkyl;
$R_{14}$ represents a hydrogen; a $(C_3-C_7)$ cycloalkyl unsubstituted or substituted with one or more methyls; a phenyl; a benzyl; a vinyl; a pyridyl; a furyl; a thienyl; a pyrrolyl; an imidazolyl; $R_{14}$ can, in addition, represent a $(C_1-C_7)$alkyl when $R_{13}$ represents a $(C_1-C_7)$ alkyl;
$R_{15}$ represents a $(C_1-C_7)$alkyl or a phenyl;
$R_{16}$ represents a $(C_1-C_7)$alkyl; an amino, free or substituted with one or two $(C_1-C_7)$alkyls; a phenyl unsubstituted or substituted one or more times with a substituent chosen from: a halogen atom, a $(C_1-C_7)$alkyl, a trifluoromethyl, a hydroxyl, a $(C_1-C_7)$alkoxy, a carboxyl, a $(C_1-C_7)$alkoxycarbonyl, a $(C_1-C_7)$ alkylcarbonyloxy, a cyano, a nitro, an amino, free or substituted with one or two $(C_1-C_7)$alkyls, the said substituents being identical or different;

$R_{14}$ and $R_{18}$ each independently represent a hydrogen or a $(C_1-C_7)$alkyl; $R_{18}$ can, in addition, represent a $(C_3-C_7)$ cycloalkyl, a $(C_3-C_7)$ cycloalkylmethyl, a hydroxyl, a $(C_1-C_4)$alkoxy, a benzyl or a phenyl;

or alternatively $R_{17}$ and $R_{18}$, together with the nitrogen atom to which they are linked, constitute a heterocycle chosen from azetidine, pyrrolidine, piperidine, morpholine, thiomorpholine, perhydroazepine and piperazine unsubstituted or substituted at position 4 with a $(C_1-C_4)$alkyl;

$R_{19}$ represents a hydrogen or a $(C_1-C_7)$alkyl;

$R_{20}$ represents a $(C_3-C_7)$ cycloalkyl; a $(C_3-C_7)$ cycloalkylmethyl; a hydroxyl; a $(C_1-C_4)$ alkoxy; a benzyl; a phenyl; a hydrogen; a $(C_1-C_7)$alkyl;

or alternatively $R_{19}$ and $R_{20}$, together with the nitrogen atom to which they are linked, constitute a heterocycle chosen from: azetidine, thiomorpholine, perhydroazepine, piperazine, isoxazolidine, pyrrolidine, piperidine, morpholine and piperazine substituted at position 4 with a $(C_1-C_4)$alkyl;

$R_{21}$ represents a hydrogen or a $(C_1-C_7)$alkyl;

$R_{22}$ represents a hydrogen or a $(C_1-C_7)$alkyl;

$R_{23}$ and $R_{24}$ each independently represent a hydrogen or a $(C_1-C_7)$alkyl; $R_{24}$ can, in addition, represent a formyl or a $(C_1-C_7)$alkylcarbonyl;

$R_{25}$ represents a hydrogen or a $(C_1-C_7)$alkyl;

$R_{26}$ and $R_{27}$ each independently represent a hydrogen or a $(C_1-C_7)$alkyl; $R_{27}$ can, in addition, represent a $(C_1-C_7)$ alkylcarbonyl;

or alternatively $R_{26}$ and $R_{27}$, together with the nitrogen atom to which they are linked, constitute a heterocycle chosen from azetidine, pyrrolidine, piperidine, morpholine, thiomorpholine and perhydroazepine;

$R_{29}$ represents a $(C_1-C_4)$alkoxy; as well as their possible salts with inorganic or organic acids.

The family (Ib) consists of the compounds of formula:

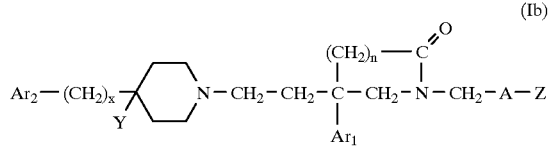

(Ib)

in which
x, $Ar_1$, $Ar_2$, n, A and Z have the meanings given above for (I);
Y represents a group chosen from:
$Y_1$) $(C_1-C_7)$alkyl;
$Y_2$) —$(CH_2)_p$—$OR_3$;
$Y_3$) —O—$CH_2CH_2$—$OR_4$;
$Y_4$) —$OCOR_5$;
$Y_5$) —$(CH_2)_p$—$OCOR_6$;
$Y_6$) —$(CH_2)_q$—OCONH—$(C_1-C_7)$alkyl;
$Y_7$) —$NR_7R_8$;
$Y_8$) —$(CH_2)_p$—$NR_9R_{10}$;
$Y_9$) —$NR_{11}C$ (=$W_1$)$R_{12}$;

$Y_{10}$) —$(CH_2)_p$—$NR_{13}C(=W_1)R_{14}$;
$Y_{11}$) —$(CH_2)_q$—$NR_{13}COOR_{15}$;
$Y_{12}$) —$(CH_2)_q$—$NR_{13}SO_2R_{16}$;
$Y_{13}$) —$(CH_2)_q$—$NR_{13}C(=W_1)$ $NR_{17}R_{18}$;
$Y_{14}$) —$C(=W_1)NR_{19}R_{20}$;
$Y_{15}$) —$CH_2$—$COOR_{21}$;
$Y_{16}$) —$CH_2$—$C(=W_1)NR_{17}R_{18}$;
$Y_{17}$)

$Y_{17}$) 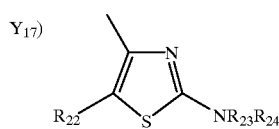

$Y_{18}$) 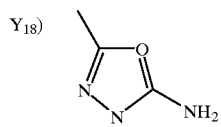

$Y_{19}$) 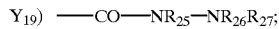 —CO—$NR_{25}$—$NR_{26}R_{27}$;

$Y_{20}$) 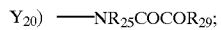 —$NR_{25}COCOR_{29}$;

$Y_{21}$) 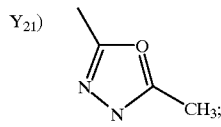

in which groups:
p is one or two;
q is zero, one or two;
$W_1$ represents an oxygen atom or a sulphur atom;
$R_3$ represents a hydrogen or a $(C_1-C_7)$alkyl;
$R_4$ represents a hydrogen; a $(C_1-C_7)$alkyl; a formyl; a $(C_1-C_7)$alkylcarbonyl;
$R_5$ represents a pyridyl; a $(C_3-C_7)$cycloalkyl unsubstituted or substituted with one or more methyls; a phenyl;
$R_6$ represents hydrogen; a $(C_1-C_7)$alkyl; a$(C_3-C_7)$ cycloalkyl unsubstituted or substituted with one or more methyls; a phenyl; a pyridyl;
$R_7$ represents a hydrogen or a $(C_1-C_7)$alkyl;
$R_8$ represents a $(C_3-C_7)$cycloalkylmethyl; a benzyl;
or alternately $R_7$ and $R_8$, together with the nitrogen atom to which they are linked, constitute a heterocycle chosen from: azetidine, thiomorpholine, perhydroazepine, piperazine unsubstituted or substituted at position 4 with a $(C_1-C_4)$alkyl;
$R_9$ represents a hydrogen or a $(C_1-C_7)$alkyl;
$R_{10}$ represents a hydrogen; a $(C_1-C_7)$alkyl; a $(C_3-C_7)$ cycloalkylmethyl; a benzyl;
$R_{11}$ represents a hydrogen or a $(C_1-C_7)$alkyl;
$R_{12}$ represents a $(C_3-C_7)$cycloalkyl unsubstituted or substituted with one or more methyls; a phenyl; a benzyl; a vinyl; a pyridyl; a furyl; a thienyl; a pyrrolyl; an imidazolyl;
or alternatively $R_{11}$ and $R_{12}$ together represent a group —$(CH_2)_m$— in which m is three or four;
$R_{13}$ represents a hydrogen or a $(C_1-C_7)$alkyl;
$R_{14}$ represents a hydrogen; a $(C_3-C_7)$ cycloalkyl unsubstituted or substituted with one or more methyls; a phenyl; a benzyl; a vinyl; a pyridyl; a furyl; a thienyl; a pyrrolyl; an imidazolyl; a $(C_1-C_7)$ alkyl $R_{15}$ represents a $(C_1-C_7)$alkyl or a phenyl;
$R_{16}$ represents a $(C_1-C_7)$alkyl; an amino, free or substituted with one or two $(C_1-C_7)$alkyls; a phenyl unsubstituted or substituted one or more times with a substituent chosen from: a halogen atom, a $(C_1-C_7)$alkyl, a trifluoromethyl, a hydroxyl, a $(C_1-C_7)$alkoxy, a carboxyl, a $(C_1-C_7)$alkoxycarbonyl, a $(C_1-C_7)$ alkylcarbonyloxy, a cyano, a nitro, an amino, free or substituted with one or two $(C_1-C_7)$alkyls, the said substituents being identical or different;
$R_{17}$ and $R_{18}$ each independently represent a hydrogen or a $(C_1-C_7)$alkyl; $R_{18}$ can, in addition, represent a $(C_3-C_7)$ cycloalkyl, a $(C_3-C_7)$ cycloalkylmethyl, a hydroxyl, a $(C_1-C_4)$alkoxy, a benzyl or a phenyl;
or alternatively $R_{17}$ and $R_{18}$, together with the nitrogen atom to which they are linked, constitute a heterocycle chosen from azetidine, pyrrolidine, piperidine, morpholine, thiomorpholine, perhydroazepine and piperazine unsubstituted or substituted at position 4 with a $(C_1-C_4)$alkyl;
$R_{19}$ represents a hydrogen or a $(C_1-C_7)$alkyl;
$R_{20}$ represents a $(C_3-C_7)$ cycloalkyl; a $(C_3-C_7)$ cycloalkylmethyl; a hydroxyl; a $(C_1-C_4)$alkoxy; a benzyl; a phenyl; $R_{20}$ can, in addition, represent a hydrogen or a $(C_1-C_7)$alkyl when n is two or three;
or alternatively $R_{19}$ and $R_{20}$, together with the nitrogen atom to which they are linked, constitute a heterocycle chosen from azetidine, thiomorpholine, perhydroazepine, piperazine and isoxazolidine; $R_{19}$ and $R_{20}$, together with the nitrogen to which they are linked, can, in addition constitute a heterocycle chosen from pyrrolidine, piperidine, morpholine and piperazine substituted at postion 4 with a $(C_1-C_4)$alkyl when n is 2 or 3;
$R_{21}$ represents a hydrogen or a $(C_1-C_7)$alkyl;
$R_{22}$ represents a hydrogen or a $(C_1-C_7)$alkyl;
$R_{23}$ and $R_{24}$ each independently represent a hydrogen or a $(C_1-C_7)$alkyl; $R_{24}$ can, in addition, represent a formyl or a $(C_1-C_7)$alkylcarbonyl;
$R_{25}$ represents a hydrogen or a $(C_1-C_7)$alkyl;
$R_{26}$ and $R_{27}$ each independently represent a hydrogen or a $(C_1-C_7)$alkyl; $R_{27}$ can, in addition, represent a $(C_1-C_7)$ alkylcarbonyl;
or alternatively $R_{26}$ and $R_{27}$, together with the nitrogen atom to which they are linked, constitute a heterocycle chosen from azetidine, pyrrolidine, piperidine, morpholine, thiomorpholine and perhydroazepine;
$R_{29}$ represents a $(C_1-C_4)$alkoxy; as well as their possible salts with inorganic or organic acids.

The family (Ic) consists of the compounds of formula:

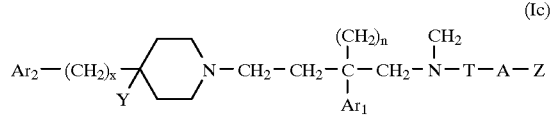

(Ic)

in which:
x, $Ar_1$, $Ar_2$, n, A and Z have the meanings given above for (I);
Y has the meaning given above for (Ib);
T represents a —CO— group; a —COO— group; a group —$CONR_{28}$— in which $R_{28}$ represents a hydrogen or a $(C_1-C_4)$alkyl;

as well as their possible salts with inorganic or organic acids.

More especially, the radical Z can be a phenyl group, which may be unsubstituted or optionally contain one or more substituents.

When Z is a phenyl group, the latter may be monosubstituted or disubstituted, in particular at positions 2,4, but also, for example, at positions 2,3 or 4,5 or 3,4 or 3,5; it may also be trisubstituted, in particular at positions 2,4,6 but also, for example, at 2,3,4 or 2,3,5 or 2,4,5 or 3,4,5; tetrasubstituted, for example at 2,3,4,5; or pentasubstituted.

The radical Z can also represent a bicyclic aromatic group such as 1- or 2-naphthyl; 1-, 2-, 3-, 4-, 5-, 6- or 7-indenyl, in which one or more bonds may be hydrogenated, it being possible for the said groups to be unsubstituted or optionally to contain one or more substituents such as: an alkyl, phenyl, cyano, hydroxyalkyl, hydroxyl, oxo, alkylcarbonylamino and alkoxycarbonyl, thioalkyl, halogen, alkoxy or trifluoromethyl group, in which groups the alkyls and the alkoxy are $C_1$–$C_4$ groups.

The radical Z can also be a pyridyl, thiadiazolyl, indolyl, indazolyl, imidazolyl, benzimidazolyl, benzotriazolyl, benzofuranyl, benzothienyl, benzothiazolyl, benzisothiazolyl, quinolyl, isoquinolyl, benzoxazolyl, benzisoxazolyl, benzoxazinyl, benzodioxinyl, isoxazolyl, benzopyrannyl, thiazolyl, thienyl, furyl, pyrannyl, chromenyl, isobenzofuranyl, pyrrolyl, pyrazolyl, pyrazinyl, pyrimidinyl, pyridazinyl, indolizinyl, phthalazinyl, quinazolinyl, acridinyl, isothiazolyl, isochromannyl or chromannyl group, in which one or more double bonds may be hydrogenated, it being possible for the said groups to be unsubstituted or optionally to contain one or more substituents such as: an alkyl, phenyl, cyano, hydroxyalkyl, hydroxyl, alkylcarbonylamino and alkoxycarbonyl or thioalkyl group, in which groups the alkyls and the alkoxy are $C_1$–$C_4$ groups.

In particular, the invention relates to compounds of formula (I) in which:

Z is Z' and represents:
a phenyl unsubstituted or substituted one or more times with a substituent chosen from: a halogen atom; a trifluoromethyl; a cyano; a hydroxyl; a nitro; an amino unsubstituted or substituted once or twice with a ($C_1$–$C_4$)alkyl; a benzylamino; a carboxyl; a ($C_1$–$C_{10}$)alkyl; a ($C_3$–$C_8$) cycloalkyl unsubstituted or substituted one or more times with a methyl; a ($C_1$–$C_{10}$)alkoxy; a ($C_3$–$C_8$)cycloalkyloxy unsubstituted or substituted one or more times with a methyl; a mercapto; a ($C_1$–$C_{10}$)alkylthio; a formyloxy; a ($C_1$–$C_6$)alkylcarbonyloxy; a formylamino; a ($C_1$–$C_6$)alkylcarbonylamino; a benzoylamino; a ($C_1$–$C_4$)alkoxycarbonyl; a ($C_3$–$C_7$)cycloalkyloxycarbonyl; a carbamoyl unsubstituted or substituted once or twice with a ($C_1$–$C_4$)alkyl; a ureido unsubstituted or substituted once or twice at position 3 with a ($C_1$–$C_4$)alkyl or a ($C_3$–$C_7$)cycloalkyl; a (1-pyrrolidinyl)carbonylamino, the said substituents being identical or different;
a naphthyl unsubstituted or substituted one or more times with a halogen, a trifluoromethyl, a ($C_1$–$C_4$)alkyl, a hydroxyl, a ($C_1$–$C_4$)alkoxy; p2 a pyridyl; a thienyl; an indolyl; a quinolyl; a benzothienyl; an imidazolyl.

Furthermore, Z' may also represent a phenyl substituted with a phenyl unsubstituted or substituted one or more times with a halogen, a trifluoromethyl, a ($C_1$–$C_4$)alkyl, a hydroxyl, a ($C_1$–$C_4$)alkoxy, the said substituents being identical or different;

In the present description, the alkyl or alkoxy groups are straight or branched; halogen atom is understood to mean a chlorine, bromine, fluorine or iodine atom.

In the substituents of the group Z=phenyl, ($C_1$–$C_{10}$)alkyl is understood to mean, for example, a methyl, an ethyl, an n-propyl, an isopropyl, an n-butyl, an isobutyl, a sec-butyl, a tert-butyl, a pentyl or n-pentyl, a hexyl or n-hexyl, a heptyl or an n-heptyl, an octyl or n-octyl, a nonyl or n-nonyl, a decyl or an n-decyl; ($C_3$–$C_8$)cycloalkyl optionally substituted with a methyl is understood to mean, for example, a cyclopropyl, a cyclobutyl, a cyclopentyl, a 1-, 2- or 3-methylcyclopentyl, a cyclohexyl, a 1-, 2-, 3- or 4-methylcyclohexyl, a cycloheptyl or a cyclooctyl; ($C_1$–$C_{10}$)alkoxy is understood to mean, for example, a methoxy, an ethoxy, an n-propoxy, an isopropoxy, an n-butoxy, an isobutoxy, a sec-butoxy, a tert-butoxy, a pentyloxy, a hexyloxy, a heptyloxy, an octyloxy, a nonyloxy or a decyloxy; ($C_3$–$C_8$)cycloalkyloxy optionally substituted with a methyl is understood to mean, for example, a cyclopropyloxy, a cyclobutyloxy, a cyclopentyloxy, a 1-, 2- or 3-methylcyclopentyloxy, a cyclohexyloxy, a 1-, 2-, 3- or 4-methylcyclohexyloxy, a cycloheptyloxy or a cyclooctyloxy; ($C_1$–$C_{10}$)alkylthio is understood to mean, for example, a methylthio, an ethylthio, an n-propylthio, an isopropylthio, an n-butylthio, an isobutylthio, a sec-butylthio, a tert-butylthio, a pentylthio, a hexylthio, a heptylthio, an octylthio, a nonylthio or a decylthio; ($C_1$–$C_6$)alkylcarbonyloxy is understood to mean, for example, an acetyloxy, a propionyloxy, a butyryloxy, a valeryloxy, a caproyloxy, a heptanoyloxy; a ($C_1$–$C_6$)alkylcarbonyl-amino is understood to mean, for example, an acetylamino, a propionylamino, a butyrylamino, an isobutyrylamino, a valerylamino, a caproylamino or a heptanoylamino; ($C_1$–$C_4$)alkoxycarbonyl is understood to mean, for example, a methoxycarbonyl, an ethoxycarbonyl, an n-propoxycarbonyl, an isopropoxycarbonyl, an n-butoxycarbonyl, an isobutoxycarbonyl, a sec-butoxycarbonyl or a tert-butoxycarbonyl; ($C_3$–$C_7$)cycloalkyloxycarbonyl is understood to mean, for example, a cyclopropyloxycarbonyl, a cyclobutyloxycarbonyl, a cyclopentyloxycarbonyl, a cyclohexyloxycarbonyl or a cycloheptyloxycarbonyl.

Advantageously, the radical Z represents a phenyl unsubstituted or substituted one or more times with a halogen atom, more especially a chlorine, fluorine or iodine atom, a trifluoromethyl, a ($C_1$–$C_4$)alkyl, a hydroxyl, a ($C_1$–$C_4$)alkoxy; a naphthyl unsubstituted or substituted one or more times with a halogen, a trifluoromethyl, a ($C_1$–$C_4$)alkyl, a hydroxyl, a ($C_1$–$C_4$)alkoxy; a pyridyl; a thienyl; an indolyl; a quinolyl; a benzothienyl; an imidazolyl.

According to the present invention, preference is given to the compounds of formula (I) in which:

x is zero or one;
$R_1$ represents hydrogen;
$R_2$ represents a hydrogen or a ($C_1$–$C_7$)alkyl;
or alternatively $R_1$ and $R_2$ together constitute a group —$(CH_2)_n$—CQ— in which Q represents an oxygen atom or two hydrogen atoms and n is one, two or three;

Y represents a group chosen from:
- $Y_1$) $(C_1-C_7)$alkyl;
- $Y_2$) —$(CH_2)_p$—$OR_3$;
- $Y_3$) —O—$CH_2CH_2$—$OR_4$;
- $Y_4$) —$OCOR_5$;
- $Y_5$) —$(CH_2)_p$—$OCOR_6$;
- $Y_6$) —$(CH_2)_q$—OCONH—$(C_1-C_7)$ alkyl;
- $Y_7$) —$NR_7R_8$;
- $Y_8$) —$(CH_2)_p NR_9R_{10}$;
- $Y_9$) —$NR_{11}COR_{12}$;
- $Y_{10}$) —$(CH_2)_p$—$NR_{13}COR_{14}$;
- $Y_{11}$) —$(CH_2)_q$—$NR_{13}COOR_{15}$;
- $Y_{12}$) —$(CH_2)_q$—$NR_{13}SO_2R_{16}$;
- $Y_{13}$) —$(CH_2)_q$—$NR_{13}CONR_{17}R_{18}$;
- $Y_{14}$) —$CONR_{19}R_{20}$;
- $Y_{15}$) —$CH_2$—$COOR_{21}$;
- $Y_{16}$) —$CH_2$—$CONR_{17}R_{18}$;
- $Y_{17}$)

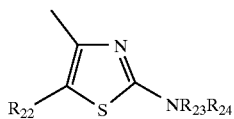

- $Y_{18}$)

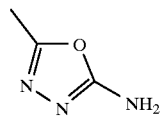

- $Y_{19}$) —CO—$NR_{25}$—$NR_{26}R_{27}$;

in which groups:

p is one or two;

q is zero, one or two;

$R_3$ represents a $(C_1-C_7)$alkyl; $R_3$ can, in addition, represent hydrogen when $R_1$ and $R_2$ together constitute a group —$(CH_2)_n$—CQ—;

$R_4$ represents a hydrogen; a $(C_1-C_7)$alkyl; a formyl; a $(C_1-C_7)$alkylcarbonyl;

$R_5$ represents a pyridyl or a $(C_3-C_7)$cycloalkyl unsubstituted or substituted with one or more methyls; $R_5$ can, in addition, represent a phenyl when $R_1$ and $R_2$ together constitute a group —$(CH_2)_n$—CQ—;

$R_6$ represents hydrogen; a $(C_1-C_7)$alkyl; a $(C_3-C_7)$cycloalkyl unsubstituted or substituted with one or more methyls; a phenyl; a pyridyl;

$R_7$ represents a hydrogen or a $(C_1-C_7)$alkyl;

$R_8$ represents a $(C_3-C_7)$cycloalkylmethyl; a benzyl;

or alternately $R_7$ and $R_8$, together with the nitrogen atom to which they are linked, constitute a heterocycle chosen from: azetidine, thiomorpholine, perhydroazepine, piperazine unsubstituted or substituted at position 4 with a $(C_1-C_4)$alkyl; $R_7$ and $R_8$ together with the nitrogen atom to which they are linked can, in addition, constitute a heterocycle chosen from pyrrolidine, piperidine and morpholine when $R_1$ represents hydrogen;

$R_9$ represents a hydrogen or a $(C_1-C_7)$alkyl;

$R_{10}$ represents a $(C_1-C_7)$alkyl; a $(C_3-C_7)$ cycloalkylmethyl; a benzyl; $R_{10}$ can, in addition, represent hydrogen when $R_1$ and $R_2$ together constitute a group —$(CH_2)_n$—CQ—;

$R_{11}$ represents a hydrogen or a $(C_1-C_7)$alkyl;

$R_{12}$ represents a $(C_3-C_7)$cycloalkyl unsubstituted or substituted with one or more methyls; a phenyl; a benzyl; a vinyl; a pyridyl; a furyl; a thienyl; a pyrrolyl; an imidazolyl; $R_{12}$ can, in addition, represent hydrogen when $R_1$ represents hydrogen; $R_{12}$ can, in addition, represent a $(C_1-C_7)$alkyl when both $R_{11}$ represents a $(C_1-C_7)$alkyl and $R_1$ represents hydrogen;

or alternatively $R_{11}$ and $R_{12}$ together represent a group —$(CH_2)_m$— in which m is three or four;

$R_{13}$ represents a hydrogen or a $(C_1-C_7)$alkyl;

$R_{14}$ represents a hydrogen; a $(C_3-C_7)$ cycloalkyl unsubstituted or substituted with one or more methyls; a phenyl; a benzyl; a vinyl; a pyridyl; a furyl; a thienyl; a pyrrolyl; an imidazolyl; $R_{14}$ can, in addition, represent a $(C_1-C_7)$alkyl when $R_1$ and $R_2$ together constitute a group —$(CH_2)_n$—CQ—; $R_{14}$ can, in addition, represent a $(C_1-C_7)$alkyl when both $R_{13}$ represents a $(C_1-C_7)$alkyl and $R_1$ represents hydrogen;

$R_{15}$ represents a $(C_1-C_7)$alkyl or a phenyl;

$R_{16}$ represents a $(C_1-C_7)$alkyl; an amino, free or substituted with one or two $(C_1-C_7)$alkyls; a phenyl unsubstituted or substituted one or more times with a substituent chosen from: a halogen atom, a $(C_1-C_7)$alkyl, a trifluoromethyl, a hydroxyl, a $(C_1-C_7)$alkoxy, a carboxyl, a $(C_1-C_7)$alkoxycarbonyl, a $(C_1-C_7)$alkylcarbonyloxy, a cyano, a nitro, an amino, free or substituted with one or two $(C_1-C_7)$alkyls, the said substituents being identical or different;

$R_{17}$ and $R_{18}$ each independently represent a hydrogen or a $(C_1-C_7)$alkyl; $R_{18}$ can, in addition, represent a $(C_3-C_7)$ cycloalkyl, a $(C_3-C_7)$ cycloalkylmethyl, a hydroxyl, a $(C_1-C_4)$alkoxy, a benzyl or a phenyl;

or alternatively $R_{17}$ and $R_{18}$, together with the nitrogen atom to which they are linked, constitute a heterocycle chosen from azetidine, pyrrolidine, piperidine, morpholine, thiomorpholine, perhydroazepine and piperazine unsubstituted or substituted at position 4 with a $(C_1-C_4)$alkyl;

$R_{19}$ represents a hydrogen or a $(C_1-C_7)$alkyl;

$R_{20}$ represents a $(C_3-C_7)$ cycloalkyl; a $(C_3-C_7)$ cycloalkylmethyl; a hydroxyl; a $(C_1-C_4)$alkoxy; a benzyl; a phenyl; $R_{20}$ can, in addition, represent a hydrogen or a $(C_1-C_7)$alkyl when $R_1$ represents hydrogen or when $R_1$ and $R_2$ together constitute a group —$(CH_2)_n$—CQ— in which n is two or three.;

or alternatively $R_{19}$ and $R_{20}$, together with the nitrogen atom to which they are linked, constitute a heterocycle chosen from azetidine, thiomorpholine, perhydroazepine and piperazine; $R_{19}$ and $R_{20}$, together with the nitrogen atom to which they are linked, can, in addition, constitute a heterocycle chosen from, pyrrolidine, piperidine, morpholine and piperazine substituted at position 4 with a $(C_1-C_4)$alkyl when $R_1$ represents hydrogen or when $R_1$ and $R_2$ together constitute a group $(CH_2)_n$—CQ— in which n is two or three;

$R_{21}$ represents a hydrogen or a $(C_1-C_7)$alkyl;

$R_{22}$ represents a hydrogen or a $(C_1-C_7)$alkyl;

$R_{23}$ and $R_{24}$ each independently represent a hydrogen or a $(C_1-C_7)$alkyl; $R_{24}$ can, in addition, represent a formyl or a $(C_1-C_7)$alkylcarbonyl;

$R_{25}$ represents a hydrogen or a $(C_1-C_7)$alkyl;

$R_{26}$ and $R_{27}$ each independently represent a hydrogen or a $(C_1-C_7)$alkyl;

Ar$_1$ represents a phenyl unsubstituted or substituted one or more times with a substituent chosen from: a halogen atom, a hydroxyl, a (C$_1$–C$_4$)alkoxy, a (C$_1$–C$_4$)alkyl, a trifluoromethyl, a methylenedioxy, the said substituents being identical or different; a thienyl unsubstituted or substituted with a halogen atom; a benzothienyl unsubstituted or substituted with a halogen atom; a naphthyl unsubstituted or substituted with a halogen atom; an indolyl unsubstituted or N-substituted with a (C$_1$–C$_4$)alkyl or a benzyl; an imidazolyl unsubstituted or substituted with a halogen atom; a pyridyl unsubstituted or substituted with a halogen atom; a biphenyl;

Ar$_2$ represents a phenyl unsubstituted or substituted one or more times with a substituent chosen from: a halogen atom, a hydroxyl, a (C$_1$–C$_4$)alkoxy, a (C$_1$–C$_4$)alkyl, a trifluoromethyl, a methylenedioxy, the said substituents being identical or different; a pyridyl; a thienyl; a pyrimidyl; an imidazolyl unsubstituted or substituted with a (C$_1$–C$_4$)alkyl;

T represents a —CH$_2$— group; a —CO— group; a —COO— group; a group —CONR$_{28}$— in which R$_{28}$ represents a hydrogen or a (C$_1$–C$_4$)alkyl; on condition that T represents a —CH$_2$— group when Q represents an oxygen atom and T represents one of the groups —CO—, —COO— or —CONR$_{28}$— when Q represents two hydrogen atoms;

A represents a direct bond or a group —(CH$_2$)$_t$— in which t is one, two or three;

Z represents an optionally substituted mono-, di- or tricyclic aromatic or heteroaromatic group;

as well as their possible salts with inorganic or organic acids.

The substituent Ar$_1$ is preferably a phenyl group advantageously substituted with two chlorine atoms or two fluorine atoms, more especially in positions 3 and 4.

The substituent Ar$_2$ is preferably an unsubstituted phenyl.

The substituent Y is preferably a group chosen from:

Y$_2$) —(CH$_2$)$_p$—OR$_3$;
Y$_3$) —O—CH$_2$CH$_2$—OR$_4$;
Y$_5$) —(CH$_2$)$_p$—OCOR$_6$;
Y$_6$) —(CH$_2$)$_q$—OCONH—(C$_1$–C$_7$ )alkyl;
Y$_9$) —NR$_{11}$COR$_{12}$;
Y$_{11}$) —(CH$_2$ )$_q$—NR$_{13}$COOR$_{15}$;
Y$_{12}$) —(CH$_2$)$_q$—NR$_{13}$SO$_2$R$_{16}$;
Y$_{13}$) —(CH$_2$)$_q$—NR$_{13}$CONR$_{17}$R$_{18}$;
Y$_{14}$ ) —CONR$_{19}$R$_{20}$;
Y$_{15}$) —CH$_2$—COOR$_{21}$;
Y$_{17}$ )

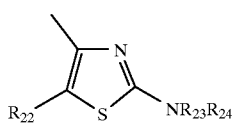

Y$_{18}$)

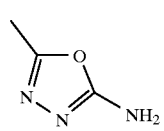

Y$_{19}$ ) —CO—NR$_{25}$—NR$_{26}$R$_{27}$;
in which groups p, q, R$_3$, R$_4$, R$_6$, R$_{11}$, R$_{12}$, R$_{13}$, R$_{15}$, R$_{16}$, R$_{17}$, R$_{18}$, R$_{19}$, R$_{20}$, R$_{21}$, R$_{22}$, R$_{23}$, R$_{24}$, R$_{25}$, R$_{26}$ and R$_{27}$ are as defined above for a compound of formula (I).

A group of preferred compounds according to the present invention are those of formula:

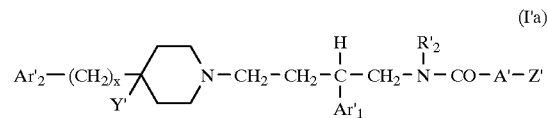
(I'a)

in which:
x is as defined above for a compound of formula (I);
R'$_2$ represents a (C$_1$–C$_7$)alkyl;
Y' represents a group chosen from:
Y$_3$) —O—CH$_2$CH$_2$—OR$_4$;
Y$_6$) —(CH$_2$)$_q$—OCONH—(C$_1$–C$_7$)alkyl;
Y$_9$) —NR$_{11}$COR$_{12}$;
Y$_{11}$) —(CH$_2$)$_q$—NR$_{13}$COOR$_{15}$;
Y$_{12}$) —(CH$_2$)$_q$—NR$_{13}$SO$_2$R$_{16}$;
Y$_{13}$ ) —(CH$_2$)$_q$—NR$_{13}$CONR$_{17}$R$_{18}$;
Y$_{14}$) —CONR$_{19}$R$_{20}$;
Y$_{15}$) —CH$_2$—COOR$_{21}$;
Y$_{17}$)

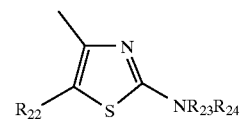

Y$_{18}$)

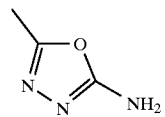

Y$_{19}$) —CO—NR$_{25}$—NR$_{26}$R$_{27}$;
in which groups q, R$_4$, R$_{11}$, R$_{12}$, R$_{13}$, R$_{15}$, R$_{16}$, R$_{17}$, R$_{18}$, R$_{19}$, R$_{20}$, R$_{21}$, R$_{22}$, R$_{23}$, R$_{24}$, R$_{25}$, R$_{26}$ and R$_{27}$ are as defined for a compound of formula (Ia);

Ar'$_1$ represents a phenyl unsubstituted or substituted one or more times with a substituent chosen from: a halogen atom, a hydroxyl, a (C$_1$–C$_4$)alkoxy, a (C$_1$–C$_4$)alkyl, a trifluoromethyl, a methylenedioxy, the said substituents being identical or different;

Ar'$_2$ represents a phenyl unsubstituted or substituted one or more times with a substituent chosen from: a halogen atom, a hydroxyl, a (C$_1$–C$_4$)alkoxy, a (C$_1$–C$_4$)alkyl, a trifluoromethyl, a methylenedioxy, the said substituents being identical or different;

A' represents a direct bond or a —CH$_2$— group;
Z' is as defined above;
and their salts with inorganic or organic acids.

Among these compounds, those of formula:

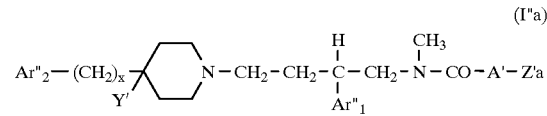
(I"a)

in which:
x, Y' and A' are as defined for a compound of formula (I'a);
Ar"$_1$ represents a 3,4-dichlorophenyl or a 3,4-difluorophenyl;

Ar"2 represents an unsubstituted phenyl;

Z'a represents an unsubstituted phenyl or a phenyl substituted at position 3 with a halogen or a $(C_1-C_{10})$ alkoxy;

and their salts with inorganic or organic acids, are especially preferred.

Among these compounds, those of formula:

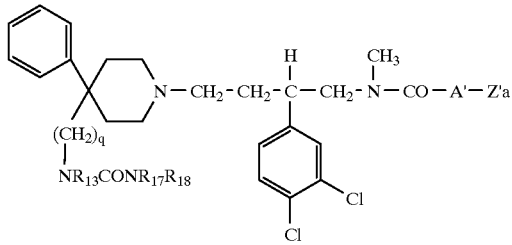

(I'''a)

in which:

A' is as defined for a compound of formula (I'a);

Z'a is as defined for a compound of formula (I''a);

q, $R_{13}$, $R_{17}$ and $R_{18}$ are as defined for a compound of formula (Ia) ;

and their salts with inorganic or organic acids, are most especially preferred.

The compounds of formula (I'''a ) in optically pure form, and their salts with inorganic or organic acids, are more especially preferred.

Another group of preferred compounds according to the invention are those of formula:

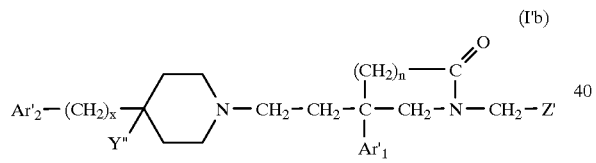

(I'b)

in which:

n and x are as defined above for a compound of formula (I);

Ar'$_1$, Ar'$_2$ and Z' are as defined above for a compound of formula (I'a);

Y" represents a group chosen from:

$Y_3$) —O—CH$_2$CH$_2$—OR$_4$;
$Y_6$) —(CH$_2$)$_q$—OCONH—(C$_1$–C$_7$)alkyl;
$Y_9$) —NR$_{11}$COR$_{12}$;
$Y_{11}$) —(CH$_2$)$_q$—NR$_{13}$COOR$_{15}$;
$Y_{12}$) —(CH$_2$)$_q$—NR$_{13}$SO$_2$R$_{16}$;
$Y_{13}$) —(CH$_2$)$_q$—NR$_{13}$CONR$_{17}$R$_{18}$;
$Y_{14}$) —CONR$_{19}$R$_{20}$;
$Y_{15}$) —CH$_2$—COOR$_{21}$;
$Y_{17}$)

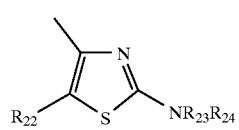

$Y_{18}$)

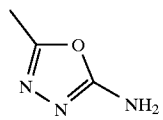

$Y_{19}$) —CO—NR$_{25}$—NR$_{26}$R$_{27}$;

in which groups q, $R_4$, $R_{11}$, $R_{12}$, $R_{13}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$ and $R_{27}$ are as defined for a compound of formula (Ib);

and their salts with inorganic or organic acids.

Among these compounds, those of formula:

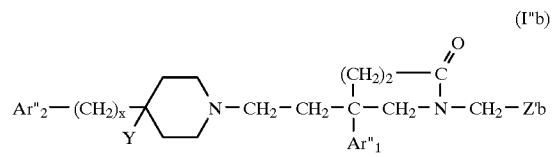

(I"b)

in which:

x and Y" are as defined for a compound of formula (I'b);

Ar"$_1$ and Ar"$_2$ are as defined for a compound of formula (I"a);

Z'b represents an unsubstituted phenyl, a 3,5-bis (trifluoromethyl)phenyl, a 3,5-dimethylphenyl or a 2,4-bis(trifluoromethyl)phenyl;

and their salts with inorganic or organic acids, are especially preferred.

Among these compounds, those of formula:

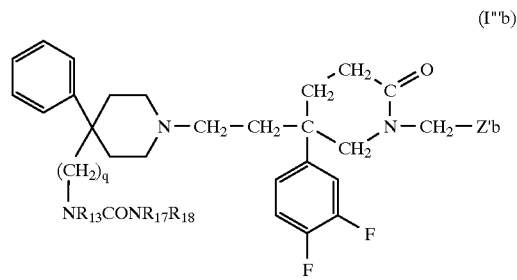

(I'''b)

in which:

Z'b is as defined for a compound of formula (I"b);

q, $R_{13}$, $R_{17}$ and $R_{18}$ are as defined for a compound of formula (Ib);

and their salts with inorganic or organic acids, are most especially preferred.

The compounds of formula (I'''b) in optically pure form, and their salts with inorganic or organic acids, are more especially preferred.

Another group of preferred compounds according to the invention are those of formula:

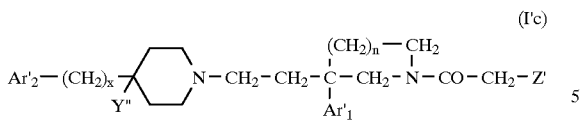
(I'c)

in which:

x and n are as defined for a compound of formula (I);

Ar'$_1$, Ar'$_2$ and Z' are as defined for a compound of formula (I'a);

Y" is as defined for a compound of formula (I'b);

and their salts with inorganic or organic acids.

Among these compounds, those of formula:

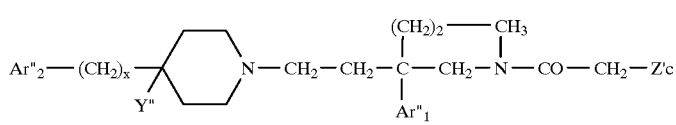
(I"c)

in which:

x and Y" are as defined for a compound of formula (I'c);

Ar"$^1$ and Ar"$_2$ are as defined for a compound of formula (I"a);

Z'c represents a phenyl substitued at position 3 with a halogen or a (C$_1$–C$_{10}$)alkoxy group; and their salts with inorganic or organic acids, are especially preferred.

According to another of its aspects, the present invention relates to the obtaining of the compounds of formula (I) of and their salts.

One of the processes according to the invention for obtaining the compounds (process A) is suitable for the preparation of the compounds of formula (I) in which R$_1$ and R$_2$ together constitute a group —(CH$_2$)$_n$—CQ— in which Q represents an oxygen atom and n is one, two or three [compounds of formula (Ib)].

This process is characterized in that:

1) a compound of formula:

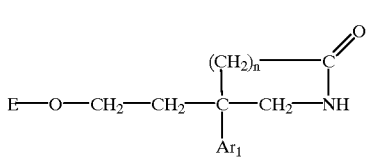
(II)

in which n and Ar$_1$ are as defined for a compound of formula (I) and E represents hydrogen or an O-protecting group, is treated with a halogenated derivative of formula:

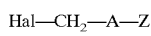
Hal—CH$_2$—A—Z (III)

in which Hal represents a halogen atom, preferably bromine, and A and Z are as defined above for a compound of formula (I), to obtain a compound of formula:

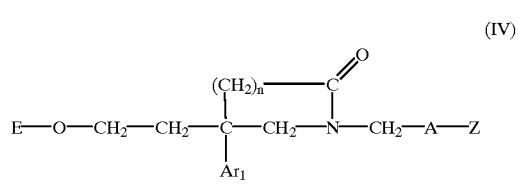
(IV)

2) the O-protecting group is, where appropriate, removed by the action of an acid or a base, to obtain the alcohol of formula:

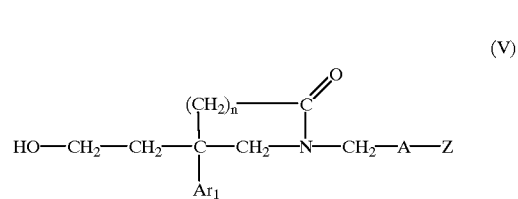
(V)

3) the alcohol (V) is treated with a compound of formula:

G—SO$_2$—Cl  (VI)

in which G represents a methyl, phenyl, tolyl or trifluoromethyl group, to obtain a compound of formula:

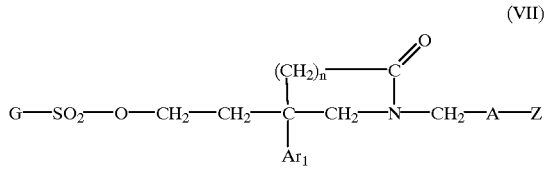
(VII)

4) the compound (VII) is reacted with a piperidine of formula:

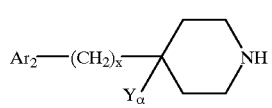
(VIII)

in which x and Ar$_2$ are as defined for a compound of formula (I) and Y$_\alpha$ represents either Y as defined for (I) or a precursor of Y, on the understanding that, when Y$_\alpha$ contains a hydroxyl group or an amino group, these groups may be protected;

5) and, after deprotection, where appropriate, of the hydroxyl groups or the amino groups, or conversion, where appropriate, of Y$_\alpha$ to Y, the product thereby obtained is optionally converted to one of its salts with an inorganic or organic acid.

Another process according to the invention for obtaining the compounds (process B) is suitable for the preparation of the compounds of formula (I) in which $R_1$ and $R_2$ together constitute a group —$(CH_2)_n$—CQ— in which Q represents two hydrogen atoms and n is one, two or three (compounds of formula [(Ic)], or the compounds of formula (I) in which $R_1$ represents hydrogen [compounds of formula (Ia)].

This process is characterized in that:

1) a compound of formula:

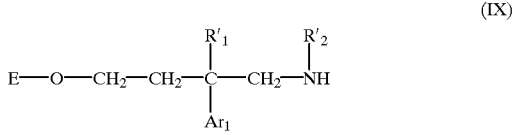
(IX)

in which $Ar_1$ is as defined for a compound of formula (I), $R'_1$ represents hydrogen and $R'_2$ represents a hydrogen or a $(C_1-C_7)$alkyl, or alternatively $R'_1$ and $R'_2$ together constitute a group —$(CH_2)_n$—CQ— in which Q represents two hydrogen atoms and n is one, two or three, and E represents hydrogen or an O-protecting group, is treated either with a halogenated derivative of formula:

Hal—$CH_2$—A—Z (III)

in which Hal represents a halogen atom, preferably bromine, and A and Z are as defined for a compound of formula (I), when $R_1$ represents hydrogen and $R_2$ represents hydrogen or a $(C_1-C_7)$alkyl, when a compound of formula (Ia) is to be prepared in which T is —$CH_2$—;

or with a functional derivative of an acid of formula:

HO—CO—A—Z (IIIa)

in which A and Z are as defined above, when a compound of formula (I) is to be prepared in which T is —CO—;

or with a chloroformate of formula:

Cl—COO—A—Z (IIIb)

in which A and Z are as defined above, when a compound of formula (I) is to be prepared in which T is —COO—;

or with an isocyanate of formula:

O=C=N—A—Z (IIIc)

in which A and Z are as defined above, when a compound of formula (I) is to be prepared in which T is a group —CO—$NR_{28}$— in which $R_{28}$ represents hydrogen;

or with a carbamoyl chloride of formula:

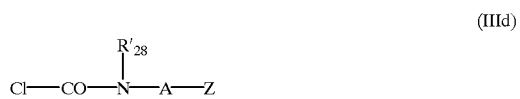
(IIId)

in which A and Z are as defined above and $R'_{28}$ represents a $(C_1-C_4)$alkyl, when a compound of formula (I) is to be prepared in which T is —$CONR_{28}$— in which $R_{28}$ is a $(C_1-C_4)$alkyl;

to obtain a compound of formula:

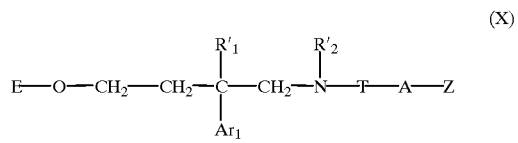
(X)

2) where appropriate, when $R'_2$ represents hydrogen, and on condition that T is other than —CO—NH— or that —T—A— is other than —CO—$(CH_2)_t$—, an alkylation reaction is performed to obtain a compound of formula (X) in which $R'_2$ represents a $(C_1-C_7)$alkyl;

3) the O-protecting group is, where appropriate, removed from the compound obtained in step 1) or in step 2) by the action of an acid or a base, to obtain the alcohol of formula:

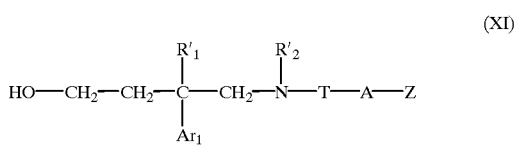
(XI)

4) the alcohol (XI) is treated with a compound of formula:

G—$SO_2$—Cl (VI)

in which G represents a methyl, phenyl, tolyl or trifluoromethyl group, to obtain a compound of formula:

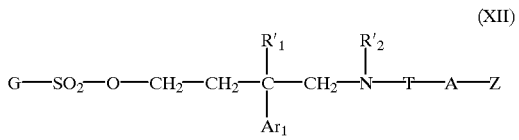
(XII)

5) the compound (XII) is reacted with a piperidine of formula (VIII) as defined above;

6) and, after deprotection, where appropriate, of the hydroxyl groups or the amino groups, or conversion, where appropriate, of $Y_\alpha$ to Y, the product thereby obtained is optionally converted to one of its salts with an inorganic or organic acid.

During any one of the steps of the processes A or B for preparing the compounds of formula (I), and more especially when compounds of formula (VIII) or intermediate compounds of formula (II) or (IX) are employed, it may be necessary and/or desirable to protect the reactive or sensitive functional groups, such as the amine, hydroxyl or carboxyl groups, present on any one of the molecules in question. This protection may be performed using conventional protective groups, such as the ones described in Protective Groups in Organic Chemistry, J. F. W. McOmie, Ed. Plenum Press, 1973 and in Protective Groups in Organic Synthesis, T. W. Greene and P. G. M. Wutts, Ed. John Wiley and Sons, 1991. Removal of the protective groups may take place in an opportune subsequent step using methods known to a person skilled in the art which do not affect the remainder of the molecule in question.

Thus, in process A or in process B, when E represents an O-protecting group, the latter is chosen from the traditional O-protecting groups well known to a person skilled in the art, such as, for example, tetrahydro-2-pyranyl, benzoyl or a $(C_1-C_4)$alkylcarbonyl.

The O-protecting groups used, where appropriate, to obtain a compound of formula (I) in which Y contains a hydroxyl are the traditional O-protecting groups well known to a person skilled in the art, as defined above for E.

The N-protecting groups used, where appropriate, to obtain a compound of formula (I) in which Y contains an amino group are the traditional N-protecting groups well known to a person skilled in the art, such as, for example, the trityl, methoxytrityl, tert-butoxycarbonyl or benzyloxycarbonyl group.

In step 1) of process A or in step 1) of process B, when a halogenated derivative of formula (III) is used, the reaction is performed in an inert solvent such as tetrahydrofuran, N,N-dimethylformamide or dimethyl sulphoxide in the presence of a base such as potassium tert-butylate, sodium hydride or lithium diisopropylamide and at a temperature of between 0° C. and 80° C.

In step 1) of process B, as a functional derivative of the acid (IIIa), the acid itself is used, or alternatively one of the functional derivatives which react with amines, for example an anhydride, a mixed anhydride, the acid chloride or an activated ester such as the para-nitrophenyl ester.

When the acid of formula (IIIa) itself is employed, the reaction is carried out in the presence of a coupling agent used in peptide chemistry, such as 1,3-dicyclohexylcarbodiimide or benzotriazol-1-yloxy-tris(dimethylamino)phosphonium hexafluorophosphate, in the presence of a base such as triethylamine or N,N-diisopropylethylamine, in an inert solvent such as dichloromethane or N,N-dimethylformamide at a temperature between 0° C. and room temperature.

When an acid chloride is used, the reaction is performed in an inert solvent such as dichloromethane or benzene, in the presence of a base such as triethylamine or N-methylmorpholine and at a temperature between –60° C. and room temperature.

When a chloroformate of formula (IIIb) is used, the reaction is performed in an inert solvent such as dichloromethane, at a temperature between 0° C. and room temperature and in the presence of a base such as triethylamine.

When an isocyanate of formula (IIIc) is used, the reaction is performed in an inert solvent such as dichloromethane or benzene at room temperature.

When a carbamoyl chloride of formula (IIId) is used, the reaction is performed in a solvent such as toluene or 1,2-dichloroethane, at a temperature of between 0° C. and 110° C. and in the presence of a base such as triethylamine.

In step 2) of process B, where appropriate, a compound of formula (X) in which $R'_2$ represents hydrogen is subjected to a subsequent treatment to prepare a compound of formula (X) in which $R'_2$ represents a $(C_1-C_7)$alkyl. The alkylation reaction is performed by the action of a $C_1-C_7$ alkyl halide or sulphate, in the presence of a base such as sodium hydride, in an inert solvent such as tetrahydrofuran, N,N-dimethylformamide or toluene, at a temperature between 0° C. and room temperature.

In step 2) of process A or in step 3) of process B, where appropriate, the compound of formula (IV) or the compound or formula (X) thereby obtained is deprotected according to methods known to a person skilled in the art. For example, when E represents a tetrahydro-2-pyranyl group, the deprotection is performed by acid hydrolysis using hydrochloric acid in a solvent such as ether, methanol or a mixture of these solvents, or using pyridinium p-toluenesulphonate in a solvent such as methanol, or alternatively using an Amberlyst® resin in a solvent such as methanol. The reaction is performed at a temperature between room temperature and refluxing temperature of the solvent. When E represents a benzoyl group or a $(C_1-C_4)$alkylcarbonyl group, deprotection is performed by hydrolysis in an alkaline medium using, for example, an alkali metal hydroxide such as sodium hydroxide, potassium hydroxide or lithium hydroxide, in an inert solvent such as water, methanol, ethanol, dioxane or a mixture of these solvents, at a temperature of between 0° C. and the refluxing temperature of the solvent.

In step 3) of process A according to step 4) of process B, the reaction of the alcohol of formula (V) or of the alcohol of formula (XI) with a sulphonyl chloride of formula (VI) is performed in the presence of a base such as triethylamine, pyridine, N,N-diisopropylethylamine or N-methylmorpholine, in an inert solvent such as dichloromethane, benzene or toluene and at a temperature between –20° C. and the refluxing temperature of the solvent.

In step 4) of process A or in step 5) of process B, the compound (VII) or the compound (XII) thereby obtained is reacted with a piperidine of formula (VIII). The reaction is performed in an inert solvent such as N,N-dimethylformamide, acetonitrile, methylene chloride, toluene or isopropanol and in the presence or absence of a base. When a base is used, the latter is chosen from organic bases such as triethylamine, N,N-diisopropylethylamine and N-methyl-morpholine, or from alkali metal carbonates or bicarbonates such as potassium carbonate, sodium carbonate and sodium bicarbonate. In the absence of base, the reaction is performed using an excess of the compound of formula (VIII) and optionally in the presence of an alkali metal iodide such as potassium iodide or sodium iodide. The reaction is performed at a temperature between room temperature and 100° C.

Finally, after deprotection, where appropriate, of the hydroxyl groups or the amino groups, or conversion, where appropriate, of $Y_\alpha$ to Y, the compounds of formula (I) according to the invention are obtained.

The compounds of formula (I) are isolated in free base or salt form according to traditional techniques.

Thus, when the compound of formula (I) is obtained in free base form, salification is performed by treatment with the chosen acid in an organic solvent. By treatment of the free base, dissolved, for example, in an ether such as diethyl ether or in an alcohol such as 2-propanol or in acetone or in dichloromethane or in ethyl acetate, with a solution of the chosen acid in the same solvent, the corresponding salt is obtained and is isolated according to traditional techniques.

Thus, the hydrochloride, hydrobromide, sulphate, hydrogen sulphate, dihydrogen phosphate, methane sulphonate, oxalate, maleate, fumarate, 2-naphthalenesulphonate or benzenesulphonate is, for example, prepared.

At the end of the reaction, the compounds of formula (I) may be isolated in the form of one of their salts, for example the hydrochloride or the oxalate; in this case, if necessary, the free base may be prepared by neutralization of the said salt with an inorganic or organic base such as sodium hydroxide or triethylamine or with an alkali metal carbonate or bicarbonate such as sodium or potassium carbonate or bicarbonate.

The compounds of formula (II) are obtained by known methods, especially the ones which are described in Patent Application EP-A-0512901.

In particular, a compound of formula (II) in which n=2 may be prepared according to Scheme 1 below.

SCHEME 1

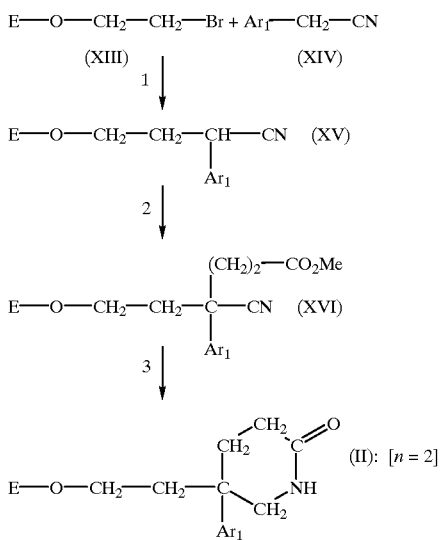

In step 1 of SCHEME 1, a compound of formula (XIII) is reacted with a compound of formula (XIV) according to the method described in Patent Applications EP-A-0428434 and EP-A-0474561.

In step 2, the reaction of the compound of formula (XV) thereby obtained with methyl acrylate in the presence of a base such as Triton® B or 1,8-diazabi-cyclo[5.4.0]undec-7-ene (DBU) enables the compound of formula (XVI) to be obtained.

In step 3, the compound of formula (XVI) is subjected to a hydrogenation in the presence of a catalyst such as Raney® nickel, to obtain the compound of formula (II) in which n=2.

The compounds of formula (IX) are obtained by known methods, especially the ones which are described in Patent Applications EP-A-0428434, EP-A-0474561, EP-A-0512901 and EP-A-591040.

The compounds of formula (III), (IIIa), (IIIb), (IIIc) or (IIId) are known, or prepared by known methods.

The piperidines of formula (VIII) are known, or are prepared by known methods such as the ones described in the following publications:

J. Org. Chem., 1957, 22, 1484–1489;
J. Heterocyclic Chem., 1986, 23, 73–75;
J. Chem. Soc., 1945, 917;
J. Pharmaceutical Sci., 1972, 61 (8), 1316–1317;
Chem. Ber., 1975, 108, 3475–3482.

The compounds of formula (VIII) are generally prepared in a form protected on the piperidine nitrogen; after a deprotection step, the compounds of formula (VIII) themselves are obtained.

More especially, a compound of formula (VIII) in which $Y_\alpha$ represents a group $—(CH_2)_p—OR_3$ in which $R_3$ represents hydrogen and p is one or two, respectively, is, for example, prepared by reduction of a compound of formula (VIII) in which $Y_\alpha$ represents a methoxycarbonyl or a methoxycarbonylmethyl, respectively, according to the method described in Chem. Ber., 1975, 108, 3475–3482.

A compound of formula (VIII) in which $Y_\alpha$ represents a group $—(CH_2)_p—OR_3$ in which $R_3$ represents a $(C_1-C_7)$ alkyl is prepared by alkylation of a compound of formula (VIII) in which $Y_\alpha$ represents a group $—(CH_2)_p—OH$ according to methods known to a person skilled in the art.

A compound of formula (VIII) in which $Y_\alpha$ represents a group $—O—CH_2—CH_2—OR_4$ in which $R_4$ represents hydrogen is prepared by reaction of a compound of formula (VIII) in which $Y_\alpha$ represents a benzoyloxy with ethylene glycol in the presence of an acid such as sulphuric acid.

By an identical reaction, and using a 2-$(C_1-C_7)$ alkoxyethanol, the compounds of formula (VIII) are prepared in which $Y_\alpha$ represents a group $—O—CH_2CH_2—OR_4$ in which $R_4$ represents a $(C_1-C_7)$alkyl.

By the action of formic acid on a compound of formula (VIII) in which $Y_\alpha$ represents an $—O—CH_2CH_2—OH$ group, the compounds of formula (VIII) are prepared in which $Y_\alpha$ represents a group $—O—CH_2CH_2—OR_4$ in which $R_4$ represents a formyl. By the action of a $C_2-C_8$ acid chloride, and in the presence of a base such as triethylamine, the compounds of formula (VIII) are prepared in which $Y_\alpha$ represents a group $—O—CH_2CH_2—OR_4$ in which $R_4$ represents a $(C_1-C_7)$ alkylcarbonyl.

A compound of formula (VIII) in which $Y_\alpha$ represents a group $—OCOR_5$ is prepared by reaction of an acid chloride $R_5COCl$ on a compound of formula (VIII) in which $Y_\alpha$ represents a hydroxyl, and in the presence of a base such as triethylamine.

Similarly, by the action of an acid chloride $R_6COCl$ ($R_6$ other than hydrogen) on a compound of formula (VIII) in which $Y_\alpha$ represents a group $—(CH_2)_p—OH$, the compounds of formula (VIII) are prepared in which $Y_\alpha$ represents a group $—(CH_2)_p—OCOR_6$ ($R_6$ other than hydrogen).

By the action of formic acid on a compound of formula (VIII) in which $Y_\alpha$ represents a group $—(CH_2)_p—OH$, the compounds of formula (VIII) are prepared in which $Y_\alpha$ represents a group $—(CH_2)_p—OCOR_6$ in which $R_6$ represents hydrogen.

By the action of a carbamoyl chloride $(C_1-C_7)$alkyl-NHCOCl on the compounds of formula (VIII) in which $Y_\alpha$ represents a group $—(CH_2)_Q OH$, the compounds of formula (VIII) are obtained in which $Y_\alpha$ represents a group $—(CH_2)_q—OCONH—(C_1-C_7)$alkyl. The same compounds are prepared by the action of an isocyanate $(C_1-C_7)$alkyl-N=C=O on the compounds of formula (VIII) in which $Y_\alpha$ represents a group $—(CH_2)_q—OH$.

To prepare a compound of formula (VIII) in which $Y_\alpha$ represents a group $—NR_7R_8$ in which $R_7$ represents hydrogen and $R_8$ represents a $(C_3-C_7)$ cycloalkylmethyl or a benzyl, respectively, it is possible to perform a reduction of a compound of formula (VIII) in which $Y_\alpha$ represents a group —$NR_{11}COR_{12}$ in which $R_{11}$ represents hydrogen and $R_{12}$ represents a $(C_3-C_7)$ cycloalkyl or a phenyl, respectively. The reaction is performed by means of a reducing agent such as lithium aluminium hydride in a solvent such as tetrahydrofuran at the refluxing temperature of the solvent.

By an identical reaction, the compounds of formula (VIII) in which $Y_\alpha$ represents a group —$NR_7R_8$ in which $R_7$ represents a $(C_1-C_7)$alkyl may be prepared from the compounds of formula (VIII) in which $Y_\alpha$ represents a group —$NR_{11}COR_{12}$ in which $R_{11}$ represents a $(C_1-C_7)$alkyl.

A compound of formula (VIII) in which $Y_\alpha$ represents a group —$NR_7R_8$ in which $R_7$ and $R_8$, together with the nitrogen atom to which they are linked, constitute a heterocycle is prepared by application or adaptation of the Bruylants reaction (Bull. Soc. Chim. Belges, 1924, 33, 467 and Tetrahedron Letters, 1988, 29 (52), 6827–6830).

To prepare a compound of formula (VIII) in which $Y_\alpha$ represents a group —$CH_2$—$NR_9R_{10}$ in which $R_9$ and $R_{10}$ each represent hydrogen, the reduction is performed with a compound of formula (VIII) in which $Y_\alpha$ represents a cyano. This reduction is performed according to methods well known to a person skilled in the art.

A compound of formula (VIII) in which $Y_\alpha$ represents a group —$CH_2$—$CH_2$—$NR_9R_{10}$ in which $R_9$ and $R_{10}$ each represent a hydrogen is prepared from a compound of formula (VIII) in which $Y_\alpha$ represents a —$CH_2$—$CH_2$—OH group, by application or adaptation of the method described in J. Med. Chem., 1989, 32, 391–396.

The compounds of formula (VIII) in which $Y_\alpha$ represents a group —$(CH_2)_p$—$NR_9R_{10}$ in which $R_9$ represents a hydrogen or a $(C_1-C_7)$alkyl and $R_{10}$ represents a $(C_1-C_7)$alkyl, a $(C_3-C_7)$cycloalkylmethyl or a benzyl may be prepared by reduction of a compound of formula (VIII) in which $Y_\alpha$ represents a group —$(CH_2)_p$—$NR_{13}COR_{14}$ in which $R_{13}$ represents a hydrogen or a $(C_1-C_7)$alkyl and $R_{14}$ represents a $(C_1-C_6)$alkyl, a $(C_3-C_7)$cycloalkyl or a phenyl.

The compounds of formula (VIII) in which $Y_\alpha$ represents a group —$NR_{11}COR_{12}$ in which $R_{11}$ represents a hydrogen or a $(C_1-C_7)$alkyl and $R_{12}$ represents hydrogen or a $(C_1-C_7)$ alkyl, a $(C_3-C_7)$cycloalkyl, a phenyl, a benzyl, a vinyl, a pyridyl, a furyl, a thienyl, a pyrrolyl or an imidazolyl, respectively, are obtained by the action of formic acid in acetic anhydride or of a suitable acid chloride $R_{12}COCl$, respectively, in the presence of a base such as triethylamine, on a compound of formula (VIII) in which $Y_\alpha$ represents a group —$NHR_{11}$. In particular, a compound of formula (VIII) in which $Y_\alpha$ represents a group —$NR_{11}COR_{12}$ in which $R_{12}$ represents an ethyl radical may be prepared by hydrogenation, in the presence of a catalyst such as palladium on charcoal, of a compound of formula (VIII) in which $Y_\alpha$ represents an acryloylamino or acryloyl-N-$(C_1-C_7)$ alkylamino group.

A compound of formula (VIII) in which $Y_\alpha$ represents a group —$NR_{11}COR_{12}$ in which $R_{11}$ and $R_{12}$ together represent a —$(CH_2)_3$— or —$(CH_2)_4$— group is prepared by application or adaptation of the method described in J. Med. Chem., 1985, 28, 46–50.

To prepare a compound of formula (VIII) in which $Y_\alpha$ represents an amino group, a hydrolysis of a compound of formula (VIII) in which $Y_\alpha$ represents an acetamido group is performed in an acid medium.

The compounds of formula (VIII) in which $Y_\alpha$ represents a group —$(CH_2)_p$—$NR_{13}COR_{14}$ in which p is 1 or 2, $R_{13}$ represents a hydrogen or a $(C_1-C_7)$alkyl and $R_{14}$ represents a hydrogen or a $(C_1-C_7)$alkyl, a phenyl, a benzyl, a pyridyl an optionally substituted $(C_3-C_7)$cycloalkyl, a vinyl, a furyl, a thienyl, a pyrrolyl or an imidazolyl, respectively, are obtained by the action of formic acid in acetic anhydride or of a suitable acid chloride $R_{14}COCl$, respectively, in the presence of a base such as triethylamine, on a compound of formula (VIII) in which $Y_\alpha$ represents a group —$CH_2$—$NHR_{13}$ or —$CH_2$—$CH_2$—$NHR_{13}$.

By the action of a chloroformate of formula $ClCOOR_{15}$ on a compound of formula (VIII) in which $Y_\alpha$ represents a group —$(CH_2)_q$—$NHR_{13}$, in the presence of a base such as triethylamine, a compound of formula (VIII) is prepared in which $Y_\alpha$ represents a group —$(CH_2)_q$—$NR_{13}COOR_{15}$.

It is also possible to prepare a compound of formula (VIII) in which $Y_\alpha$ represents a group —$(CH_2)_q$—$NR_{13}COOR_{15}$ in which q=0 and $R_{13}$ represents hydrogen by the action of a compound $R_{15}OH$ with a compound of formula (VIII) in which $Y_\alpha$ represents an isocyanato group (—N=C=O).

A compound of formula (VIII) in which $Y_\alpha$ represents an isocyanato group is prepared from a compound of formula (VIII) in which $Y_\alpha$ represents a carboxyl according to the method described in Organic Synthesis, 51, 48–52.

By the action of a sulphonyl chloride $ClSO_2R_{16}$ on a compound of formula (VIII) in which $Y_\alpha$ represents a group —$(CH_2)_q$—$NHR_{13}$, in the presence of a base such as triethylamine, a compound of formula (VIII) is prepared in which $Y_\alpha$ represents a group —$(CH_2)_{ql}$ —$_{NR13}SO_2R_{16}$.

Similarly, by the action of an isocyanate of formula $R_{18}N=C=O$ in which $R_{18}$ represents a $(C_1-C_7)$alkyl, the compounds of formula (VIII) are prepared in which $Y_\alpha$ represents a group —$(CH_2)_q$—$NR_{13}CONR_{17}R_{18}$ in which $R_{17}$ represents a hydrogen and $R_{18}$ represents a $(C_1-C_7)$ alkyl.

By the action of a carbamoyl chloride of formula $ClCONR_{17}R_{18}$, the compounds of formula (VIII) are prepared in which $Y_\alpha$ represents a group —$(CH_2)_q$—$NR_{13}CONR_{17}R_{18}$ in which $R_{17}$ represents a $(C_1-C_7)$alkyl and $R_{18}$ represents a $(C_1-C_7)$alkyl or a cycloalkyl.

It is also possible to obtain a compound of formula (VIII) in which $Y_\alpha$ represents a group —$(CH_2)_q$—$NR_{13}CONR_{17}R_{18}$ by the action of a compound $HNR_{17}R_{18}$ in which $R_{17}$ and $R_{18}$ are as defined for the compounds of formula (I), with a compound of formula (VIII) in which $Y_{60}$ represents a group —$(CH_2)_q$—$NR_{13}COOR_{15}$ in which $R_{15}$ represents a phenyl.

A compound of formula (VIII) in which $Y_\alpha$ represents a group —$(CH_2)_q$—$NR_{13}CONR_{17}R_{18}$ in which q=0 and $R_{13}$ represents hydrogen may also be prepared by the action of a compound $NHR_{17}R_{18}$ with a compound of formula (VIII) in which $Y_\alpha$ represents an isocyanato group.

To prepare a compound of formula (VIII) in which $Y_\alpha$ represents a group —$CONR_{19}R_{20}$, a compound of formula (VIII) in which $Y_\alpha$ represents a carboxyl is reacted with a compound of formula $HNR_{19}R_{20}$ according to methods well known to a person skilled in the art.

Similarly, the compounds of formula (VIII) in which $Y_\alpha$ represents a group —$CH_2$—$CONR_{17}R_{18}$, are prepared by reaction of a compound of formula (VIII) in which $Y_\alpha$ represents a group —$CH_2$—$COOR_{21}$ in which $R_{21}$ represents hydrogen with a compound $HNR_{17}R_{18}$.

A compound of formula (VIII) in which $Y_\alpha$ represents a carboxyl may be prepared by hydrolysis of a compound of formula (VIII) in which $Y_\alpha$ represents a cyano, according to methods known to a person skilled in the art.

A compound of formula (VIII) in which $Y_\alpha$ represents a carboxymethyl may be prepared according to the method described in Chem. Ber., 1975, 108, 3475–3482.

A compound of formula (VIII) in which $Y_\alpha$ represents a $(C_1-C_7)$alkoxycarbonyl or a $(C_1-C_7)$alkoxycarbonylmethyl, respectively, may be prepared from a compound of formula (VIII) in which $Y_\alpha$ represents a carboxyl or a carboxymethyl, respectively, by an esterification reaction according to methods well known to a person skilled in the art.

To prepare a compound of formula (VIII) in which $Ar_2$ represents an optionally substituted phenyl radical, x is one and $Y_\alpha$ represents a $(C_1-C_7)$ alkoxycarbonyl, a protected 4-$(C_1-C_7)$alkoxy-carbonylpiperidine is reacted with an optionally substituted benzyl halide in the presence of a base such as sodium hydride, potassium tert-butylate or sodium diisopropylamide in a solvent such as tetrahydrofuran, N,N-dimethylformamide or dimethyl sulphoxide, at a temperature between −78° C. and room temperature. After a deprotection step, the expected compound of formula (VIII) is obtained.

To prepare a compound of formula (VIII) in which $Y_\alpha$ represents a group

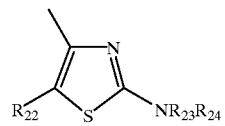

in which $R_{23}$ and $R_{24}$ each independently represent a hydrogen or a $(C_1-C_7)$alkyl, a compound of formula (VIII) in which $Y_\alpha$ represents a group

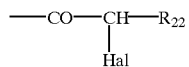

in which Hal represents a halogen atom, preferably bromine, is reacted with a thiourea in which one of the amino groups is free or substituted with one or two $(C_1-C_7)$ alkyls.

A compound of formula (VIII) in which $Y_\alpha$ represents a group

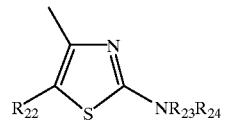

in which $R_{24}$ represents a formyl or a $(C_1-C_7)$alkylcarbonyl, respectively, is prepared by reaction of formic acid in acetic anhydride or of an acid chloride $(C_1-C_7)$alkyl-COCl, respectively, in the presence of a base such as triethylamine, with the compound of formula (VIII; above protected on the piperidine nitrogen, and in which $R_{24}$ represents hydrogen. After a deprotection step, the expected compound is obtained.

The compound of formula (VIII) in which $Y_\alpha$ represents a group

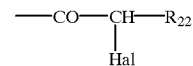

in which Hal represents a bromine atom is obtained by bromination according to traditional methods of a compound of formula (VIII) in which $Y_\alpha$ represents a group —CO—$CH_2R_{22}$.

A compound of formula (VIII) in which $Y_\alpha$ represents a group

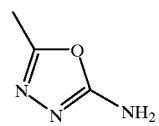

may be prepared by reaction of a protected compound of formula (VIII) in which $Y_\alpha$ represents a carbazoyl group (—CONH—$NH_2$) with cyanogen bromide according to the method described in J. Org. Chem., 1961, 26, 88–95. The compound of formula (VIII) in which $Y_\alpha$ represents a carbazoyl group is obtained by reaction of hydrazine with a compound of formula (VIII) in which $Y_\alpha$ represents a chloroformyl, which is itself obtained by reaction of thionyl chloride with a compound of formula (VIII) in which $Y_\alpha$ represents a carboxyl.

A compound of formula (VIII) in which $Y_\alpha$ represents a group —CO—$NR_{25}$—$NR_{26}R_{27}$ is prepared by reaction of a hydrazine $HNR_{25}$—$NR_{26}R_{27}$ with a compound of formula (VIII) in which $Y_\alpha$ represents a chloroformyl.

A compound of formula (VIII) in which $Y_\alpha$ represents a group —$NR_{11}C$ (=$W_1$)$R_{12}$ or a group —$(CH_2)_p$—$NR_{13}C$ (=$W_1$)$R_{14}$ in which groups $W_1$ represents a sulphur atom is prepared from a corresponding compound of formula (VIII) protected on the piperidine nitrogen, and in which $W_1$ represents an oxygen atom by reaction with phosphorus pentasulphide or with Lawesson's reagent, 2,4-bis(4-methoxyphenyl)-1,3-dithia-2,4-diphosphetane-2,4-disulphide, followed by deprotection of the pipe-idine nitrogen.

By reaction of a compound of formula (VIII), protected on the piperidine nitrogen, in which $Y_\alpha$ represents a group —$(CH_2)_q$—$NR_{13}CONR_{17}R_{18}$ with phosphorus pentasulphide or with Lawesson's reagent, a compound of formula (VIII) is prepared in which $Y_\alpha$ represents a group —$(CH_2)_q$—$NR_{13}C$(=$W_1$)$NR_{17}R_{18}$ in which $W_1$ is a sulphur atom.

According to the methods mentioned above, a compound of formula (VIII) in which $Y_\alpha$ represents a group —C(=$W_1$)$NR_{19}R_{20}$ or a group —$CH_2$—C(=$W_1$)$NR_{17}R_{18}$ in which groups $W_1$ represents a sulphur atom is prepared from a corresponding compound of formula (VIII) in which $W_1$ represents an oxygen atom.

A compound of formula (VIII) in which $Y_\alpha$ represents a group —$NR_{25}COCOR_{29}$ in which $R_{29}$ represents a $(C_1-C_4)$ alkoxy is prepared by reaction of a compound of formula Cl—$COCOR_{29}$ with a compound of formula (VIII) in which $Y_\alpha$ represents an —$NHR_{25}$ group.

A compound of formula (VIII) in which $Y_\alpha$ represents a group:

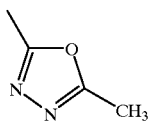

is prepared by heating a protected compound of formula (VIII) in which $Y_\alpha$ represents a —CONH—NH—CO—CH$_3$ group in the presence of p-toluenesulphonic acid.

The enantiomers of the compounds according to the invention, of formula:

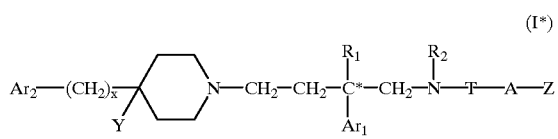
(I*)

in which:
"*" means that the carbon atom thus labelled has the particular (+) or (−) absolute configuration;
x, R$_1$, R$_2$, Y, Ar$_1$, Ar$_2$, T, A and Z are as defined for the compounds of formula (I);
as well as their salts with inorganic or organic acids;
are new compounds which form part of the invention.

The resolution of the racemic mixtures of the compounds of formula (I) enables the enantiomers of formula (I*) to be isolated. It is, however, preferable to perform the resolution of the racemic mixtures from an intermediate compound which is useful for the preparation of a compound of formula (I), as described in Patent Applications: EP-A-0474561, EP-A-0512901, EP-A-0612716 and EP-A-0591040.

The compounds of formula (I) above also comprise those in which one or more hydrogen, carbon or iodine atoms have been replaced by their radioactive isotope, for example tritium, carbon-14 or iodine-125. Such labelled compounds are useful in research, metabolic or pharmacokinetic work, in biochemical tests as receptor ligands.

The affinity of the compounds for the tachykinin receptors was evaluated in vitro by several biochemical tests using radioligands:

1) The binding of [$^{125}$I]BH-SP (substance P labelled with iodine-125 using the Bolton-Hunter reagent) to the NK$_1$ receptors of human lymphoblast cells.
2) The binding of [$^{125}$I]His-NKa to the NK$_2$ receptors of rat duodenum or bladder.
3) The binding of [$^{125}$I]His[MePhe$^7$]NK$_B$ to the NK$_3$ receptors of rat cerebral cortex, of guinea pig cerebral cortex and of gerbil cerebral cortex, as well as to cloned human NK$_3$ receptors expressed by CHO cells (Buell et al., FEBS Letters, 1992, 299, 90–95).

The tests were performed according to X. Emonds-Alt et al., (Eur. J. Pharmacol., 1993, 250, 403–413).

The compounds according to the invention display an affinity for the tachykinin receptors mentioned above, with an inhibition constant Ki of generally less than $10^{-8}$M.

The compounds of the present invention are, in particular, active principles of pharmaceutical compositions, the toxicity of which is compatible with their use as medicinal products.

The compounds of the present invention are generally administered as dosage units. The said dosage units are preferably formulated in pharmaceutical compositions in which the active principle is mixed with a pharmaceutical excipient.

Thus, according to another of its aspects, the present invention relates to pharmaceutical compositions containing as active principle a compound of formula (I) or one of its pharmaceutically acceptable salts.

The compounds of formula (I) above and their pharmaceutically acceptable salts may be used at daily doses of 0.01 to 100 mg per kilo body weight of the mammal to be treated, preferably at daily doses of 0.1 to 50 mg/kg. In human beings, the dose can preferably vary from 0.5 to 4000 mg daily, and more especially from 2.5 to 1000 mg according to the age of the subject to be treated or the type of treatment: prophylactic or curative.

In the pharmaceutical compositions of the present invention for oral, sublingual, inhalation, subcutaneous, intramuscular, intravenous, transdermal, local or rectal administration, the active principles may be administered in single-dose administration forms, mixed with traditional pharmaceutical vehicles, to animals and to human beings. Suitable single-dose administration forms comprise forms for oral administration such as tablets, gelatin capsules, powders, granules and oral solutions or suspensions, forms for sublingual and buccal administration, aerosols, implants, forms for subcutaneous, intramuscular, intravenous, intranasal or intraocular administration and forms for rectal administration.

When a solid composition is prepared in the form of tablets, the main active principle is mixed with a pharmaceutical vehicle such as silica, gelatin, starch, lactose, magnesium stearate, talc, gum arabic or the like. The tablets may be coated with sucrose, with various polymers or with other suitable materials, or alternatively treated in such a way that they have a sustained or delayed activity and that they release a predetermined amount of active principle continuously.

A preparation in gelatin capsules is obtained by mixing the active principle with a diluent such as a glycol or a glycerol ester and incorporating the mixture obtained in hard or soft gelatin capsules.

A preparation in syrup or elixir form can contain the active principle together with a sweetener, preferably of the non-caloric type, methylparaben and propylparaben as antiseptic, as well a flavour-imparting agent and a suitable colorant.

The water-dispersible powders or granules can contain the active principle mixed with dispersing agents or wetting agents, or suspending agents such as polyvinylpyrrolidone, as well as with sweeteners or flavour correctors.

For rectal administration, suppositories are employed, which are prepared with binding agents that melt at rectal temperature, for example cocoa butter or polyethylene glycols.

For parenteral, intranasal or intraocular administration, aqueous suspensions, isotonic saline solutions or sterile and injectable solutions are used, which contain pharmacologically compatible dispersing agents and/or wetting agents, for example propylene glycol or butylene glycol.

For administration by inhalation, an aerosol is used containing, for example, sorbitan trioleate or oleic acid as well as trichlorofluoromethane, dichlorofluoromethane, dichlorotetrafluoroethane or any other biologically compatible propellant gas; it is also possible to use a system containing the active principle alone or combined with an excipient, in powder form.

The active principle may also be formulated in the form of microcapsules, optionally with one or more vehicles or additives.

In each dosage unit, the active principle of formula (I) is present in the amounts suited to the daily doses envisaged. In general, each dosage unit is appropriately adjusted according to the dosage and the type of administration planned, for example tablets, gelatin capsules and the like, sachets, ampoules, syrups and the like, or drops, so that such a dosage unit contains from 0.5 to 1000 mg of active principle, and preferably from 2.5 to 250 mg, which doses are to be administered one to four times daily.

The abovementioned compositions may also contain other active products such as, for example, bronchodilators, antitussives, antihistamines, anti-inflammatories, anti-emetics or chemotherapeutic agents.

According to another of its aspects, the present invention relates to the use of the products of formula (I) for the preparation of medicinal products intended for treating physiological disorders associated with an excess of tachykinins, and all neurokinin-dependent pathologies of the respiratory, gastrointestinal, urinary, immune and cardiovascular systems and the central nervous system, as well as pain and migraine.

For example and without limitation:

- acute and chronic pains associated, for example, with migraine, with cancer and anginal pains, with chronic inflammatory processes such as osteoarthritis and rheumatoid arthritis,
- inflammations such as neurogenic inflammations, chronic inflammatory diseases, for example chronic obstructive respiratory diseases, asthma, allergies, rhinitis, coughs, bronchitis, hypersensitivity, for example to pollens and to mites, rheumatoid arthritis, fibrositis, osteoarthritis, psoriasis, ulcerative colitis, Crohn's disease, intestinal inflammation (irritable colon), prostatitis, neurological bladder, incontinence, cystitis, urethritis, nephritis, ophthalmic diseases such as conjunctivitis, vitreoretinopathy, skin diseases such as contact dermatitis, atopic dermatitis, urticaria, eczema, pruritus, burns, in particular sunburn,
- diseases of the immune system associated with the suppression or stimulation of the functions of the immune cells, for example rheumatoid arthritis, psoriasis, Crohn's disease, diabetes, lupus, rejection reactions after transplantation,
- small cell cancer of the lung, demyelinating diseases such as multiple sclerosis or amyotropic lateral sclerosis,
- diseases of the central nervous system of the neuropsychiatric or neurological type, such as anxiety, disorders of vigilance or of mood, depression, psychosis, schizophrenia, mania, dementia, epilepsy, Parkinson's disease, Alzheimer's disease, drug dependence, Down's syndrome and Huntington's chorea, as well as neurodegenerative diseases and somatic disorders associated with stress,
- diseases of the gastrointestinal system, such as nausea, vomiting of any origin, irritable colon, gastric and duodenal ulcers, oesophageal ulcers, diarrhoea, hypersecretion,
- diseases of the cardiovascular system such as hypertension, the vascular aspects of migraine, oedema, thrombosis, angina pectoris, vascular spasms, circulatory diseases due to a vasodilatation, Raynaud's disease, fibrosis, collagen diseases,
- disorders of heart rate and rhythm, especially those caused by pain or stress.

The present invention also includes a method for treating the said complaints at the doses indicated above.

In the preparations and in the examples, the following abbreviations are used:

Me, OMe: methyl, methoxy
Et, OEt: ethyl, ethoxy
EtOH: ethanol
MeOH: methanol
Ether: diethyl ether
Iso ether: diisopropyl ether
DMF: dimethylformamide
DMSO: dimethyl sulphoxide
DCM: dichloromethane
THF: tetrahydrofuran
AcOEt: ethyl acetate
$K_2CO_3$: potassium carbonate
$Na_2CO_3$: sodium carbonate
$KHCO_3$: potassium hydrogen carbonate
$NaHCO_3$: sodium hydrogen carbonate
NaCl: sodium chloride
$Na_2SO_4$: sodium sulphate
$MgSO_4$: magnesium sulphate
NaOH: sodium hydroxide
AcOH: acetic acid
$H_2SO_4$: sulphuric acid
HCl: hydrochloric acid
ethereal hydrogen chloride: saturated solution of hydrochloric acid in ether
BOP: benzotriazol-1-yloxytris(dimethylamino)-phosphonium hexafluorophosphate
KCN: potassium cyanide
DBU: 1,8-diazabicyclo[5.4.0]undec-7-ene
$NH_4Cl$: ammonium chloride
m.p.: melting point
RT: room temperature
silica H: silica gel 60H marketed by Merck (DARMSTADT)
NMR: nuclear magnetic resonance
δ: chemical shift
s: singlet
bs: broad singlet
ss: split singlet
d: doublet
t: triplet
qt: quartet
sept: septet
mt: multiplet
UC: unresolved complex

PREPARATION 1.1

4-(2-Hydroxyethoxy)-4-phenylpiperidine hydrochloride

A) 1-Benzyl-4-hydroxy-4-phenylpiperidine.

This compound is prepared by the action of phenyllithium on 1-benzyl-4-piperidone according to the process described in EP-A-474561.

B) 4-(Benzoyloxy)-1-benzyl-4-phenylpiperidine.

A solution of 2.67 g of the compound prepared in the preceding step, 2.5 ml of triethylamine and 30 ml of DCM is cooled to 0–5° C., 1.22 ml of benzoyl chloride are added and the mixture is left stirring for 1 hour while allowing the temperature to rise to RT. The reaction mixture is concentrated under vacuum, the residue is extracted with AcOEt, the organic phase is washed with water and with 1N NaOH solution and dried over $MgSO_4$ and the solvent is evaporated off under vacuum. 2.4 g of the expected product are obtained after crystallization in pentane.

C) 1-Benzyl-4-(2-hydroxyethoxy)-4-phenylpiperidine hydrochloride.

A mixture of 2.3 g of the compound obtained in the preceding step, 7 ml of $H_2SO_4$ and 60 ml of ethylene glycol is heated to 60° C. for 5 hours. The reaction mixture is poured onto ice and alkalinized by adding concentrated $NH_4OH$ solution, the product is extracted with DCM, the organic phase is washed with water and dried over $MgSO_4$ and the solvent is evaporated off under vacuum. The residue is chromatographed on silica, eluting with DCM and then with a DCM/MeOH (96:4; v/v) mixture. The product obtained is dissolved in DCM, the mixture is acidified to pH 1 by adding ethereal hydrogen chloride and the precipitate formed is drained. 1 g of the expected product is obtained.

D) 4-(2-Hydroxyethoxy)-4-phenylpiperidine hydrochloride.

A mixture of 3.3 g of the compound obtained in the preceding step and 0.4 g of palladium on charcoal (10% Pd) in 100 ml of EtOH is hydrogenated at RT and at atmospheric pressure. The catalyst is filtered off on Celite® and the filtrate is concentrated under vacuum. 2.2 g of the expected product are obtained, m.p.=168–172° C.

PREPARATION 1.2

4-(2-Methoxyethoxy)-4-phenylpiperidine hydrochloride

A) 1-Benzyl-4-(2-methoxyethoxy)-4-phenylpiperidine hydrochloride.

A solution of 4.7 g of the compound obtained in step B of PREPARATION 1.1 in 50 ml of 2-methoxyethanol is cooled to 5° C., 10 ml of $H_2SO_4$ are added dropwise, and the reaction mixture is left stirring while allowing the temperature to rise to RT and is then heated to 30–40° C. for 4 hours. The reaction mixture is poured onto ice and alkalinized to pH 10 by adding concentrated $NH_4OH$ solution, the product is extracted with DCM, the organic phase is washed with water and dried over $MgSO_4$ and the solvent is evaporated off under vacuum. The residue is chromatographed on silica, eluting with DCM and then with a DCM/MeOH (99:1; v/v) mixture. The product obtained is dissolved in DCM, the mixture is acidified to pH 1 by adding ethereal hydrogen chloride and the precipitate formed is drained. 1.5 g of the expected product are obtained.

B) 4-(2-Methoxyethoxy)-4-phenylpiperidine hydrochloride

A mixture of 1.5 g of the compound obtained in the preceding step and 0.18 g of palladium on charcoal (10% Pd) in 50 ml of EtOH is hydrogenated at RT and at atmospheric pressure. The catalyst is filtered off on Celite® and the filtrate is concentrated under vacuum. 0.8 g of the expected product is obtained.

PREPARATION 1.3

4-(Formylamino)-4-phenylpiperidine hydrochloride
A) 4-Acetamido-1-benzyl-4-phenylpiperidine.

This compound is prepared by the action of acetonitrile on the compound obtained in step A of PREPARATION 1.1 according to the process described in EP-A-474561.

B) 4-Amino-1-benzyl-4-phenylpiperidine dihydrochloride.

A mixture of 50 g of the compound obtained in the preceding step and 90 ml of concentrated HCl solution in 210 ml of water is heated to reflux for 48 hours. The reaction mixture is concentrated under vacuum, the residue is taken up in an EtOH/toluene mixture and the solvents are evaporated off under vacuum. The residue is dissolved in 100 ml of hot MeOH, 500 ml of acetone are added and the mixture is left stirring while cooling in an ice bath. The crystals formed are drained, washed with acetone and then with ether and dried. 48.9 g of the expected product are obtained.

C) 1-Benzyl-4-(formylamino)-4-phenylpiperidine hydrochloride.

4.5 ml of acetic anhydride are added dropwise to a solution of 2 g of the compound obtained in the preceding step and 0.9 g of sodium formate in 14 ml of formic acid, and the mixture is left stirring for 48 hours at RT. It is concentrated under vacuum, the residue is taken up with water and alkalinized by adding concentrated NaOH, the product is extracted with DCM, the organic phase is dried over $MgSO_4$ and the solvent is evaporated off under vacuum. The product obtained is taken up in DCM, and the mixture is acidified to pH 1 by adding ethereal hydrogen chloride and evaporated under vacuum. 1.7 g of the expected product are obtained after crystallization in acetone, m.p.=225° C. (dec).

D) 4-(Formylamino)-4-phenylpiperidine hydrochloride.

A mixture of 1.7 g of the compound obtained in the preceding step, 0.2 g of palladium on charcoal (10% Pd) and 50 ml of 95% EtOH is hydrogenated at RT and at atmospheric pressure. The catalyst is filtered off and the filtrate is evaporated under vacuum. 1.1 g of the expected product are obtained after crystallization in acetone, m.p.=217° C.

PREPARATION 1.4

4-(Acetyl-N-methylamino)-4-phenylpiperidine p-toluenesulphonate
A) 1-Benzyl-4-(formylamino)-4-phenylpiperidine.

110 ml of acetic anhydride are added dropwise to a solution of 48.9 g of the compound obtained in step B of PREPARATION 1.3 and 25 g of sodium formate in 340 ml of formic acid, and the reaction mixture is left stirring overnight at RT. It is concentrated under vacuum, the residue is taken up in water and alkalinized by adding concentrated NaOH solution, the product is extracted with DCM, the organic phase is dried over $MgSO_4$ and the solvent is evaporated off under vacuum. 38.8 g of the expected product are obtained after crystallization in an iso ether/pentane mixture, m.p.=140° C.

B) 1-Benzyl-4-(methylamino)-4-phenylpiperidine.

A solution of 38.8 g of the compound obtained in the preceding step in 400 ml of THF is added slowly to a suspension of 12.5 g of lithium aluminium hydride in 100 ml of THF, and the mixture is heated to reflux for 3 hours. After cooling, a concentrated solution of 5 ml of NaOH in 45 ml of water is added to the reaction mixture, the inorganic salts are filtered off and the filtrate is concentrated under vacuum. 38 g of the expected product are obtained.

C) 4-(Acetyl-N-methylamino)-1-benzyl-4-phenyl-piperidine.

A solution of 30 g of the compound obtained in the preceding step and 16.5 ml of triethylamine in 300 ml of DCM is cooled to 0–5° C., 8 ml of acetyl chloride are added dropwise and the reaction mixture is left stirring for 30 minutes at RT. It is washed twice with water and with 2N NaOH solution, the organic phase is dried over MgSO$_4$ and the solvent is evaporated off under vacuum. 31.6 g of the expected product are obtained after crystallization in an iso ether/pentane mixture, m.p.=104° C.

D) 4-(Acetyl-N-methylamino)-4-phenylpiperidine p-toluenesulphonate.

A mixture 0.5 g of the compound obtained in the preceding step, 2.9 g of p-toluenesulphonic acid monohydrate, 0.5 g of palladium on charcoal (10% Pd) and 80 ml of EtOH is hydrogenated for 3 hours at 25° C. and at atmospheric pressure. The catalyst is filtered off and the filtrate is concentrated under vacuum. 5.7 g of the expected product are obtained after crystallization in acetone, m.p.=165° C.

PREPARATION 1.5

4-(Methoxycarbonylamino)-4-phenylpiperidine p-toluenesulphonate hemihydrate.

A) 1-tert-Butoxycarbonyl-4-carboxy-4-phenyl-piperidine.

32.9 g of K$_2$CO$_3$ are added to a mixture of 30 g of 4-carboxy-4-phenylpiperidine p-toluenesulphonate in 300 ml of dioxane and 30 ml of water, the mixture is then heated to 600C and 18.2 g of di-tert-butyl dicarbonate are added dropwise. The mixture is thereafter heated for 2 hours to 60° C. and then for 30 minutes to reflux. After cooling to RT, the reaction mixture is concentrated under vacuum, the residue is extracted with DCM, the organic phase is washed with a pH 2 buffer solution, with 2N HCl solution to pH 4, with a pH 2 buffer solution, with water and with saturated NaCl solution and dried over MgSO$_4$ and the solvent is evaporated off under vacuum. 23.7 g of the expected product are obtained.

B) 1-tert-butoxycarbonyl-4-isocyanato-4-phenyl-piperidine.

A solution of 25 g of the compound obtained in the preceding step and 10.35 g of triethylamine in 100 ml of acetone is cooled to 0–5° C., a solution of 8.7 g of methyl chloroformate in 30 ml of acetone is added dropwise at a temperature below 5° C., and the mixture is left stirring for 30 minutes. A solution of 10.66 g of sodium azide in 30 ml of water is then added at a temperature below 5° C., and the reaction mixture is left stirring for 30 minutes. It is poured into 500 ml of ice-cold water and extracted four times with 130 ml of toluene, and the combined organic phases are washed twice with a pH 2 buffer solution and with saturated NaCl solution, dried over MgSO$_4$ and filtered. The filtrate is heated to 90° C. for 1 hour and then concentrated under vacuum. 18.9 g of the expected product are obtained in the form of an oil.

C) 4-(Methoxycarbonylamino)-4-phenylpiperidine p-toluenesulphonate hemihydrate.

A solution of 6.05 g of the compound obtained in the preceding step in 100 ml of MeOH is heated to reflux for 5 hours. 1 drop of triethylamine is added and the mixture is left stirring overnight at RT. Concentrated HCl solution is then added to pH 1 and the reaction mixture is concentrated under vacuum. The residue is taken up with 10% NaOH solution, the product is extracted with DCM, the organic phase is washed with 10% NaOH solution and with saturated NaCl solution and dried over MgSO$_4$ and the solvent is evaporated off under vacuum. The product obtained is dissolved in acetone, a solution of 3.57 g of p-toluenesulphonic acid monohydrate in 10 ml of acetone is added dropwise and the mixture is concentrated under vacuum. The product obtained is taken up in ether and the solvent is evaporated off under vacuum. 7.17 g of the expected product are obtained, m.p.=159° C.

PREPARATION 1.6

4-(Ethoxycarbonylamino)-4-phenylpiperidine trifluoroacetate

A) 1-(tert-butoxycarbonyl-4-(ethoxycarbonylamino)-4-phenylpiperidine.

A solution of 6.28 g of the compound obtained in step B of PREPARATION 1.5 in 100 ml of EtOH is heated to reflux for 5 hours 30 minutes. A drop a triethylamine is added, and the reaction mixture is then left stirring overnight at RT and concentrated under vacuum. 7.25 g of the expected product are obtained, which is used without further treatment.

B) 4-(Ethoxycarbonylamino)-4-phenylpiperidine trifluoroacetate.

A solution of 7.25 g of the compound obtained in the preceding step in 20 ml of TFA is left stirring for 5 minutes at RT and concentrated under vacuum. The residue is taken up in acetone and the solvent is evaporated off under vacuum. The oil obtained is dissolved in a minimum of acetone, ether is added until precipitation takes place and the mixture is left stirring overnight at RT. 6.02 g of the expected product are obtained after draining and drying, m.p.=173° C.

PREPARATION 1.7

4-(Methanesulphonamido)-4-phenylpiperidine p-toluenesulphonate.

A) 1-Benzyl-4-(methanesulphonamido)-4-phenylpiperidine.

A solution of 6 g of the compound obtained in step B of PREPARATION 1.3 and 5.71 g of triethylamine in 100 ml of DCM is cooled to 0–5° C., 2.22 g of methanesulphonyl chloride are added dropwise and the mixture is left stirring for 30 minutes at RT. A further 0.2 ml of methanesulphonyl chloride is added and stirring is continued for 2 hours. The reaction mixture is concentrated under vacuum, the residue is extracted with DCM, the organic phase is washed with 10% NaOH solution, with water and with saturated NaCl solution and dried over MgSO$_4$ and the solvent is evaporated off under vacuum. 6.6 g of the expected product are obtained.

B) 4-(Methanesulphonamido)-4-phenylpiperidine p-toluenesulphonate.

A mixture of 6.6 g of the compound obtained in the preceding step, 3.64 g of p-toluenesulphonic acid monohydrate and 0.66 g of palladium on charcoal (10% Pd) in 100 ml of EtOH is hydrogenated for 6 hours in a Parr apparatus at 450C and at a pressure of 17 bars. The catalyst is filtered off and the filtrate is concentrated under vacuum. 2.08 g of the expected product are obtained after crystallization in an acetone/ether (50:50; v/v) mixture.

PREPARATION 1.8

4-(3-Ethylureido)-4-phenylpiperidine p-toluenesulphonate

A) 1-tert-Butoxycarbonyl-4-(3-ethylureido)-4-phenylpiperidine.

1.55 g of a 70% solution of ethylamine in water and diluted in 10 ml of acetone are added dropwise at RT to a solution of 6.05 g of the compound obtained in step B of PREPARATION 1.5 in 100 ml of acetone. The reaction mixture is concentrated under vacuum, the residue is extracted with AcOEt, the organic phase is washed with a pH 2 buffer solution and with saturated NaCl solution and dried over $MgSO_4$ and the solvent is evaporated off under vacuum. 5.8 g of the expected product are obtained after crystallization in ether.

B) 4-(3-Ethylureido)-4-phenylpiperidine p-toluenesulphonate.

10 ml of concentrated HCl solution are added to a solution of 5.7 g of the compound obtained in the preceding step in 60 ml of MeOH, and the reaction mixture is left stirring overnight at RT. It is concentrated under vacuum, the residue is taken up with 10% NaOH solution, the product is extracted three times with DCM, the combined organic phases are washed three times with 10% NaOH solution and with saturated NaCl solution and dried over $MgSO_4$ and the solvent is evaporated off under vacuum. The product obtained (1.7 g) is dissolved in 20 ml of an acetone/MeOH (90:10; v/v) mixture, a solution of 1.31 g of p-toluenesulphonic acid monohydrate in 5 ml of acetone is added dropwise and the crystallized product formed is drained. 1.9 g of the expected product are obtained, m.p.=225° C.

PREPARATION 1.9

4-(3-Cyclopentylureido)-4-phenylpiperidine p-toluenesulphonate

A) 1-tert-Butoxycarbonyl-4-(3-cyclopentylureido)-4-phenylpiperidine.

A solution of 2.04 g of cyclopentylamine in 10 ml of acetone is added dropwise at RT to a solution of 6.05 g of the compound obtained in step B of PREPARATION 1.5 in 100 ml of acetone. The reaction mixture is concentrated under vacuum, the residue is taken up in ether and the crystallized product formed is drained. 7.4 g of the expected product are obtained.

B) 4-(3-Cyclopentylureido)-4-phenylpiperidine p-toluenesulphonate.

15 ml of concentrated HCl solution are added to a solution of 7.33 g of the compound obtained in the preceding step in 70 ml of MeOH, and the reaction mixture is left stirring for 7 hours at RT. It is concentrated under vacuum, the residue is taken up with 10 ml of water, the mixture is alkalinized to pH 12 by adding concentrated NaOH solution, 300 ml of DCM are added and the mixture is left stirring until the gummy product has been solubilized. After settling has taken place, the aqueous phase is separated and extracted three times with 150 ml of DCM, the combined organic phases are washed with saturated NaCl solution and dried over $MgSO_4$ and the solvent is evaporated off under vacuum. The product obtained (3.8 g) is dissolved in 40 ml of an acetone/MeOH (90:10; v/v) mixture, a solution of 2.5 g of p-toluenesulphonic acid monohydrate in 10 ml of acetone is added dropwise and the crystallized product formed is drained. 4 g of the expected product are obtained, m.p.=252° C.

PREPARATION 1.10

4-(3,3-Dimethylureido)-4-phenylpiperidine p-toluenesulphonate hemihydrate

A) 1-Benzyl-4-(3,3-dimethylureido)-4-phenylpiperidine.

A solution of 1.9 g N,N-dimethylcarbamoyl chloride in 10 ml of 1,2-dichloroethane is added dropwise at RT to a solution of 6 g of the compound obtained in step B of PREPARATION 1.3 and 7.14 g of triethylamine in 50 ml of 1,2-dichloroethane, and the mixture is heated to reflux for 8 hours. A further few drops of N,N-dimethylcarbamoyl chloride are added and refluxing is continued for 3 hours. The reaction mixture is concentrated under vacuum, the residue is extracted with DCM, the organic phase is washed with water, with 10% NaOH solution, with water and with saturated NaCl solution and dried over $MgSO_4$ and the solvent is evaporated off under vacuum. The residue is chromatographed on silica, eluting with a DCM/MeOH mixture gradient from (99:1; v/v) to (96:4; v/v). 1.8 g of the expected product are obtained.

B) 4-(3,3-Dimethylureido)-4-phenylpiperidine p-toluenesulphonate hemihydrate.

A mixture of 1.8 g of the compound obtained in the preceding step, 1.11 g of p-toluenesulphonic acid monohydrate and 0.2 g of palladium on charcoal (10% Pd) in 150 ml of 95% EtOH is hydrogenated at 400 and at atmospheric pressure. The catalyst is filtered on Celite® and the filtrate is evaporated under vacuum. The residue is taken up in acetone and the solvent is evaporated off under vacuum. The product obtained is dissolved in 25 ml of acetone, this solution is added slowly to 200 ml of ether and the crystallized product formed is drained. 1.86 g of the expected product are obtained, m.p.=120–122° C.

PREPARATION 1.11

4-Benzyl-4-(3,3-dimethylureido)piperidine p-toluenesulphonate

A) 1,4-Dibenzyl-4-cyanopiperidine.

A solution of 15 9 of 4-cyanopiperidine in 250 ml of THF is cooled to −50° C., 190 ml of a 1.5M solution of lithium diisopropylamide in cyclohexane is added dropwise and the mixture is left stirring for 30 minutes at −50° C. 34 ml of benzylbromide are then added slowly and the mixture is left stirring for 3 hours while allowing the temperature to rise to RT. The reaction mixture is poured into an ice/concentrated HCl mixture, ether is added and the precipitate formed is drained and washed with water. The precipitate is taken up in water, the mixture is alkalinized to pH 12 by adding concentrated NaOH solution and extracted with ether, the organic phase is dried over $MgSO_4$ and the solvent is evaporated off under vacuum. 31.7 g of the expected product are obtained after crystallization in pentane, m.p.=92° C.

B) 1,4-Dibenzyl-4-carboxypiperidine.

A mixture of 6 g of the compound obtained in the preceding step, 25 ml of $H_2SO_4$, 25 ml of AcOH and 25 ml of water is heated to 140° C. for 5 hours. The reaction mixture is poured onto ice, concentrated NaOH solution is added until the pH=6.5 and the mixture is left stirring until the product has crystallized. The crystals formed are drained, washed with water and dried. 5.2 g of the expected product are obtained after recrystallization in MeOH, m.p.= 262° C.

C) 1.4-Dibenzyl-4-(3,3-dimethylureido)piperidine.

0.4 g of phosphorus pentachloride is added at RT to a solution of 0.5 g of the compound obtained in the preceding step in 10 ml of chloroform, and the reaction mixture is heated to 60° C. for 1 hour. It is concentrated under vacuum, the residue is dissolved in 5 ml of DCM, this solution is added to a solution of 0.35 g of sodium azide in 5 ml of acetone and the reaction mixture is left stirring for 2 hours at RT. It is concentrated at RT under vacuum, the residue is extracted with ether, the organic phase is washed with saturated $Na_2CO_3$ solution and with water and dried over $MgSO_4$ and the solvent is evaporated off under vacuum. The product obtained is taken up in 10 ml of toluene and the mixture is heated to reflux for 2 hours. After cooling to RT, 2 ml of a 33% solution of dimethylamine in ethanol are added, and the reaction mixture is left stirring for 15 minutes and concentrated under vacuum. 0.43 9 of the expected product is obtained after crystallization in an iso ether/pentane mixture, m.p.=131° C.

D) 4-Benzyl-4-(3,3-dimethylureido)piperidine p-toluenesulphonate.

A mixture of 0.43 g of the compound obtained in the preceding step, 0.233 g of p-toluenesulphonic acid monohydrate and 0.05 g of palladium on charcoal (10% Pd) in 10 ml of EtOH is hydrogenated at RT and at atmospheric pressure for 24 hours. The catalyst is filtered off and the filtrate is concentrated under vacuum. 0.54 g of the expected product is obtained after crystallization in acetone, m.p.= 140° C.

PREPARATION 1.12

4-(3,3-Diethylureido)-4-phenylpiperidine p-toluenesulphonate hemihydrate

A) 1-tert-Butoxycarbonyl-4-(3,3-diethylureido)-4-phenylpiperidine.

A solution of 1.16 g of diethylamine in 10 ml of acetone is added dropwise at RT to a solution of 6.05 g of the compound obtained in step B of PREPARATION 1.5 in 100 ml of acetone. The reaction mixture is concentrated under vacuum, the residue is extracted with ether, the organic phase is washed with a pH 2 buffer solution and with saturated NaCl solution and dried over $MgSO_4$ and the solvent is evaporated off under vacuum. 7.2 g of the expected product are obtained.

B) 4-(3,3-Diethylureido)-4-phenylpiperidine p-toluenesulphonate hemihydrate.

15 ml of concentrated HCl solution are added to a solution of 7.1 g of the compound obtained in the preceding step in 70 ml of MeOH, and the reaction mixture is left stirring overnight at RT. It is concentrated under vacuum, the residue is taken up with 10% NaOH solution, the product is extracted three times with DCM, the combined organic phases are washed three times with 10% NaOH solution and with saturated NaCl solution and dried over $MgSO_4$ and the solvent is evaporated off under vacuum. The product obtained (5.1 g ) is dissolved in 50 ml of acetone, a solution of 3.52 g of p-toluenesulphonic acid monohydrate in 15 ml of acetone is added dropwise and the mixture is concentrated under vacuum. The residue is taken up in AcOEt, MeOH is added until the gummy product formed has dissolved and the mixture is concentrated under vacuum. The residue is taken up in ether, and the mixture is left stirring overnight at RT and concentrated under vacuum. 7.7 g of the expected product are obtained after drying, m.p.=95° C.

PREPARATION 1.13

4-Phenyl-4-(1-pyrrolidinylcarbonylamino)piperidine p-toluenesulphonate

A) 1-tert-butoxycarbonyl-4-phenyl-4-(1-pyrrolidinylcarbonylamino)piperidine.

A solution of 4.5 g of the compound obtained in step B of PREPARATION 1.5 in 60 ml of 1,2-dichloroethane is heated to reflux, 1.1 g of pyrrolidine are added and the mixture is left stirring overnight while allowing the temperature to fall to RT. The reaction mixture is concentrated under vacuum, the residue is extracted with ether, the organic phase is washed with a pH 2 buffer solution, with water, with 5% $NaHCO_3$ solution, with water and with saturated NaCl solution and dried over $MgSO_4$ and solvent is evaporated off under vacuum. 4.4 g of the expected product are obtained in the form of an oil.

B) 4-Phenyl-4-(1-pyrrolidinylcarbonylamino)piperidine p-toluenesulphonate.

8 ml of concentrated HCl solution are added to a solution of 4.4 g of the compound obtained in the preceding step in 50 ml of MeOH, and the reaction mixture is left stirring overnight at RT. It is concentrated under vacuum, the residue is taken up in water, the mixture is alkalinized by adding 10% NaOH solution, the product is extracted with DCM, the organic phase is washed with water and with saturated NaCl solution and dried over $MgSO_4$ and the solvent is evaporated off under vacuum. The product obtained (2.78 g) is dissolved in 50 ml of acetone, 1.42 g of p-toluenesulphonic acid monohydrate are added and the mixture is concentrated under vacuum. 3.85 g of the expected product are obtained after crystallization in AcOEt.

PREPARATION 1.14

4-(N-Methylcarbamoyl)-4-phenylpiperidine

A) 1-tert-Butoxycarbonyl-4-(N-methylcarbamoyl)-4-phenylpiperidine.

5.29 g of triethylamine and then 1.32 g of methylamine hydrochloride are added to a solution of 4 g of the compound obtained in step A of PREPARATION 1.5 in 20 ml of a DCM/DMF (50:50; v/v) mixture, the resulting mixture is cooled to 0–5° C., 6.37 g of BOP are added and the reaction mixture is left stirring for 24 hours at RT. It is concentrated under vacuum, the residue is extracted with ether, the organic phase is washed with water, with a pH 2 buffer solution, with water, with 10% NaOH solution, with water and with saturated NaCl solution and dried over $MgSO_4$ and the solvent is evaporated off under vacuum. 3.72 g of the expected product are obtained.

B) 4-(N-methylcarbamoyl)-4-phenylpiperidine.

8 ml of concentrated HCl solution are added to a solution of 3.7 g of the compound obtained in the preceding step in 60 ml of MeOH, and the mixture is left stirring for 1 hour at RT. It is concentrated under vacuum, the residue is taken up with 10% NaOH solution, the product is extracted with DCM, the organic phase is washed with saturated NaCl solution and dried over $MgSO_4$ and the solvent is evaporated off under vacuum. 1.95 g of the expected product are obtained.

PREPARATION 1.15

4-(Ethylaminocarbonyloxymethyl)-4-phenylpiperidine hydrochloride

A) 4-Methoxycarbonyl-4-phenylpiperidine p-toluenesulphonate.

1 g of p-toluenesulphonic acid monohydrate is added to a solution of 10 g of 4-carboxy-4-phenyl-piperidine p-toluenesulphonate in 300 ml of MeOH, and the reaction mixture is heated to reflux for 3 days. It is concentrated under vacuum, the residue is taken up in acetone and ether is added until precipitation takes place. After draining of the precipitate formed, 9.34 g of the expected product are obtained.

B) 4-Hydroxymethyl-4-phenylpiperidine.

A suspension of 1.16 g of lithium aluminium hydride in 50 ml of THF is cooled to −20° C., 4 g of the compound obtained in the preceding step are added and the mixture is left stirring overnight while allowing the temperature to rise to RT. The mixture is hydrolysed by adding 1.2 ml of water, then 2.5 ml of 10% NaOH solution and 2.5 ml of water. It is diluted with ether, the inorganic salts are filtered off and the filtrate is evaporated under vacuum. 1.8 g of the expected product are obtained.

C) 1-tert-Butoxycarbonyl-4-(hydroxymethyl)-4-phenylpiperidine.

26.05 g of di-tert-butyl dicarbonate are added to a solution of 22.8 g of the compound obtained in the preceding step in 250 ml of 1,2-dimethoxyethane, and the reaction mixture is heated to reflux for 2 hours. It is concentrated under vacuum, the residue is taken up in DCM, the organic phase is washed with a pH 2 buffer solution and with saturated NaCl solution and dried over $MgSO_4$ and the solvent is evaporated off under vacuum. 17.86 g of the expected product are obtained after crystallization in ether, m.p.=134° C.

D) 1-tert-Butoxycarbonyl-4-(ethylaminocarbonyloxymethyl)-4-phenylpiperidine.

A mixture of 2.91 g of the compound obtained in the preceding step, 2.4 g of ethyl isocyanate and 2 drops of triethylamine in 30 ml of toluene is left stirring overnight at RT. The reaction mixture is then heated to 100° C. for 24 hours and concentrated under vacuum. The residue is taken up in ether, the organic phase is washed with a pH 2 buffer solution and with saturated NaCl solution and dried over $MgSO_4$ and the solvent is evaporated off under vacuum. 3.85 g of the expected product are obtained in the form of an oil.

E) 4-(Ethylaminocarbonyloxymethyl)-4-phenylpiperidine hydrochloride.

10 ml of concentrated HCl are added to a solution of 3.85 g of the compound obtained in the preceding step in 50 ml of MeOH, and the mixture is heated to 60° C. for 2 hours. It is concentrated under vacuum, the residue is taken up in acetone and the solvent is evaporated off under vacuum. 2.6 g of the expected product are obtained after crystallization in an AcOEt/ether mixture, m.p.=240–242° C.

PREPARATION 1.16

4-(Acryloyl-N-methylamino)-4-phenylpiperidine hydrochloride

A) 4-(Acryloyl-N-methylamino)-1-benzyl-4-phenylpiperidine.

A solution of 1.5 g of the compound obtained in step B of PREPARATION 1.4 and 1.5 ml of triethylamine in 40 ml of DCM is cooled to 0–5° C., 0.5 ml of acryloyl chloride is added dropwise and the mixture is left stirring while allowing the temperature to rise to RT. The reaction mixture is poured into water, the organic phase is separated after settling has taken place and washed with water and with 2N NaOH solution and dried over $MgSO_4$ and the solvent is evaporated off under vacuum. 1.3 g of the expected product are obtained after crystallization in an ether/pentane mixture.

B) 4-(Acryloyl-N-methylamino)-4-phenylpiperidine hydrochloride.

A solution of 1.3 g of the compound obtained in the preceding step in 30 ml of 1,2-dichloroethane is cooled to 0° C., 0.5 ml of 1-chloroethyl chloroformate is added dropwise and the reaction mixture is then heated to reflux for 2 hours. It is concentrated under vacuum, the residue is taken up in 15 ml of MeOH, and the mixture is heated to reflux for 30 minutes and concentrated under vacuum. 0.65 g of the expected product is obtained after crystallization in AcOET.

PREPARATION 1.17

4-Phenyl-4-(propionyl-N-methylamino)piperidine p-toluenesulphonate

A) 4-(Acryloyl-N-methylamino)-1-benzyl-4-phenyl-piperidine p-toluenesulphonate.

0.59 g of p-toluenesulphonic acid monohydrate is added to a solution of 1.15 g of the compound obtained in step A of PREPARATION 1.16 in 10 ml of DCM, and the mixture is left for crystallization to take place. 1.65 g of the expected product are obtained.

B) 4-Phenyl-4-(propionyl-N-methylamino)piperidine p-toluenesulphonate.

A mixture of 1.64 g of the compound obtained in the preceding step and 0.2 g of palladium on charcoal (10% Pd) in 100 ml of EtOH is hydrogenated at RT and at atmospheric pressure. The catalyst is filtered off on Celite® and the solvent is evaporated off under vacuum. 1.3 g of the expected product are obtained.

PREPARATION 1.18

4-(Cyclopropylcarbonylamino)-4-phenylpiperidine hydrochloride

A) 1-Benzyl-4-(cyclopropylcarbonylamino)-4-phenylpiperidine.

A solution of 1 g of the compound obtained in step B of PREPARATION 1.3 and 1.7 ml of triethylamine in 30 ml of DCM is cooled to −20° C., 0.22 ml of cyclopropanecarbonyl chloride is added dropwise and the mixture is left stirring while allowing the temperature to rise to RT. The reaction mixture is extracted with DCM, the organic phase is washed twice with water and with 0.5N NaOH solution and dried over $MgSO_4$ and the solvent is evaporated off under vacuum. The residue is taken up in AcOEt, and the crystals formed are drained and washed with AcOEt and then with ether. 0.77 g of the expected product is obtained.

45

B) 4-(Cyclopropylcarbonylamino)-4-phenylpiperidine hydrochloride.

A mixture of 0.77 g of the compound obtained in the preceding step, 0.14 g of palladium on charcoal (10% Pd) and 40 ml of EtOH is hydrogenated at 35° C. and at atmospheric pressure. The catalyst is filtered off and the filtrate is evaporated off under vacuum. The residue is taken up in DCM, and the mixture is acidified to pH 1 by adding ethereal hydrogen chloride and evaporated under vacuum. 0.6 g of the expected product is obtained.

Proton NMR spectrum at 200 MHz in DMSO-$d_6$.

δ:

0.5to 0.9 ppm: uc: 4H
 1.9 ppm: mt: 1H
 2.05 to 2.7 ppm: uc 4H
 3.0 to 3.5 ppm: uc: 4H
 7.2 to 7.6 ppm: uc: 5H
 8.6 ppm: s: 1H
 9.0 ppm: s: 2H

PREPARATION 1.19

4-(Cyclobutylcarbonylamino)-4-phenylpiperidine p-toluenesulphonate

A) 1-Benzyl-4-(cyclobutylcarbonylamino)-4-phenylpiperidine p-toluenesulphonate.

A solution of 1.5 g of the compound obtained in step B of PREPARATION 1.3 and 2.1 ml of triethylamine in 30 ml of DCM is cooled to 0° C., 0.45 ml of cyclobutanecarbonyl chloride is added dropwise and the mixture is left stirring while allowing the temperature to rise to RT. The mixture is extracted with DCM, the organic phase is washed twice with water and with 0.5N NaOH solution and dried over $MgSO_4$ and the solvent is evaporated off under vacuum. The product obtained is dissolved in DCM, 0.6 g of p-toluenesulphonic acid monohydrate is added and the mixture is left for crystallization to take place. 1.7 g of the expected product are obtained.

B) 4-(Cyclobutylcarbonylamino)-4-phenylpiperidine p-toluenesulphonate.

A mixture of 1.69 g of the compound obtained in the preceding step, 0.2 g of palladium on charcoal (10% Pd) and 100 ml of EtOH is hydrogenated at 35° C. and at atmospheric pressure. The catalyst is filtered off on Celite® and the filtrate is evaporated under vacuum. 1.35 g of the expected product are obtained.

PREPARATION 1.20

4-(Cyclohexylcarbonyl-N-methylamino)-4-phenylpiperidine p-toluenesulphonate

A) 1-Benzyl-4-(cyclohexylcarbonyl-N-methylamino)-4-phenylpiperidine p-toluenesulphonate.

0.78 ml of cyclohexanecarbonyl chloride is added dropwise at RT to a solution of 1.5 g of the compound obtained in step B of PREPARATION 1.4 and 1.5 ml of triethylamine in 15 ml of DCM, and the reaction mixture is left stirring for 2 hours. It is washed twice with water and with 2N NaOH solution, the organic phase is dried over $MgSO_4$ and the solvent is evaporated off under vacuum. The residue is dissolved in DCM, 0.97 g of p-toluenesulphonic acid monohydrate is added and the mixture is concentrated under vacuum. 3.3 g of the expected product are obtained after crystallization in an AcOEt/ether mixture.

46

B) 4-(Cyclohexylcarbonyl-N-methylamino)-4-phenylpiperidine p-toluenesulphonate.

A mixture of 3.3 g of the compound obtained in the preceding step and 0.35 g of palladium on charcoal (10% Pd) in 100 ml of EtOH is hydrogenated at RT and at atmospheric pressure. The catalyst is filtered off and the filtrate is evaporated under vacuum. The residue is taken up in acetone and the solvent is evaporated off under vacuum. 2.2 g of the expected product are obtained after crystallization in an AcOEt/ether mixture, m.p.=160° C.

PREPARATION 1.21

4-Phenyl-4-(1-pyrrolidinylcarbonyl)piperidine hemihydrate

A) 1-tert-Butoxycarbonyl-4-carboxy-4-phenylpiperidine.

30 ml of water and 32.9 g of $K_2CO_3$ are added to a mixture of 30 g of 4-carboxy-4-phenylpiperidine p-toluenesulphonate in 300 ml of dioxane, the mixture is then heated to 60° C. and 18.2 g of di-tert-butyl dicarbonate are added dropwise. The mixture is thereafter heated for 2 hours to 60° C. and then for 30 minutes to reflux. After cooling to RT, the reaction mixture is concentrated under vacuum, the residue is extracted with DCM, the organic phase is washed with a pH 2 buffer solution, acidified to pH 4 by adding 2N HCl, washed with a pH 2 buffer solution, with water and with saturated NaCl solution and dried over $MgSO_4$ and the solvent is evaporated off under vacuum. 23.7 g of the expected product are obtained.

B) 1-tert-Butoxycarbonyl-4-(1-pyrrolidinylcarbonyl)-4-phenylpiperidine.

9.29 g of triethylamine and then 3.27 g of pyrrolidine are added to a solution of 14 g of the compound obtained in the preceding step in 200 ml of DCM. The mixture is cooled in an ice bath, 22.4 g of BOP are added and the mixture is left stirring while allowing the temperature to rise to RT. The reaction mixture is concentrated under vacuum, the residue is extracted with DCM, the organic phase is washed with water, three times with 10% NaOH solution, with water, three times with a pH 2 buffer solution, with water and with saturated NaCl solution and dried over $MgSO_4$ and the solvent is evaporated off under vacuum. 16.4 g of the expected product are obtained.

C) 4-Phenyl-4-(1-pyrrolidinylcarbonyl)piperidine hemihydrate.

Concentrated HCl solution is added to a solution of 16.4 g of the compound obtained in the preceding step in 200 ml of MeOH until the pH=1, and the reaction mixture is left stirring for 5 hours at RT. It is concentrated under vacuum, the residue is taken up in acetone and the solvent is evaporated off under vacuum. A white solid is obtained, which is recrystallized in 2-propanol. The product obtained is taken up with 10% NaOH solution, the mixture is extracted with DCM, the organic phase is washed with 10% NaOH solution and with saturated NaCl solution and dried over $MgSO_4$ and the solvent is evaporated off under vacuum. 7 g of the expected product are obtained after crystallization in ether, m.p.=126° C.

PREPARATION 1.22

4-(Carboxymethyl)-4-phenylpiperidine hydrobromide

The preparation of this compound is described in Chem. Ber., 1975, 108, 3475–3482.

PREPARATION 1.23

4-(N,N-Dimethylcarbamoyl)-4-phenylpiperidine

A) 1-tert-Butoxycarbonyl-4-(N,N-dimethylcarbamoyl)-4-phenylpiperidine.

8.1 g of triethylamine and then 4.9 g of dimethylamine hydrochloride are added to a solution of 6.11 g of the compound obtained in step A of PREPARATION 1.21 in 20 ml of DCM and 20 ml of DMF. The mixture is cooled in an ice bath, 9.73 g of BOP are added and the mixture is left stirring for 3 hours while allowing the temperature to rise to RT. The mixture is concentrated under vacuum, the residue is extracted with ether, the organic phase is washed with water, with a pH 2 buffer solution, with 10% NaOH solution, with water and with saturated NaCl solution and dried over $MgSO_4$ and the solvent is evaporated off under vacuum. 6.45 g of the expected product are obtained.

B) 4-(N,N-Dimethylcarbamoyl)-4-phenylpiperidine.

Concentrated HCl solution is added to a solution of 6.4 g of the compound obtained in the preceding step in 80 ml of MeOH until the pH=1, and the mixture is left stirring for 4 hours at RT. It is concentrated under vacuum, the residue is extracted with DCM, the organic phase is washed three times with 10% NaOH solution and with saturated NaCl solution and dried over $MgSO_4$ and the solvent is evaporated off under vacuum. 3.2 g of the expected product are obtained after crystallization in ether, m.p.=95° C.

PREPARATION 1.24

4-(2-Hydroxyethyl)-4-phenylpiperidine

A) 4-(Ethoxycarbonylmethyl)-4-phenylpiperidine.

A mixture of 16 g of the compound obtained in PREPARATION 1.22 and a few drops of $H_2SO_4$ in 200 ml of EtOH is heated to reflux for 8 hours. The mixture is concentrated under vacuum, the residue is taken up in water, the aqueous phase is neutralized by adding $Na_2CO_3$ and extracted with ether, the organic phase is washed with water and dried over $Na_2SO_4$ and the solvent is evaporated off under vacuum. 7 g of the expected product are obtained.

B) 4-(Ethoxycarbonylmethyl)-4-phenyl-1-trityl-piperidine.

A solution of 7 g of the compound obtained in the preceding step and 5 ml of triethylamine in 100 ml of DCM is cooled to 0° C., 8.9 g of trityl chloride are added slowly and the mixture is left stirring while allowing the temperature to rise to RT. The mixture is concentrated under vacuum, the residue is extracted with ether, the organic phase is washed with water and with a pH 2 buffer solution and dried over $Na_2SO_4$ and the solvent is evaporated off under vacuum. 10 g of the expected product are obtained after solidification in an iso ether/pentane mixture, m.p.=120° C.

C) 4-(2-Hydroxyethyl)-4-phenyl-1-tritylpiperidine.

A suspension of 1.5 g of lithium aluminium hydride in 50 ml of THF is cooled to 0° C., a solution of 10 g of the compound obtained in the preceding step in 80 ml of THF is added slowly and the mixture is left stirring while allowing the temperature to rise to RT. The mixture is hydrolysed by adding 10 ml of water dropwise, the inorganic salts are filtered off and the filtrate is concentrated under vacuum. 8.5 g of the expected product are obtained.

D) 4-(2-Hydroxyethyl)-4-phenylpiperidine.

A mixture of 8.5 g of the compound obtained in the preceding step, 40 ml of formic acid and 40 ml of water is heated to 60° C. for 1 hour. The insoluble matter is filtered off and the filtrate is concentrated under vacuum. The residue is taken up in water and neutralized by adding concentrated NaOH solution, the mixture is extracted with DCM, the organic phase is washed with water and dried over $Na_2SO_4$ and the solvents are evaporated off under vacuum. The residue is taken up in DCM, ethereal hydrogen chloride is added until the pH 1 and the solvents are evaporated off under vacuum. The residue is taken up in water, the aqueous phase is washed with ether, neutralized by adding concentrated NaOH and extracted with DCM, the organic phase is washed with water and dried over $Na_2SO_4$ and the solvent is evaporated off under vacuum. 2.5 g of the expected product are obtained.

PREPARATION 1.25

4-(2-Amino-4-thiazolyl)-4-phenylpiperidine p-toluenesulphonate monohydrate.

A) 4-(2-Bromoacetyl)-4-phenylpiperidine hydrobromide.

8 g of bromine are added rapidly at RT to a suspension of 11.98 g of 4-acetyl-4-phenylpiperidine hydrochloride in 200 ml of DCM, and the reaction mixture is left stirring overnight at RT. It is diluted by adding 200 ml of ether, and the precipitate formed is drained and washed with ether. 17.88 g of the expected product are obtained after drying under vacuum.

B) 4-(2-Amino-4-thiazolyl)-4-phenylpiperidine p-toluenesulphonate monohydrate.

A mixture of 7.26 g of the compound obtained in the preceding step and 1.52 g of thiourea in 1SO ml of EtOH is heated to reflux for 3 hours. The reaction mixture is concentrated under vacuum, the residue is taken up with water, the mixture is alkalinized to pH 13 by adding 10% NaOH solution, and the precipitate formed is drained and washed with water and then with ether. 4.46 g of the expected product are obtained in free base form after recrystallization in EtOH. 1 g of the base is dissolved in acetone, and 0.73 g of p-toluenesulphonic acid monohydrate is added. 1.5 g of the crystallized expected product are obtained, m.p.= 220–222° C.

PREPARATION 1.26

4-[2-(Diethylamino)-4-thiazolyl]-4-phenylpiperidine p-toluenesulphonate.

A) 1,1-Diethylthiourea.

A solution of 10.67 g of potassium thiocyanate in 100 ml of acetone is cooled in an ice bath, a solution of 12.06 g of pivaloyl chloride in 30 ml of acetone is added dropwise and the mixture is left stirring for 30 minutes while allowing the temperature to rise to RT. The reaction mixture is cooled in an ice bath, a solution of 7.3 g of diethylamine in 30 ml of acetone is added dropwise and the mixture is left stirring while the temperature to rise to RT. The mixture is concentrated under vacuum, the residue is taken up in ether, the organic phase is washed twice with water and with saturated NaCl solution and dried over MgSO$_4$ and the solvent is evaporated off under vacuum. The product obtained is taken up in 50 ml of concentrated HCl solution and the mixture is heated to 100° C. for 1 hour. After cooling to RT, the mixture is washed twice with ether, the aqueous phase is alkalinized to pH 9 by adding 30% NaOH solution and extracted three times with DCM, the organic phase is washed twice with 10% NaOH solution and with saturated NaCl solution and dried over MgSO$_4$ and the solvent is evaporated off under vacuum. The residue is taken up in ether and the precipitate formed is drained. 9.44 g of the expected product are obtained.

B) 4-[2-(Diethylamino)-4-thiazolyl]-4-phenylpiperidine p-toluenesulphonate.

A mixture of 7.26 g of the compound obtained in step A of PREPARATION 1.25 and 2.64 g of the compound obtained in the preceding step in 150 ml of EtOH is heated to reflux for 2 hours. The mixture is concentrated under vacuum, the residue is taken up in water, the mixture is alkalinized to pH 12 by adding 10% NaOH solution and extracted twice with ether, the organic phase is washed with 10% NaOH and with saturated NaCl solution and dried over MgSO$_4$ and the solvent is evaporated off under vacuum. 5.7 g of the product are obtained in free base form. The base is dissolved in acetone, a solution of 3.44 g of p-toluenesulphonic acid monohydrate in 10 ml of acetone is added dropwise and the crystallized product formed is drained. 7.6 g of the expected product are obtained, m.p.= 205–206° C.

PREPARATION 1.27

4-[2-(Dimethylamino)-4-thiazolyl]-4-phenylpiperidine p-toluenesulphonate

A) 1,1-Dimethylthiourea.

This compound is prepared according to the procedure described in step A of PREPARATION 1.26, from 10.67 g of potassium thiocyanate, 12.06 g of pivaloyl chloride and 4.51 g of dimethylamine. 6.7 g of the expected product are obtained.

B) 4-[2-(Dimethylamino)-4-thiazolyl]-4-phenylpiperidine p-toluenesulphonate.

This compound is prepared according to the procedure described in step B of PREPARATION 1.26, from 7.26 g of the compound obtained in step A of PREPARATION 1.25 and 2.08 g of the compound obtained in the preceding step in 150 ml of EtOH. 6.1 g of the expected product are obtained.

PREPARATION 1.28

4-(2-Amino-1,3,4-oxadiazol-5-yl)-4-phenylpiperidine p-toluenesulphonate

A) 1-(Benzyloxycarbonyl)-4-carboxy-4-phenylpiperidine.

A mixture of 37.7 g of 4-carboxy-4-phenylpiperidine p-toluenesulphonate, 53.3 g of 30% aqueous NaOH solution and 250 ml of water is cooled to 5° C. A solution of 18 g of benzyl chloroformate in 60 ml of acetone is added rapidly at 5° C., and the mixture is left stirring overnight while allowing the temperature to rise to RT. The reaction mixture is washed twice with ether and, after settling has taken place, the aqueous phase is separated and acidified to pH 1 by adding concentrated HCl and then 2N HCl. The precipitate formed is drained, dried, taken up in ether and drained again. 30.6 g of the expected product are obtained, m.p.=142–144° C.

B) 1-(Benzyloxycarbonyl)-4-(chloroformyl)-4-phenylpiperidine.

A mixture of 17.1 g of the compound obtained in the preceding step and 24 g of thionyl chloride in 150 ml of 1,2-dichloroethane is heated to reflux for 1 hour. It is concentrated under vacuum, the residue is taken up in chloroform and the solvent is evaporated off under vacuum. The residue is taken up in an ether/pentane mixture and the solvents are again evaported off under vacuum. 20 g of the expected product are obtained in the form of a gum, which is used without further treatment.

C) 1-(Benzyloxycarbonyl)-4-carbazoyl-4-phenylpiperidine.

A solution of 16 g of hydrazine monohydrate in 40 ml of EtOH is cooled to –50° C., a solution of 11.44 g of the compound obtained in the preceding step in 20 ml of 1,2-dimethoxyethane is added dropwise and the mixture is left stirring while allowing the temperature to rise to RT. The mixture is concentrated under vacuum, the residue is taken up with water, the product is extracted with DCM, the organic phase is washed with water and with saturated NaCl solution and dried over MgSO$_4$ and the solvent is evaporated off under vacuum. The residue is taken up with an EtOH/benzene mixture and the solvents are evaporated off under vacuum. 11.2 g of the expected product are obtained in the form of a gum, which is used without further treatment.

D) 4-(2-Amino-1,3,4-oxadiazol-5-yl)-1-(benzyloxy-carbonyl)-4-phenylpiperidine.

A solution of 3.39 g of cyanogen bromide in 10 ml of EtOH is added at RT to a solution of 11.2 g of the compound obtained in the preceding step in 60 ml of EtOH, and the reaction mixture is heated to reflux for 1 hour. It is concentrated to 50 ml of EtOH, and water is then added dropwise until a volume of 400 ml of reaction mixture is obtained. The crystallized product formed is drained and washed with water and then with DCM, with AcOEt and with ether. 8 g of the expected product are obtained.

E) 4-(2-Amino-1,3,4-oxadiazol-5-yl)-4-phenylpiperidine p-toluenesulphonate.

A mixture of 7.85 g of the compound obtained in the preceding step, 3.95 g of p-toluenesulphonic acid monohydrate, 0.8 g of palladium on charcoal (10% Pd), 350 ml of 95% EtOH and 10 ml of water is hydrogenated at 50° C. and at atmospheric pressure. After 3 hours, the catalyst is filtered off on Celite® and the filtrate is concentrated under vacuum. The residue is taken up in acetone, and the crystallized product formed is drained and washed with acetone and then with ether. 7.65 g of the expected product are obtained, m.p.=183–1850C.

PREPARATION 1.29

4-(3,3-Dimethylcarbazoyl)-4-phenylpiperidine p-toluenesulphonate

A) 1-(Benzyloxycarbonyl)-4-(3,3-dimethylcarbazoyl)-4-phenylpiperidine p-toluenesulphonate.

A solution of 7.15 g of the compound obtained in step B of PREPARATION 1.28 in 60 ml of DCM is cooled to 5° C., a solution of 1.44 g of 1,1-dimethylhydrazine and 4.04 g of triethylamine in 20 ml of DCM is added dropwise and the reaction mixture is left stirring overnight at RT. It is concentrated under vacuum, the residue is taken up with water, the product is extracted with AcOEt, the organic phase is washed with saturated NaCl solution and dried over $Na_2SO_4$ and the solvent is evaporated off under vacuum. The product obtained is dissolved in 100 ml of acetone, a solution of 3.59 g of p-toluenesulphonic acid in 10 ml of acetone is added rapidly and the mixture is concentrated under vacuum. The residue is taken up in an ether/DCM mixture and the precipitate formed is drained. 9.65 g of the expected product are obtained.

B) 4-(3,3-Dimethylcarbazoyl)-4-phenylpiperidine p-toluene sulphonate.

A mixture of 9.5 g of the compound obtained in the preceding step and 0.9 g of palladium on charcoal (10% Pd) in 100 ml of 95% EtOH is hydrogenated at 30° C. and at atmospheric pressure. The catalyst is filtered off on Celite® and the filtrate is concentrated under vacuum. The residue is taken up in 100 ml of acetone, and the crystallized product formed is drained and washed with ether. 7 g of the expected product are obtained, m.p.=210–212° C.

PREPARATION 1.30

4-(3-Ethyl-1-methylureido)-4-phenylpiperidine p-toluenesulphonate

A) 1-Benzyl-4-(3-ethyl-1-methylureido)-4-phenylpiperidine p-toluenesulphonate.

A solution of 1.12 g of ethyl isocyanate in 5 ml of toluene is added dropwise at RT to a solution of 4.2 g of the compound obtained in step B of PREPARATION 1.4 in 25 ml of toluene, and the reaction mixture is left stirring for 1 hour at RT. It is concentrated under vacuum, the product obtained is dissolved in acetone, a solution of 2.8 g of p-toluenesulphonic acid in acetone is added dropwise and the mixture is left for crystallization to take place. 7.4 g of the expected product are obtained after draining the crystals formed.

B) 4-(3-Ethyl-1-methylureido)-4-phenylpiperidine p-toluenesulphonate.

A mixture of 7.4 g of the compound obtained in the preceding step, 0.7 g of palladium on charcoal (10% Pd) in 200 ml of EtOH and 10 ml of water is hydrogenated at 40° C. and at atmospheric pressure. The catalyst is filtered off and the filtrate is concentrated under vacuum. The residue is taken up in acetone and the solvent is evaporated off under vacuum. 5.5 g of the expected product are obtained after crystallization in AcOEt, m.p.=165–166° C.

PREPARATION 1.31

4-Amino-4-phenylpiperidine dibenzenesulphonate 26.95 g of the compound obtained in step B of PREPARATION 1.3 are dissolved in 50 ml of water, the mixture is alkalinized to pH 12 by adding concentrated NaOH solution, the product is extracted with DCM, the organic phase is washed with saturated NaCl solution and dried over $Na_2SO_4$ and the solvent is evaporated off under vacuum. The oil obtained is taken up in 300 ml of EtOH, 25 g of benzenesulphonic acid and 2.2 g of palladium on charcoal (5% Pd) are added and the mixture is then hydrogenated at 40° C. and at atmospheric pressure. The catalyst is filtered off on Celite and washed with MeOH and the filtrate is concentrated under vacuum. The residue is taken up in acetone and the precipitate formed is drained. 29.7 g of the expected product are obtained, m.p.=276–278° C.

PREPARATION 1.32

4-Benzyl-4-(ethoxycarbonylamino)piperidine p-toluene sulphonate

A) 1,4-Dibenzyl-4-isocyanatopiperidine.

A mixture of 2 g of the compound obtained in step B of PREPARATION 1.11 and 1.6 g of phosphorus pentachloride in 40 ml of chloroform is heated to 60° C. for 1 hour. The reaction mixture is concentrated under vacuum, the residue is taken up in 40 ml of acetone, a solution of 2 g of sodium azide in 5 ml of water is added and the mixture is left stirring for 30 minutes at RT. It is concentrated under vacuum at RT, the residue is taken up in ether, the organic phase is washed with saturated $Na_2CO_3$ solution and with water and dried over $MgSO_4$ and the solvent is evaporated off under vacuum. The residue is taken up in 40 ml of toluene and the mixture is heated to reflux for 1 hour. It is concentrated under vacuum, and 2 g of the expected product are obtained in the form of an oil.

B) 1,4-Dibenzyl-4-(ethoxycarbonylamino)piperidine p-toluenesulphonate.

A mixture of 1 g of the compound obtained in the preceding step and 20 ml of EtOH is heated to reflux for 24 hours. The mixture is concentrated under vacuum, the oil obtained is dissolved in 5 ml of acetone, 0.55 g of para-toluenesulphonic acid monohydrate is added and ether is then added until crystallization takes place. The crystals formed are drained, washed with ether and dried. 1.38 g of the expected product are obtained, m.p.=154° C.

C) 4-Benzyl-4-(ethoxycarbonylamino)piperidine p-toluenesulphonate.

A mixture of 1.3 g of the compound obtained in the preceding step, 0.15 g of palladium on charcoal (10% Pd) and 20 ml of EtOH is left stirring for 24 hours under a hydrogen atmosphere. The catalyst is filtered off and the filtrate is concentrated under vacuum. 1 g of the expected product is obtained in the form of a foam.

PREPARATION 1.33

4-[N-(1-Pyrrolidinyl)carbamoyl]-4-phenylpiperidine benzenesulphonate

A) 1-(benzyloxycarbonyl)-4-[N-(1-pyrrolidinyl)-carbamoyl]-4-phenylpiperidine benzenesulphonate.

A mixture of 11.54 g of the compound obtained in step A of PREPARATION 1.28 in 100 ml of 1,2-dichloroethane is heated to reflux, 16.18 g of thionyl chloride are added, refluxing is continued for 1 hour and the mixture is left stirring overnight at RT. It is concentrated under vacuum, the residue is taken up in 20 ml of DCM, the mixture is cooled to 5° C., 10.3 g of triethylamine and then 5 g of 1-aminopyrrolidine hydrochloride are added and the mixture is left stirring for 1 hour. It is concentrated under vacuum, the residue is extracted with AcOEt, the organic phase is washed with water and with saturated NaCl solution and dried over $MgSO_4$ and the solvent is evaporated off under vacuum. The residue is dissolved in acetone, ether is added until precipitation takes place and the precipitate formed is drained. The precipitate is dissolved in EtOH, 2.61 g of benzenesulphonic acid are added and the precipitate formed is drained. 9.34 g of the expected product are obtained.

B) 4-[N-(1-Pyrrolidinyl)carbamoyl]-4-phenylpiperidine benzenesulphonate.

A mixture of 9.34 g of the compound obtained in the preceding step and 1 g of palladium on charcoal (5% Pd) in 200 ml of EtOH is hydrogenated for 3 hours at 40° C. and at atmospheric pressure. The catalyst is filtered off and the filtrate is concentrated under vacuum. 6.13 g of the expected product are obtained after crystallization in an EtOH/acetone mixture.

PREPARATION 1.34

4-(3-Acetylcarbazoyl)-4-phenylpiperidine benzenesulphonate

A) 1-(Benzyloxycarbonyl)-4-(3-acetylcarbazoyl)-4-phenylpiperidine.

A mixture of 25.44 g of the compound obtained in step A of PREPARATION 1.28 and 35.7 g of thionyl chloride in 150 ml of 1,2-dichloroethane is heated to reflux for 2 hours and then concentrated under vacuum. The product obtained is dissolved in 200 ml of chloroform, the mixture is cooled to 5° C., 12.22 g of 1-acetylhydrazine are added and the mixture is left stirring while allowing the temperature to rise to RT. The mixture is concentrated under vacuum, the residue is taken up with 2N HCl solution, the mixture is extracted with AcOEt, and the precipitate formed is drained and washed with a DCM/AcOEt mixture: a first crop of the expected product is thereby obtained. After settling of the filtrate obtained above has taken place, the organic phase is separated and washed with 2N HCl solution and with saturated NaCl solution and dried over $Na_2SO_4$ and the solvents are evaporated off under vacuum. The residue is dissolved in AcOEt at 80° C. and, after cooling, ether is added, the precipitate formed is drained and a second crop of the expected product is obtained. A total of 23.06 g of the expected product is obtained.

B) 4-(3-Acetylcarbazoyl)-4-phenylpiperidine benzenesulphonate.

This compound is prepared according to the procedure described in step B of PREPARATION 1.33, from 2.61 g of the compound obtained in the preceding step, 1.04 g of benzenesulphonic acid, 0.3 g of palladium on charcoal (5% Pd) and 70 ml of EtOH. 2.39 g of the expected product are obtaiend after crystallization in an EtOH/ether mixture.

PREPARATION 1.35

4-(2-Methyl-1,3,4-oxadiazol-5-yl)-4-phenylpiperidine benzenesulphonate

A) 1-(Benzyloxycarbonyl)-4-(2-methyl-1,3,4-oxadiazol-5-yl)-4-phenylpiperidine.

A mixture of 22.3 g of the compound obtained in step A of PREPARATION 1.34 and 0.75 g of p-toluenesulphonic acid monohydrate in 300 ml of toluene is heated to reflux for 8 hours. The mixture is concentrated under vacuum, the residue is taken up with 5% $NaHCO_3$ solution, the product is extracted with AcOEt, the organic phase is washed with water and with saturated NaCl solution and dried over $Na_2SO_4$ and the solvent is evaporated off under vacuum. The residue is taken up in hot AcOEt, some insoluble matter is filtered off, the filtrate is left overnight at RT and diluted with ether and the precipitate formed is drained. 15.24 g of the expected product are obtained.

B) 4-(2-Methyl-1,3,4-oxadiazol-5-yl)-4-phenylpiperidine benzenesulphonate.

A mixture of 13.2 g of the compound obtained in the preceding step, 5.53 g of benzenesulphonic acid and 1.3 g of palladium on charcoal (5% Pd) in 300 ml of EtOH is hydrogenated at 40° C. and at atmospheric pressure. The catalyst is filtered off and the filtrate is concentrated under vacuum. 13.5 g of the expected product are obtained after crystallization in an acetone/AcOEt/ether mixture.

PREPARATION 2.1

2-(3,4-Dichlorophenyl)-4-hydroxybutylamine, (+) isomer

The preparation of this compound is described in Patent Application EP-A-0612716.

PREPARATION 2.2

2-(3,4-Dichlorophenyl)-4-(tetrahydro-2-pyranyloxy)-butylamine

A) 2-(3,4-Dichlorophenyl)-4-(tetrahydro-2-pyranyloxy)-butanenitrile.

A solution of 100 g of 3,4-dichlorophenylacetonitrile in 500 ml of THF is added dropwise at 20° C. over 30 minutes to a suspension of 16.5 g of sodium hydride in 200 ml of dry THF, and the reaction mixture is then stirred at RT for 2 hours. It is cooled to −20° C., a solution of 118 g of 1-bromo-2-(tetrahydro-2-pyranyloxy)ethane in 100 ml of THF is added and the mixture is left stirring for 2 hours while allowing the temperature to rise to RT. A solution of 50 g of ammonium chloride in 3 litres of water is then added, the product is extracted with 1.5 litres of ether, and the organic phase is washed with saturated sodium chloride solution, dried over magnesium sulphate and evaporated under vacuum. The residue is chromatographed on silica, eluting with DCM and then with a DCM/AcOEt (95:5; v/v) mixture. 118 g of the expected product are obtained in the form of an oil.

B) 2-(3,4-Dichlorophenyl)-4-(tetrahydro-2-pyranyloxy)-butylamine.

300 ml of concentrated aqueous ammonia are added to a solution of 118 g of nitrile obtained above in 700 ml of absolute EtOH, and Raney® nickel (10% of the amount of starting nitrile) is then introduced under a nitrogen atmosphere. The mixture is thereafter hydrogenated at RT and under pressure from a column of water. The catalyst is filtered off on Celite® and the filtrate is evaporated under vacuum. The residue is taken up with saturated sodium chloride solution, the product is extracted with ether, the organic phase is dried over magnesium sulphate and the solvent is evaporated off under vacuum. 112 g of the expected product are obtained in the form of an oil.

PREPARATION 2.3

N-Methyl-2-(3,4-dichlorophenyl)-4-tetrahydro-2-pyranyloxy)butylamine hydrochloride.

A) 2-(3,4-Dichlorophenyl)-4-hydroxybutylamine.

80 ml of a saturated solution of hydrochloric acid in ether are added to a solution of 81 g of the compound obtained in step B of PREPARATION 2.2 in 38 ml of MeOH while the temperature is maintained at between 20 and 25® C. The reaction mixture is left stirring at RT for 30 minutes and evaporated under vacuum. The residue is dissolved in 250 ml of water, the mixture is washed twice with ether, the aqueous phase is alkanilized by adding 1N NaOH solution, the product is extracted with DCM, the organic phase is dried over magnesium sulphate and the solvent is evaporated off under vacuum. The residue is taken up in 800 ml of iso ether, the insoluble matter is filtered off on Celite and the filtrate is concentrated under vacuum to approximately 300 ml. The solution is inoculated with crystals of the expected amino alcohol and stirred overnight, and the precipitate formed is filtered off and washed with iso ether and then with n-pentane. 30.2 g of the expected product are obtained, m.p.=90–91° C.

B) N-tert-Butoxycarbonyl-2-(3,4-dichlorophenyl)-4-hydroxybutylamine.

A solution of 48.96 g of di-tert-butyldicarbonate in 100 ml of AcOEt is added dropwise to a suspension of 50 g of the compound obtained in the preceding step in 250 ml of AcOEt, and the reaction mixture is heated to reflux for 30 minutes. It is washed twice with pH 2 buffer, with water and with saturated sodium chloride solution and dried over magnesium sulphate and the solvent is evaporated off under vacuum. 72.79 g of the expected product are obtained in the form of an oil, which crystallizes in hexane.

C) N-Methyl-2-(3,4-dichlorophenyl)-4-hydroxybutylamine hydrochloride.

A solution of 21.99 g of the compound obtained in the preceding step in 150 ml of THF is added dropwise to a suspension of 10 g of lithium aluminium hydride in 150 ml of anhydrous THF, and the reaction mixture is heated to reflux for 7 hours. It is then diluted with 300 ml of THF, 10 ml of water, 10 ml of 4N NaOH solution and 30 ml of water are added slowly and the mixture is left stirring for 1 hour. The inorganic salts are filtered off on Celite ®, the filtrate is allowed to settle and the organic phase is separated and evaporated under vacuum. The residue is taken up in acetone, a saturated solution of hydrochloric acid in ether is added to pH 1, the mixture is left stirring for 1 hour, and the crystals formed are filtered off and washed with acetone and then with ether. 13.49 g of the expected product are obtained, m.p.=149° C.

D) N-Methyl-2-(3,4-dichlorophenyl)4-(tetrahydro-2-pyranyloxy)butylamine hydrochloride.

A mixture of 13.04 g of the compound obtained in the preceding step, 5.78 g of 3,4-dihydro-2H-pyran in 200 ml of DCM and a few drops of a saturated solution of hydrochloric acid in ether is heated to reflux for 2 hours. After cooling, the reaction mixture is evaporated under vacuum and the residue is recrystallized in the heated state in acetone. 10.66 g of the expected product are obtained, which is used without further treatment.

PREPARATION 2.4

2-(3,4-Difluorophenyl)-4-(tetrahydro-2-pyranyloxy)butylamine.

A) 2-(3,4-Difluorophenyl)-4-(tetrahydro-2-pyranyloxy)butanenitrile.

A solution of 50 g of 3,4-difluorophenyl acetonitrile in 50 ml of THF is added dropwise at 20° C. to a suspension of 14.4 g of 60% sodium hydride in oil in 250 ml of THF, and the reaction mixture is left stirring for three hours at RT. It is cooled in an ice bath, a solution of 68.2 g of 1-bromo-2-(tetrahydro-2-pyranyloxy)ethane in 50 ml of THF is added dropwise and the reaction mixture is left stirring overnight at RT. It is acidified by adding a pH 2 buffer solution, and the THF is then evaporated off under vacuum. The aqueous phase is extracted with ether, the organic phase is washed twice with a pH 4 buffer solution, with water and with saturated NaCl solution and dried over $Na_2SO_4$ and the solvent is evaporated off under vacuum. The residue is chromatographed on silica, eluting with toluene and then with a toluene/AcOEt (100:3; v/v) mixture. 50 g of the expected product are obtained.

B) 2-(3,4-Difluorophenyl)-4-(tetrahydro-2-pyranyloxy)butylamine.

A mixture of 20.7 g of the compound obtained in the preceding step, 2.1 g of Raney® nickel in 200 ml of EtOH and 50 ml of 20% aqueous ammonia solution is hydrogenated at 30° C. and at atmospheric pressure. The catalyst is filtered off on Celite® and the fitrate is concentrated under vacuum. The residue is extracted with ether, the organic phase is washed with water and with saturated NaCl solution and dried over $MgSO_4$ and the solvent is evaporated off under vacuum. 19 g of the expected product are obtained.

PREPARATION 2.5

5-(3,4-Difluorophenyl)-5-[2-(tetrahydro-2-pyranyloxy)ethyl]-2-piperidone

A) Methyl 4-cyano-4-(3,4-difluorophenyl)-6-(tetrahydro-2-pyranyloxy)hexanoate.

A mixture of 28.12 g of the compound obtained in step A of PREPARATION 2.4 and 1 ml of Triton® B in 100 ml of THF is heated to reflux, and a solution of 9.46 g of methyl acrylate in 10 ml of THF is added dropwise. After cooling to RT, the reaction mixture is concentrated under vacuum, the residue is taken up in water, the product is extracted with ether, the organic phase is washed with water, with a pH 4 buffer solution and with saturated NaCl solution and dried over $MgSO_4$ and the solvent is evaporated off under vacuum. 35 g of the expected product are obtained in the form of a red oil.

B) 5-(3,4-Difluorophenyl)-5-[2-(tetrahydro-2-pyranyloxy)ethyl]-2-piperidone.

A mixture of 35 g of the compound obtained in the preceding step, 3.5 g of Raney® nickel and 5 g of KHCO3 in 600 ml of 95% ethanol is hydrogenated in a Parr apparatus at 50° C. and at 20.4 bars pressure. The catalyst is filtered off on Celite® and the filtrate is concentrated under vacuum. The residue is extracted with AcOEt, the organic phase is washed twice with water and twice with saturated NaCl solution and dried over $MgSO_4$ and the solvent is evaporated off under vacuum. 32.1 g of the expected product are obtained in the form of a yellow oil.

PREPARATION 2.6

3-(3,4-Dichlorophenyl)-3-[2-(tetrahydro-2-pyranyloxy)ethyl]piperidine

A) Ethyl 4-cyano-4-(3,4-dichlorophenyl)-6-(tetrahydro-2-pyranyloxy)hexanoate.

A solution of 44.7 ml of a 1.5 M solution of lithium diisopropylamide/THF complex in cyclohexane diluted in 100 ml of THF is added dropwise at RT to a solution of 21 g of the compound obtained in step A of PREPARATION 2.2 in 100 ml of THF, and the mixture is left stirring for 1 hour at RT. 12 g of ethyl 3-bromopropionate are then added and the reaction mixture is heated to 50° C. for 2 hours. After cooling, it is poured into saturated ammonium chloride solution, the product is extracted with ether, the organic phase is washed with water and dried over sodium sulphate and the solvent is evaporated off under vacuum. The residue is chromatographed on silica, eluting with a DCM/AcOEt (100:1; v/v) mixture. 13 g of the expected product are obtained, which is used in the next step without further treatment.

B) 5-(3,4-Dichlorophenyl)-5-[2-(tetrahydro-2-pyranyloxy) ethyl]-2-piperidone.

40 ml of concentrated aqueous ammonia are added to a solution of 13 g of the compound obtained in the preceding step in 250 ml of EtOH, and Raney® nickel (10% of the amount of starting nitrile) is then introduced. The mixture is thereafter hydrogenated at RT and at atmospheric pressure. The catalyst is filtered off on Celite® and the filtrate is evaporated under vacuum. The residue is taken up in water, the product is extracted with ether, the organic phase is washed with water and dried over magnesium sulphate and the solvent is evaporated off under vacuum. 9 g of the expected product are obtained, which is used in the next step without further treatment.

C) 3-(3,4-Dichlorophenyl)-3-[2-(tetrahydro-2-pyranyloxy) ethyl]piperidine.

A suspension of 0.9 g of lithium aluminium hydride in 5 ml of THF is heated to 60° C., a solution of 3.9 g of the compound obtained in the preceding step in 50 ml of THF is added and the mixture is left stirring for 1 hour at 60° C. After cooling, 1 ml of water, 1 ml of 4N NaOH and 3 ml of water are added. The inorganic salts are filtered off on Celite®, the filtrate is allowed to settle and the organic phase is separated and evaporated under vacuum. The residue is taken up in ether, the organic phase is dried over magnesium sulphate and the solvent is evaporated off under vacuum. 3.4 g of the expected product are obtained, which is used without further treatment.

PREPARATION 2.7

3-(3,4-Dichlorophenyl)-3-(2-hydroxyethyl) piperidine, (−) isomer

The preparation of this compound is described in Patent Application EP-A-0591040.

EXAMPLE 1

N-[2-(3,4-Dichlorophenyl)-4-[4-(2-hydroxyethoxy)-4-phenyl-1-piperidyl]butyl]-N-methylbenzamide hydrochloride monohydrate, (−) isomer A) N-[2-(3,4-Dichlorophenyl)-4-hydroxybutyl]-N-methylbenzamide, (−) isomer.

The preparation of this compound is described in Patent Application EP-A-0474561, from the compound obtained in PREPARATION 2.1.

B) N-[4-(Benzenesulphonyloxy)-2-(3,4-dichlorophenyl)-butyl]-N-methylbenzamide, (−) isomer.

5 g of benzenesulphonyl chloride are added to a mixture of 5 g of the compound obtained in the preceding step and 3.54 g of triethylamine in 30 ml of DCM, and the mixture is left stirring for 3 hours 30 minutes at RT. A further 0.5 g of benzenesulphonyl chloride is added and stirring is continued for 1 hour 30 minutes. 30 ml of water are added to the reaction mixture, settling is allowed to take place, the organic phase is separated and washed twice with 30 ml of 1N HCl solution and with 30 ml of water and dried over MgSO$_4$ and the solvent is evaporated off under vacuum. The oil obtained is taken up in 50 ml of tert-butyl methyl ether and the mixture is left stirring overnight. 4.33 g of the expected product are obtained after draining and drying the white precipitate obtained, m.p.=93° C.

$[\alpha]_D^{20} = -13.0°$ (c = 1; MeOH).

C) N-[2-(3,4-Dichlorophenyl)-4-[4-(2-hydroxyethoxy)-4-phenyl-1-piperidyl]butyl]-N-methylbenzamide hydrochloride monohydrate, (−) isomer.

A mixture of 2.75 g of the compound obtained in the preceding step, 1.7 g of the compound obtained in PREPARATION 1.1 and 1.8 g of K$_2$CO$_3$ in 20 ml of DMF is heated to 80° C. for 2 hours. After cooling to RT, the reaction mixture is poured into water, the product is extracted with AcOEt, the organic phase is washed three times with water and dried over MgSO$_4$ and the solvent is evaporated off under vacuum. The residue is chromatographed on silica, eluting with DCM and then with a DCM/MeOH (97:3; v/v) mixture. The product obtained is dissolved in DCM, the mixture is acidified to pH 1 by adding ethereal hydrogen chloride and the precipitate formed is drained. 1.9 g of the expected product are obtained, m.p.=133–135° C.

$[\alpha]_D^{20} = -20.0°$ (c = 1; MeOH).

EXAMPLE 2

N-[4-[4-(2-Acetoxyethoxy)-4-phenyl-1-piperidyl]-2-(3,4-dichlorophenyl)butyl]-N-methylbenzamide hydrochloride hemihydrate, (−) isomer A solution of 0.6 g of the compound obtained in EXAMPLE 1 and 0.3 ml of triethylamine in 20 ml of DCM is cooled to 0–5° C., 0.08 ml of acetyl chloride is added and the mixture is left stirring while the temperature is allowed to rise to RT. The reaction mixture is concentrated under vacuum and the residue is chromatographed on silica, eluting with DCM and then with a DCM/MeOH (97:3; v/v) mixture. The product obtained is dissolved in DCM, the mixture is acidified to pH 1 by adding ethereal hydrogen chloride and the precipitate formed is drained. 0.23 g of the expected product is obtained, m.p.=95° C.

$[\alpha]_D^{20} = -30.4°$ (c = 1; MeOH).

EXAMPLE 3

N-[2-(3,4-Dichlorophenyl)-4-[4-(2-methoxyethoxy)-4-phenyl-1-piperidyl]butyl]-N-methylbenzamide hydrochloride 0.6 hydrate, (−) isomer This compound is prepared according to the procedure described in step C of EXAMPLE 1, from 0.5 g of the compound obtained in PREPARATION 1.2, 0.85 g of the compound obtained in step B of EXAMPLE 1 and 0.35 g of $K_2CO_3$ in 5 ml of DMF. 0.35 g of the expected product is obtained, m.p.=76–78° C.

$[\alpha]_D^{20} = -32.6°$ (c = 1; MeOH).

EXAMPLE 4

N-[4-[4-(Acetyl-N-methylamino)-4-phenyl-1-piperidyl]-2-(3,4-dichlorophenyl)butyl]-N-methylbenzamide hydrochloride monohydrate, (−) isomer A mixture of 1.67 g of the compound obtained in step B of EXAMPLE 1 and 1.5 g of $K_2CO_3$ in 10 ml of a DMF/acetonitrile (50:50; v/v) mixture is heated to 80° C., 1.9 g of the compound obtained in PREPARATION 1.4 are added slowly and heating is continued at 80° C. for 2 hours. After cooling, the reaction mixture is poured into water, the product is extracted with AcOEt, the organic phase is washed twice with water and with saturated NaCl solution and dried over MgSO4 and the solvent is evaporated off under vacuum. The residue is chromatographed on silica H, eluting with a DCM/MeOH mixture from (98:2; v/v) to (95:5; v/v). The product obtained is dissolved in AcOEt, ethereal hydrogen chloride is added until the pH=1 and ether is then added until precipitation takes place. 1.14 g of the expected product are obtained after draining and drying, m.p.=137–139° C.

$[\alpha]_D^{20} = -34.0°$ (c = 0,5; MeOH).

EXAMPLE 5

N-[2-(3,4-Dichlorophenyl)-4-[4-(methoxycarbonylamino)-4-phenyl-1-piperidyl]butyl]-N-methylbenzamide hydrochloride hemihydrate, (−) isomer A mixture of 1.97 g of the compound obtained in step B of EXAMPLE 1, 1.95 g of the compound obtained in PREPARATION 1.5 and 1.99 g of $K_2CO_3$ in 16 ml of a DMF/acetonitrile (50:50; v/v) mixture is heated to 100° C. for 3 hours. After cooling to RT, the reaction mixture is poured into 250 ml of water, the product is extracted three times with AcOEt, the organic phase is washed with saturated NaCl solution and dried over $MgSO_4$ and the solvent is evaporated off under vacuum. The residue is chromatographed on silica, eluting with DCM and then with DCM/MeOH (96:4; v/v) mixture. The product obtained is dissolved in AcOEt, a stream of HCl gas is bubbled through until the pH=1 and ether is then added until precipitation takes place. 1.44 g of the expected product are obtained, m.p.=149° C.

$[\alpha]_D^{20} = -32.8°$ (c = 0.5; MeOH).

EXAMPLE 6

N-[2-(3,4-Dichlorophenyl)-4-[4-(ethoxycarbonylamino)-4-phenyl-1-piperidyl]butyl]-N-methylbenzamide hydrochloride hemihydrate, (−) isomer This compound is prepared according to the procedure described in EXAMPLE 5, from 1.72 g of the compound obtained in step B of EXAMPLE 1, 1.52 g of the compound obtained in PREPARATION 1.6, 1.74 g of $K_2CO_3$ and 16 ml of a DMF/acetonitrile (50:50; v/v) mixture. 1.1 g of the expected product are obtained, m.p.=125° C.

$[\alpha]_D^{20} = -28.8°$ (c = 0.5; MeOH).

EXAMPLE 7

N-[2-(3,4-Dichlorophenyl)-4-[4-(methanesulphonamido)-4-phenyl-1-piperidyl]butyl]-N-methylbenzamide hydrochloride, (−) isomer This compound is prepared according to the procedure described in EXAMPLE 5, from 1.71 g of the compound obtained in step B of EXAMPLE 1, 1.90 g of the compound obtained in PREPARATION 1.7, 1.53 g of $K_2CO_3$ and 10 ml of a DMF/acetonitrile (50:50; v/v) mixture. 1.28 g of the expected product are obtained after crystallization in an acetone/ether mixture, m.p.=245° C.

$[\alpha]_D^{20} = -33°$ (c = 0.5; MeOH).

EXAMPLE 8

N-[2-(3,4-Dichlorophenyl)-4-[4-(3-ethylureido)-4-phenyl-1-piperidyl]butyl]-N-methylbenzamide hydrochloride hemihydrate, (−) isomer This compound is prepared according to the procedure described in EXAMPLE 5, from 1.72 g of the compound obtained in step B of EXAMPLE 1, 1.76 g of the compound obtained in PREPARATION 1.8, 1.74 g of $K_2CO_3$ and 16 ml of a DMF/acetonitrile (50:50; v/v) mixture. 1.13 g of the expected product are obtained, m.p.=135° C.

$[\alpha]_D^{20} = -30.4°$ (c = 0.5; MeOH).

EXAMPLE 9

N-[2-(3,4-Dichlorophenyl)-4-[4-(3-cyclopentylureido)-4-phenyl-1-piperidyl]butyl]-N-methylbenzamide hydrochloride monohydrate, (−) isomer This compound is prepared according to the procedure described in EXAMPLE 5, from 1.72 g of the compound obtained in step B of EXAMPLE 1, 1.93 g of the compound obtained in PREPARATION 1.9, 1.74 g of $K_2CO_3$ and 16 ml of a DMF/acetonitrile (50:50; v/v) mixture. 1.3 g of the expected product are obtained, m.p.=150° C.

$[\alpha]_D^{20} = -24.6°$ (c = 0.5; MeOH).

EXAMPLE 10

N-[2-(3,4-Dichlorophenyl)-4-[4-(3,3-dimethylureido)-4-phenyl-1-piperidyl]butyl]-N-methylbenzamide hydrochloride hemihydrate, (−) isomer This compound is prepared according to the procedure described in EXAMPLE 5, from 1.46 g of the compound obtained in step B of EXAMPLE 1, 1.6 g of the compound obtained in PREPARATION 1.10, 1.31 g of $K_2CO_3$ and 16 ml of a DMF/acetonitrile (50:50; v/v) mixture. After chromatography, the product obtained is dissolved in AcOEt, ethereal hydrogen chloride is added until the pH=1 and the crystallized product formed is drained. 0.72 g of the expected product is obtained, m.p.=175–177° C.

$[\alpha]_D^{20} = -26.8°$ ($c$ = 0.5; MeOH).

EXAMPLE 11

N-[4-[4-Benzyl-4-(3,3-dimethylureido)-1-piperidyl]-2-(3,4-dichlorophenyl)butyl]-N-methylbenzamide hydrochloride, (–) isomer A mixture of 0.5 g of the compound obtained in step B of EXAMPLE 1, 0.54 g of the compound obtained in PREPARATION 1.11 and 0.52 g of $K_2CO_3$ in 5 ml of DMF is heated to 90° C. for 2 hours 30 minutes. The reaction mixture is poured into ice-cold water, the product is extracted with AcOEt, the organic phase is washed with 1N NaOH solution and with saturated NaCl solution and dried over $MgSO_4$ and the solvent is evaporated off under vacuum. The residue is chromatographed on silica H, eluting with DCM and then with a DCM/MeOH (93:7; v/v) mixture. The product obtained is taken up in ethereal hydrogen chloride and the precipitate formed is drained. 0.45 g of the expected product is obtained, m.p.=155° C. (dec.).

$[\alpha]_D^{20} = -18.4°$ ($c$ = 0.5; MeOH).

EXAMPLE 12

N-[2-(3,4-(Dichlorophenyl)-4-[4-(3,3-diethylureido)-4-phenyl-1-piperidyl]butyl]-N-methylbenzamide hydrochloride sesquihydrate, (–) isomer This compound is prepared according to the procedure described in EXAMPLE 5, from 1.72 g of the compound obtained in step B of EXAMPLE 1, 1.88 g of the compound obtained in PREPARATION 1.12, 1.74 g of $K_2CO_3$ and 16 ml of a DMF/acetonitrile (50:50; v/v) mixture. 0.92 g of the expected product is obtained, m.p.=131° C.

$[\alpha]_D^{20} = -22.8°$ (c = 0.5; MeOH).

EXAMPLE 13

N-[2-(3,4-Dichlorophenyl)-4-[4-(phenyl)-4-(1-pyrrolidinylcarbonylamino)-1-piperidyl]butyl]-N-methylbenzamide hydrochloride hemihydrate, (–) isomer A mixture of 1.72 g of the compound obtained in step B of EXAMPLE 1, 1.86 g of the compound obtained in PREPARATION 1.13 and 1.72 g of $K_2CO_3$ in 16 ml of a DMF/acetonitrile (50:50; v/v) mixture is heated to 100° C. for 1 hour, and the reaction mixture is then left stirring overnight at RT. It is poured into 250 ml of water, and the crystallized product formed is drained and dried. The product is chromatographed on silica, eluting with a DCM/MeOH mixture from (98:2; v/v) to (96:4; v/v). The product obtained is dissolved in AcOEt, a stream of HCl gas is bubbled through until the pH=1 and the precipitate formed is drained. 1.27 g of the expected product are obtained, m.p.=178–180° C.

$[\alpha]_D^{20} = -24.4°$ (c = 0.5; MeOH).

EXAMPLE 14

N-[2-(3,4-Dichlorophenyl)-4-[4-(N-methylcarbamoyl)-4-phenyl-1-piperidyl]butyl]-N-methylbenzamide hydrochloride dihydrate, (–) isomer This compound is prepared according to the procedure described in EXAMPLE 5, from 1.25 g of the compound obtained in step B of EXAMPLE 1, 0.71 g of the compound obtained in PREPARATION 1.14 and 0.75 g of $K_2CO_3$ in 10 ml of a DMF/acetonitrile (50:50; v/v) mixture. 0.23 g of the expected product is obtained, m.p.=100–102° C.

$[\alpha]_D^{20} = -31.2°$ (c = 0.5; MeOH).

EXAMPLE 15

N-[2-(3,4-Dichlorophenyl)-4-[4-(ethylaminocarbonyloxymethyl)-4-phenyl-1-piperidyl]butyl]-N-methylbenzamide hydrochloride sesquihydrate A) N-[2-(3,4-Dichlorophenyl)-4-(tetrahydro-2-pyranyloxy)butyl]benzamide.

4.42 g of benzoyl chloride in 20 ml of DCM is added dropwise to a solution of 9.54 g of the compound obtained in PREPARATION 2.2 and 3.33 g of triethylamine in 50 ml of DCM, and the reaction mixture is left stirring for 1 hour at RT and then heated to reflux for 1 hour. It is concentrated under vacuum, the residue is taken up in water, the product is extracted with ether, the organic phase is washed with water, with 5% NaOH solution and with saturated NaCl solution and dried over $Na_2SO_4$ and the solvent is evaporated off under vacuum. The residue is chromatographed on silica, eluting with a DCM/MeOH (98:2; v/v) mixture. 8.3 g of the expected product are obtained in the form of an oil.

B) N-[2-(3,4-Dichlorophenyl)-4-hydroxybutyl]-N-methylbenzamide.

0.54 g of 55% sodium hydride in oil is added portionwise to a solution of 3.8 g of the compound obtained in the preceding step in 40 ml of THF, and the mixture is left stirring for 20 minutes at RT. 1.4 g of methyl iodide are then added dropwise and the reaction mixture is left stirring overnight at RT. It is concentrated under vacuum, the residue is taken up in water, the product is extracted with ether, the organic phase is washed with water and with saturated NaCl solution and dried over $Na_2SO_4$ and the solvent is evaporated off under vacuum. The oil obtained is dissolved in 30 ml of MeOH, 0.3 g of Amberlyst H-15 is added and the mixture is heated to reflux for 1 hour. The resin is filtered off on Celite and the filtrate is concentrated under vacuum. 2.67 g of the expected product are obtained after solidification in ether, m.p.=137–139° C.

C) N-[2-(3,4-Dichlorophenyl)-4-(methanesulphonyloxy) butyl]-N-methylbenzamide.

A solution of 5.26 g of methanesulphonyl chloride in 20 ml of DCM is added dropwise to a solution of 14.72 g of the compound obtained in the preceding step and 5.05 g of triethylamine in 150 ml of DCM, and the reaction mixture is left stirring for 1 hour at RT. It is concentrated under vacuum, the residue is taken up in water, the product is extracted with AcOEt, the organic phase is washed with saturated NaCl solution and dried over $Na_2SO_4$ and the solvent is evaporated off under vacuum. 16.24 g of the expected product are obtained after crystallization in ether, m.p.=100–102° C.

D) N-[2-(3,4-Dichlorophenyl)-4-[4-(ethylaminocarbonyloxymethyl)-4-phenyl-1-piperidyl] butyl]-N-methylbenzamide hydrochloride sesquihydrate.

A mixture of 0.23 g of the compound obtained in the preceding step, 0.17 g of the compound obtained in PREPARATION 1.15 and 0.22 g of $K_2CO_3$ in 10 ml of a DMF/acetonitrile (50:50; v/v) mixture is heated to 100° C. for 3 hours. The reaction mixture is concentrated under vacuum, the residue is taken up in water, the product is extracted with AcOEt, the organic phase is washed with water and with saturated NaCl solution and dried over $MgSO_4$ and the solvent is evaporated off under vacuum. The residue is chromatographed on silica H, eluting with DCM and then with a DCM/MeOH (96:4; v/v) mixture. The product obtained is dissolved in AcOEt, a stream of HCl gas is bubbled through until the pH=1, ether is then added and the mixture is concentrated under vacuum. 0.05 g of the expected product is obtained, m.p.=70–72° C.

EXAMPLE 16

N-[2-(3,4-Dichlorophenyl)-4-[4-(formylamino)-4-phenyl-1-piperidyl]butyl]-N-methylbenzamide hydrochloride hemihydrate 0.55 g of the compound obtained in PREPARATION 1.3 is dissolved in water, the mixture is alkalinized by adding concentrated NaOH solution, the product is extracted with DCM, the organic phase is dried over $MgSO_4$ and the solvent is evaporated off under vacuum. The product obtained is taken up in 20 ml of acetonitrile, 0.85 g of the compound obtained in step C of EXAMPLE 15 and 1 g of $K_2CO_3$ are added and the reaction mixture is heated to reflux for 2 hours 30 minutes. It is concentrated under vacuum, the residue is extracted with AcOEt, the organic phase is washed with water and with 5% NaOH solution and dried over $MgSO_4$ and the solvent is evaporated off under vacuum. The residue is chromatographed on silica H, eluting with DCM and then with a DCM/MeOH (90:10; v/v) mixture. The product obtained is taken up in ethereal hydrogen chloride and the precipitate formed is drained. 0.51 g of the expected product is obtained.

Proton NMR spectrum at 200 MHz in DMSO-$d_6$.
δ:
 1.8 to 2.65 ppm: uc: 6 H
 2.65 to 3.9 ppm: uc: 12 H
 6.8 to 7.9 ppm: uc: 13 H
 8.1 ppm: s: 1 H
 8.45 ppm: s: 1 H
 10.95 ppm: s: 1 H

EXAMPLE 17

N-[4-[4-(Acryloyl-N-methylamino]-4-phenyl-1-piperidyl]-2-(3,4-dichlorophenyl)butyl]-N-methyl-benzamide hydrochloride sesquihydrate A mixture of 0.5 g of the compound obtained in step C of EXAMPLE 15, 0.36 g of the compound obtained in PREPARATION 1.16 and 0.35 g of $K_2CO_3$ in 5 ml of DMF is heated to 80° C. for 2 hours. The reaction mixture is poured into water, the product is extracted with AcOEt, the organic phase is washed twice with water and with saturated NaCl solution and dried over $MgSO_4$ and the solvent is evaporated off under vacuum. The residue is chromatographed on silica, eluting with a DCM/MeOH mixture from (99:1; v/v) to (95:5; v/v). The product obtained is dissolved in DCM, the mixture is acidified to pH 1 by adding ethereal hydrogen chloride and the precipitate formed is drained. 0.25 g of the expected product is obtained, m.p.=120° C.

EXAMPLE 18

N-[4-[4-(Carboxymethyl)-4-phenyl-1-piperidyl]-2-(3,4-dichlorophenyl)butyl]-N-methylbenzamide hydrochloride sesquihydrate 1.8 g of potassium tert-butylate and then 1.5 g of the compound obtained in step C of EXAMPLE 15 are added to a solution of 2.3 g of the compound obtained in PREPARATION 1.22 in 20 ml of DMF, and the reaction mixture is heated to 80° C. for 2 hours. It is concentrated under vacuum, the residue is taken up in water, the mixture is neutralized to pH 7 by adding concentrated HCl solution, the product is extracted with DCM, the organic phase is washed with water and dried over $MgSO_4$ and the solvent is evaporated off under vacuum. The residue is chromatographed on silica H, eluting with a DCM/MeOH (95:5; v/v) mixture. The product obtained is taken up with ethereal hydrogen chloride and the solvent is evaporated off under vacuum. 0.96 g of the expected product is obtained after crystallization in iso ether.

Proton NMR spectrum at 200 MHz in DMSO-$d_6$.
δ:
 1.2 to 2.45 ppm: uc: 6 H
 2.5 to 3.8 ppm: uc: 14 H
 6.6 to 7.6 ppm: uc: 13 H.

EXAMPLE 19

N-[4-[4-(Carboxymethyl)-4-phenyl-1-piperidyl]-2-(3,4-dichlorophenyl)butyl]-N-methyl-2-(3-isopropoxyphenyl)acetamide hydrochloride A) N-[2-(3,4-Dichlorophenyl)-4-(tetrahydro-2-pyranyloxy) butyl]-N-methyl-2-(3-isopropoxyphenyl)acetamide.

8.78 g of triethylamine and then 5.62 g of 3-isopropoxyphenylacetic acid and 14.11 g of BOP are added to a solution of 10.66 g of the compound obtained in PREPARATION 2.3 in 100 ml of DCM. The reaction mixture is left stirring for 4 hours at RT and concentrated under vacuum. The residue is extracted with AcOEt, the mixture is washed with water, with 10% NaOH solution, with water and with saturated sodium chloride solution and dried over magnesium sulphate and the solvent is evaporated off under vacuum. The residue is chromatographed on silica, eluting with a DCM/MeOH (90:10; v/v) mixture. 13.40 g of the expected product are obtained, which is used in the next step without further treatment.

B) N-[2-(3,4-Dichlorophenyl)-4-hydroxybutyl]-N-methyl-2-(3-isopropoxyphenyl)acetamide.

A few drops of a saturated solution of hydrochloric acid in ether are added to a solution of 13.4 g of the compound obtained in the preceding step in 200 ml of MeOH, and the reaction mixture is left stirring for 1 hour at RT. It is concentrated under vacuum, the residue is taken up in MeOH and the mixture is again evaporated under vacuum. 11.70 g of the expected product are obtained, which is used in the next step without further treatment.

C) N-[2-(3,4-Dichlorophenyl)-4-(methanesulphonyloxy) butyl]-N-methyl-2-(3-isopropoxyphenyl)acetamide.

6.68 g of triethylamine are added to a solution of 11.70 g of the compound obtained in the preceding step in 100 ml of DCM, and a solution of 6.94 g of methane-sulphonyl chloride in 30 ml of DCM is then added dropwise. The reaction mixture is left stirring for 6 hours at RT and concentrated under vacuum. The residue is extracted with AcOEt, the mixture is washed with water and with saturated sodium chloride solution and dried over magnesium sulphate and the solvent is evaporated off under vacuum. The residue is chromatographed on silica, eluting with a DCM/MeOH (99:1; v/v) mixture. 13.04 g of the expected product are obtained in the form of an oil.

Proton NMR spectrum at 200 MHz in DMSO-$d_6$.
δ:

1.3 ppm: d: 6 H
2.05 ppm: mt: 2 H
2.8 ppm: sd: 3 H
3 to 4.3 ppm: uc: 10 H
4.6 ppm: sept: 1 H
6.4 to 7.9 ppm: uc: 7 H D) N-[4-[4-(Carboxymethyl)-4-phenyl-1-piperidyl]-2-(3,4-dichlorophenyl)butyl]-N-methyl-2-(3-isopropoxyphenyl) acetamide hydrochloride.

1.5 g of potassium tert-butylate and then a solution of 1.5 g of the compound obtained in the preceding step in 10 ml of DMF are added to a solution of 2 g of the compound obtained in PREPARATION 1.22 in 14 ml of DMF, and the reaction mixture is heated to 80° C. for 3 hours. It is poured into a pH 7 buffer solution, the product is extracted with DCM, the organic phase is washed with water and with 2N HCl solution and dried over MgSO$_4$ and the solvent is evaporated off under vacuum. The residue is chromatographed on silica H, eluting with a DCM/MeOH (95:5; v/v) mixture. 0.62 g of the expected product is obtained.

Proton NMR spectrum at 200 MHz in DMSO-$d_6$.
δ:

1.0 to 1.4 ppm: 2d: 6 H
1.5 to 2.45 ppm: uc: 6 H
2.5 to 3.9 ppm: uc: 16 H
4.6 ppm: sept: 1 H
6.4 to 7.8 ppm: uc: 12 H.

EXAMPLE 20

N-[2-(3,4-Difluorophenyl)-4-[4-(methoxycarbonylamino)-4-phenyl-1-piperidyl] butyl]-N-methylbenzamide hydrochloride hemihydrate A) N-[2-(3,4-Difluorophenyl)-4-(tetrahydro-2-pyranyloxy) butyl]benzamide.

A solution of 19 g of the compound obtained in PREPARATION 2.4 and 8.06 g of triethylamine in 250 ml of DCM is cooled to 0–5° C., a solution of 9.82 g of benzoyl chloride in 50 ml of DCM is added dropwise and the reaction mixture is then concentrated under vacuum. The residue is extracted with ether, the organic phase is washed with water, with 10% NaOH solution, with water and with saturated NaCl solution and dried over MgSO$_4$ and the solvent is evaporated off under vacuum. 26 g of the expected product are obtained.

B) N-[2-(3,4-Difluorophenyl)-4-(tetrahydro-2-pyranyloxy) butyl]-N-methylbenzamide.

A solution of 26 g of the compound obtained in the preceding step in 80 ml of DMF is added dropwise to a suspension of 4.4 g of 55% sodium hydride in oil in 50 ml of DMF, and the reaction mixture is left stirring for 30 minutes at RT. It is cooled in a water bath, a solution of 19 g of methyl iodide in 50 ml of DMF is added dropwise and the mixture is left stirring overnight at RT. It is concentrated under vacuum, the residue is taken up in water, the product is extracted with DCM, the organic phase is washed twice with water and with saturated NaCl solution and dried over MgSO$_4$ and the solvent is evaporated off under vacuum. 27 g of the expected product are obtained.

C) N-[2-(3,4-Difluorophenyl)-4-hydroxybutyl]-N-methylbenzamide.

A stream of HCl gas is bubbled into a solution of 27 g of the compound obtained in the preceding step in 500 ml of MeOH until the pH<1, and the mixture is left stirring for 15 minutes at RT. It is concentrated under vacuum, the residue is taken up with a saturated solution of HCl gas in MeOH and the solvent is evaporated off under vacuum. The residue is extracted with DCM, the organic phase is washed twice with 5% NaHCO$_3$ solution and with saturated NaCl solution and dried over MgSO$_4$ and the solvent is evaporated off under vacuum. 15.9 g of the expected product are obtained after solidification in cyclohexane.

D) N-[2-(3,4-Difluorophenyl)-4-(methanesulphonyloxy) butyl]-N-methylbenzamide.

A solution of 6 g of the compound obtained in the preceding step and 2.27 g of triethylamine in 200 ml of DCM is cooled to 0–5° C., a solution of 2.37 g of methanesulphonyl chloride in 20 ml of DCM is added dropwise and the reaction mixture is then concentrated under vacuum. The residue is taken up in water, the product is extracted with AcOEt, the organic phase is washed three times with water, with 5% NaHCO$_3$ solution, with water and with saturated NaCl solution and dried over MgSO$_4$ and the solvent is evaporated off under vacuum. 7.8 g of the expected product are obtained.

E) N-[2-(3,4-Difluorophenyl)-4-[4-(methoxycarbonylamino)-4-phenyl-1-piperidyl]butyl]-N-methylbenzamide hydrochloride hemihydrate.

This compound is prepared according to the procedure described in step D of Example 15, from 1.2 g of the compound obtained in the preceding step, 1.43 g of the compound obtained in PREPARATION 1.5 and 1.42 g of K$_2$CO$_3$ in 20 ml of a DMF/acetonitrile (50:50; v/v) mixture. 1.18 g of the expected product are obtained, m.p.=165° C.

By working according to the procedures described in the above EXAMPLES, starting from the piperidines described in the above PREPARATIONS, the compounds according to the invention collated in TABLE I below are prepared.

TABLE I

| EXAMPLES | Y | Ar$_1$ | Solvate; M.p. ° C. or NMR |
|---|---|---|---|
| 21 (a) | —N(Me)—C(=O)—Et | 3,4-diCl-phenyl | 1 H$_2$O; 130 |
| *22 (a) | —NH—C(=O)—cyclopropyl | 3,4-diCl-phenyl | 0.5 H$_2$O; 165 |
| 23 (a) | —NH—C(=O)—cyclobutyl | 3,4-diCl-phenyl | 1 H$_2$O; 152 |
| 24 (a) | —N(Me)—C(=O)—cyclohexyl | 3,4-diCl-phenyl | 0.5 H$_2$O; 138 |
| 25 (b) | —C(=O)—N(pyrrolidinyl) | 3,4-diCl-phenyl | 1 H$_2$O; 112–114 |
| 26 (b) | —NH—C(=O)—O—Et | 3,4-diF-phenyl | 0.5 H$_2$O; 130 |
| 27 (b) | —NH—C(=O)—NH—cyclopentyl | 3,4-diF-phenyl | 0.5 H$_2$O; 147 |

TABLE I-continued

| | | | Solvate; |
|---|---|---|---|
| EXAMPLES | Y | Ar$_1$ | M.p. ° C. or NMR |
| 28 (b) | —NH—C(=O)—N(Me)(Me) | 3,4-diF-phenyl | 0.5 H$_2$O<br>145 |
| 29 (b) | —NH—C(=O)—N(Et)(Et) | 3,4-diF-phenyl | 0.5 H$_2$O<br>140 |
| 30 (b) | —NH—C(=O)—N(pyrrolidinyl) | 3,4-diF-phenyl | 1 H$_2$O<br>144 |

(a) This compound is prepared according to the procedure described in EXAMPLE 17.

(b) This compound is prepared according to the procedure described in step D of EXAMPLE 15.

EXAMPLE 31

1-Benzyl-5-(3,4-difluorophenyl)-5-[2-(4-(N,N-dimethylcarbamoyl)-4-phenyl-1-piperidyl]ethyl]-2-piperidone hydrochloride hemihydrate A) 1-Benzyl-5-(3,4-difluorophenyl)-5-(2-hydroxy-ethyl)-2-piperidone.

2.35 g of potassium tert-butylate are added at RT to a solution of 6.78 g of the compound obtained in PREPARATION 2.5 in 50 ml of THF, and the mixture is left stirring for 5 minutes at RT. A solution of 3.59 g of benzylbromide in 10 ml of THF is then added dropwise, and the mixture is left stirring for 1 hour at RT and heated to reflux for 30 minutes. It is concentrated under vacuum, the residue is extracted with ether, the organic phase is washed with a pH 4 buffer solution, twice with water and twice with saturated NaCl solution and dried over MgSO$_4$ and the solvent is evaporated off under vacuum. The oil obtained (8.5 g) is dissolved in MeOH, a stream of HCl gas is bubbled through until the pH=1 and the mixture is concentrated under vacuum. 4.8 g of the expected product are obtained after crystallization in AcOEt, m.p.=153–154° C.

B) 1-Benzyl-5-(3,4-difluorophenyl)-5-[2-(methane-sulphonyloxy)ethyl]-2-piperidone.

A solution of 1 g of the compound obtained in the preceding step and 0.35 g of triethylamine in 100 ml of DCM is cooled to 0–5° C., a solution of 0.36 g of methanesulphonyl chloride in 10 ml of DCM is added dropwise and the mixture is concentrated under vacuum. The residue is taken up in water, the product is extracted with AcOEt, the organic phase is washed with water, with 5% NaHCO$_3$ solution, with water and with saturated NaCl solution and dried over MgSO$_4$ and the solvent is evaporated off under vacuum. 1.2 g of the expected product are obtained.

C) 1-Benzyl-5-(3,4-difluorophenyl)-5-[2-[4-(N,N-dimethylcarbamoyl]-4-phenyl-1-piperidyl]ethyl]-2-piperidone hydrochloride hemihydrate.

A mixture of 1.2 g of the compound obtained in the preceding step, 0.8 g of the compound obtained in PREPARATION 1.23 and 1.37 g of K$_2$CO$_3$ in 10 ml of a DMF/acetonitrile (50:50; v/v) mixture is heated to 100° C. for 3 hours. The reaction mixture is concentrated under vacuum, the residue is taken up in water, the product is extracted with AcOEt, the organic phase is washed with water and with saturated NaCl solution and dried over MgSO$_4$ and the solvent is evaporated off under vacuum. The residue is chromatographed on silica, eluting with DCM and then with a DCM/MeOH (96:4; v/v) mixture. The product obtained is dissolved in AcOEt, a stream of HCl gas is bubbled through until the pH=1, ether is then added and the mixture is concentrated under vacuum. 0.65 g of the expected product is obtained after solidification in ether, m.p.=154° C.

By working according to the procedure described in step C of EXAMPLE 31, starting from the compound obtained in step B of EXAMPLE 31 and the piperidines described in the preparations, the compounds according to the invention collated in TABLE II below are prepared.

TABLE II

[Structure: phenyl-piperidine(Y)-N-CH₂-CH₂-C(Ar₁)(CH₂CH₂)C(=O)N-CH₂-phenyl·HCl (Ib)]

| EXAMPLES | Y | Ar₁ | Solvate; M.p. ° C. or NMR |
|---|---|---|---|
| 32 | —C(=O)—N(pyrrolidine) | 3,4-difluorophenyl | 1 H₂O<br>160 |
| 33 | —NH—C(=O)—N(Me)₂ | 3,4-difluorophenyl | 0.5 H₂O<br>162 |
| 34 | —NH—C(=O)—N(pyrrolidine) | 3,4-difluorophenyl | 138 |

EXAMPLE 35

3-(3,4-Dichlorophenyl)-3-[2-[4-(2-hydroxyethyl)-4-phenyl-1-piperidyl]ethyl]-1-[2-(3-isopropoxyphenyl]-acetyl]piperidine hydrochloride monohydrate A) 3-(3,4-Dichlorophenyl)-1-[2-(3-isopropoxyphenyl)-acetyl]-3-[2-(tetrahydro-2-pyranyloxy)ethyl]-piperidine.

5.9 g of 3-isopropoxyphenylacetic acid and 21.6 g of BOP are added to a solution of 17.5 g of the compound obtained in PREPARATION 2.6 in 100 ml of DCM. The reaction mixture is left stirring for 1 hour at RT and concentrated under vacuum. The residue is taken up in AcOEt, the organic phase is washed with water, with 10% NaOH solution, with water, with a pH 2 buffer solution and with saturated sodium chloride solution and dried over sodium sulphate and the solvent is evaporated off under vacuum. The residue is chromatographed on silica, eluting with DCM and then with a DCM/AcOEt mixture gradient from (99:1; v/v) to (75:25; v/v). 21.5 g of the expected product are obtained, which is used in the next step without further treatment.

B) 3-(3,4-Dichlorophenyl)-3-(2-hydroxyethyl)-1-[2-(3-isopropoxyphenyl)acetyl]piperidine.

A mixture of 21.5 g of the compound obtained in the preceding step, 0.2 g of Amberlyst® 15 and 75 ml of MeOH is heated to reflux for 4 hours. The reaction mixture is filtered through Celite® and the filtrate is evaporated under vacuum. 18.2 g of the expected product are obtained, which is used in the next step without further treatment.

C) 3-(3,4-Dichiorophenyl)-1-[2-(3-isopropoxyphenyl)-acetyl]-3-[2-(methanesulphonyloxy)ethyl]-piperidine.

4.4 g of triethylamine are added to a solution, cooled to 0° C., of 18.2 g of the compound obtained in the preceding step in 75 ml of DCM, and a solution of 4.4 g of methanesulphonyl chloride in 20 ml of DCM is then added dropwise. The reaction mixture is left stirring for 1 hour and concentrated under vacuum. The residue is taken up in ether, the mixture is washed with water and dried over sodium sulphate and the solvent is evaporated off under vacuum. 20 g of the expected product are obtained in the form of an oil.

Proton NMR spectrum at 200 MHz in DMSO-d₆.

δ:

0.8 to 2.4 ppm: uc: 12 H
3.1 ppm: s: 3 H
3.1 to 4.8 ppm: uc: 9 H
6.5 to 7.9 ppm: u: 7 H.

D) 3-(3,4-Dichlorophenyl)-3-[2-[4-(2-hydroxyethyl)-4-phenyl-1-piperidyl]ethyl]-1-[2-(3-isopropoxyphenyl)acetyl]piperidine hydrochloride monohydrate.

A mixture of 2.4 g of the compound obtained in the preceding step and 3.2 g of the compound obtained in PREPARATION 1.24 in 4 ml of DMF is heated to 80° C. for 3 hours. After cooling, the reaction mixture is poured into water, the mixture is extracted with AcOEt, the organic phase is washed with water and dried over Na₂SO₄ and the solvent is evaporated off under vacuum. The product obtained is dissolved in DCM, ethereal hydrogen chloride is added until the pH=1 and the precipitate formed is drained. 1 g of the expected product is obtained.

Proton NMR spectrum at 200 MHz in DMSO-d₆.

δ:

0.7 to 4.8 ppm: uc: 34 H
6.4 to 7.8 ppm: uc: 12 H
10.3 ppm: s: 1 H.

EXAMPLE 36

3-[2-[4-(2-Acetoxyethyl)-4-phenyl-1-piperidyl]-
ethyl]-3-(3,4-dichlorophenyl)-1-[2-(3-isopropoxy-
phenyl)acetyl]piperidine hydrochloride
monohydrate A mixture of 0.7 g of the compound obtained in EXAMPLE 35 and 2 ml of acetyl chloride in 15 ml of chloroform is heated to reflux for 15 minutes. The mixture is concentrated under vacuum, the residue is extracted with AcOEt, the organic phase is washed with water, with 5% $NaHCO_3$ solution and with water and dried over $Na_2SO_4$ and the solvent is evaporated off under vacuum. The product obtained is dissolved in DCM, ethereal hydrogen chloride is added until the pH=1 and the precipitate formed is drained. 0.4 g of the expected product is obtained.

Proton NMR spectrum at 200 MHz in DMSO-$d_6$.
δ:
0.8 to 4.8 ppm: uc: 36 H
6.4 to 7.8 ppm: uc: 12 H
10.2 ppm: s: 1 H.

EXAMPLE 37

N-[4-[4-(2-Amino-4-thiazolyl)-4-phenyl-1-
piperidyl]-2-(3,4-dichlorophenyl)butyl]-N-
methylbenzamide dihydrochloride sesquihydrate,
(−) isomer A) N-[2-(3,4-Dichlorophenyl)-4-(methanesulphonyloxy)butyl]-N-methylbenzamide, (−) isomer.

The preparation of this compound is described in Patent Application EP-A-0474561.

B) N-[4-[4-(2-Amino-4-thiazolyl)-4-phenyl-1-piperidyl]-2-(3,4-dichlorophenyl)butyl]-N-methylbenzamide dihydrochloride sesquihydrate, (−) isomer.

A mixture of 1.1 g of the compound obtained in the preceding step, 0.74 g of the compound obtained in PREPARATION 1.25 in free base form and 0.65 g of $K_2CO_3$ in 10 ml of a DMF/acetonitrile (50:50; v/v) mixture is heated to 100° C. for 3 hours. After cooling at RT, the reaction mixture is poured into water, the product is extracted with AcOEt, the organic phase is washed twice with water and with saturated NaCl solution and dried over $MgSO_4$ and the solvent is evaporated off under vacuum. The residue is chromatographed on silica H, eluting with DCM and then with a DCM/MeOH (96:4; v/v) mixture. The product obtained is dissolved in acetone, ethereal hydrogen chloride is added until the pH=1 and the precipitate form is drained. 0.79 g of the expected product is obtained, m.p.=172–174° C.

EXAMPLE 38

N-[2-(3,4-Dichlorophenyl)-4-[4-(2-diethylamino)-4-
thiazolyl]-4-phenyl-1-piperidyl]butyl]-N-
methylbenzamide dihydrochloride, (−) isomer This compound is prepared according to the procedure described in EXAMPLE 5, from 1.72 g of the compound obtained in step B of EXAMPLE 1, 2 g of the compound obtained in PREPARATION 1.26, 1.74 g of $K_2CO_3$ and 16 ml of a DMF/acetonitrile (50:50; v/v) mixture. 1.6 g of the expected product are obtained, m.p.=128–129° C.

$[\alpha]_D^{20}$ = −14.6° (c = 0.5; MeOH).

EXAMPLE 39

5-[2-[4-(2-Amino-4-thiazolyl)-4-phenyl-1-piperidyl]
ethyl]-1-benzyl-5-(3,4-difluorophenyl)-2-piperidone
dihydrochloride monohydrate This compound is prepared according to the procedure described in step C of EXAMPLE 31, from 1.5 g of the compound obtained in step B of EXAMPLE 31, 1.1 g of the compound obtained in PREPARATION 1.25 in free base form, 1 g of $K_2CO_3$ and 10 ml of a DMF/acetonitrile (50:50; v/v) mixture. 0.96 g of the expected product is obtained after solidification in acetone, m.p.=208° C.

EXAMPLE 40

1-Benzyl-5-(3,4-difluorophenyl)-5-[2-[4-[2-
(dimethylamino)-4-thiazolyl]-4-phenyl-1-piperidyl]-
ethyl]-2-piperidone dihydrochloride hemihydrate This compound is prepared according to the procedure described in step C of EXAMPLE 31, from 1 g of the compound obtained in step B of EXAMPLE 31, 1.3 g of the compound obtained in PREPARATION 1.27 and 1.4 g of $K_2CO_3$ in 20 ml of a DMF/acetonitrile (50:50; v/v) mixture. 0.9 g of the expected product is obtained after crystallization in AcOEt, m.p.=140–142° C.

EXAMPLE 41

N-[4-[4-(2-Amino-1,3,4-oxadiazol-5-yl)-4-phenyl-1-
piperidyl]-2-(3,4-dichlorophenyl)butyl]-N-
methylbenzamide dihydrochloride dihydrate, (−)
isomer This compound is prepared according to the procedure described in EXAMPLE 5, from 1.72 g of the compound obtained in step B of EXAMPLE 1, 1.75 g of the compound obtained in PREPARATION 1.28, 1.74 g of $K_2CO_3$ and 16 ml of a DMF/acetonitrile (50:50; v/v) mixture. 0.95 g of the expected product is obtained, m.p.=158° C.

$[\alpha]_D^{20}$ = −26.8° (c = 0.5; MeOH).

EXAMPLE 42

N-[2-(3,4-Dichlorophenyl)-4-[4-(3,3-dimethyl-
carbazoyl)-4-phenyl-1-piperidyl]butyl]-N-
methylbenzamide hydrochloride dihydrate, (−)
isomer This compound is prepared according to the procedure described in EXAMPLE 5, from 1.72 g of the compound obtained in step B of EXAMPLE 1, 1.76 g of the compound obtained in PREPARATION 1.29, 1.74 g of $K_2CO_3$ and 16 ml of a DMF/acetonitrile (50:50; v/v) mixture. 1.35 g of the expected product are obtained, m.p.=153° C.

$[\alpha]_D^{20}$ = -26.0° (c = 0.5; MeOH).

EXAMPLE 43

N-[2-(3,4-Dichlorophenyl)-4-[4-(3-ethyl-1-methylureido)-4-phenyl-1-piperidyl]butyl]-N-methylbenzamide hydrochloride monohydrate, (−) isomer This compound is prepared according to the procedure described in EXAMPLE 5, from 1.72 g of the compound obtained in step B of EXAMPLE 1, 1.82 g of the compound obtained in PREPARATION 1.30, 1.74 g of $K_2CO_3$ and 16 ml of a DMF/acetonitrile (50:50; v/v) mixture. 0.8 g of the expected product is obtained after crystallization in ether, m.p.=128–130° C.

$[\alpha]_D^{20}$ = -24.7° (c = 0.5; MeOH).

EXAMPLE 44

1-Benzyl-5-(3,4-difluorophenyl)-5-[2-[4-(methoxycarbonylamino)-4-phenyl-1-piperidyl]ethyl]-2-piperidone-hydrochloride monohydrate This compound is prepared according to the procedure described in step C of EXAMPLE 31, from 1.2 g of the compound obtained in step B of EXAMPLE 31, 1.38 g of the compound obtained in PREPARATION 1.5, 1.37 g of $K_2CO_3$ and 20 ml of a DMF/acetonitrile (50:50; v/v) mixture. 0.52 g of the expected product is obtained, m.p.=150° C.

EXAMPLE 45

1-Benzyl-5-[2-[4-(3-cyclopentylureido)-4-phenyl-1-piperidyl]ethyl]-5-(3,4-difluorophenyl)-2-piperidone hydrochloride monohydrate This compound is prepared according to the procedure described in step C of EXAMPLE 31, from 1 g of the compound obtained in step B of EXAMPLE 31, 1.3 g of the compound obtained in PREPARATION 1.9, 1.14 g of $K_2CO_3$ and 20 ml of a DMF/acetonitrile (50:50; v/v) mixture. 0.68 g of the expected product is obtained, m.p.=170° C.

EXAMPLE 46

N-[4-[4-(2-Furoylamino)-4-phenyl-1-piperidyl]-2-(3,4-dichlorophenyl)butyl]-N-methylbenzamide hydrochloride sesquihydrate, (−) isomer A) N-[4-(4-Amino-4-phenyl-1-piperidyl)-2-(3,4-dichlorophenyl)butyl]-N-methylbenzamide, (−) isomer.

This compound is prepared according to the procedure described in EXAMPLE 5, from 6.3 g of the compound obtained in step B of EXAMPLE 1, 7.89 g of the compound obtained in PREPARATION 1.31, 7.06 g of $K_2CO_3$ and 30 ml of a DMF/acetonitrile (50:50; v/v) mixture. The product is chromatographed on silica, eluting with a DCM/MeOH mixture from (95:5; v/v) to (85:15; v/v). 2.9 g of the expected product are obtained in the form of an oil.

B) N-[4-[4-(2-Furoylamino)-4-phenyl-1-piperidyl]-2-(3,4-dichlorophenyl)butyl]-N-methylbenzamide hydrochloride sesquihydrate, (−) isomer.

A solution of 1.14 g of the compound obtained in the preceding step and 0.45 g of triethylamine in 10 ml of DCM is cooled to 5° C., 0.29 g of 2-furoyl chloride is added and the mixture is left stirring while allowing the temperature to rise to RT. The mixture is concentrated under vacuum, the residue is extracted with DCM, the organic phase is washed with water, with 5% $NaHCO_3$ solution, with water and with saturated NaCl solution and dried over $MgSO_4$ and the solvent is evaporated off under vacuum. The residue is chromatographed on silica H, eluting with DCM and then with a DCM/MeOH (97:3; v/v) mixture. The product obtained is dissolved in AcOEt, a stream of HCl gas is bubbled through until the pH=1, ether is then added and the precipitate formed is drained. 0.91 g of the expected product is obtained, m.p.=161–163° C.

$[\alpha]_D^{20}$ = -22.6° (c = 0.5; MeOH).

EXAMPLE 47

N-[4-[4-Benzyl-4-(ethoxycarbonylamino)-1-piperidyl]-2-(3,4-dichlorophenyl)butyl]-N-methylbenzamide hydrochloride hemihydrate, (−) isomer This compound is prepared according to the procedure described in step C of Example 1, from 0.5 g of the compound obtained in step B of EXAMPLE 1, 0.5 g of the compound obtained in PREPARATION 1.32 and 0.54 g of $K_2CO_3$ in 5 ml of DMF. 0.33 g of the expected product is obtained, m.p.=134° C. (dec.).

$[\alpha]_D^{20}$ = -22.1° (c = 1; MeOH).

EXAMPLE 48

N-[4-[4-[N-(1-Pyrrolidinyl)carbamoyl]-4-phenyl-1-piperidyl]-2-(3,4-dichlorophenyl)butyl]-N-methylbenzamide dihydrochloride dihydrate, (−) isomer This compound is prepared according to the procedure described in EXAMPLE 5, from 1.58 g of the compound obtained in step B of EXAMPLE 1, 1.6 g of the compound obtained in PREPARATION 1.33, 1.28 g of $K_2CO_3$ and 10 ml of a DMF/acetonitrile (50:50; v/v) mixture. 0.99 g of the expected product is obtained, m.p.=150–152° C.

$[\alpha]_D^{20}$ = -5.75° (c = 0.5; MeOH).

EXAMPLE 49

N-[4-[4-(3-Acetylcarbazoyl)-4-phenyl-1-piperidyl]-2-(3,4-dichlorophenyl)butyl]-N-methylbenzamide hydrochloride 2.5 hydrate, (−) isomer This compound is prepared according to the procedure described in EXAMPLE 5, from 1.22 g of the compound obtained in step B of EXAMPLE 1, 1.15 g of the compound obtained in PREPARATION 1.34, 0.94 g of $K_2CO_3$ and 10 ml of a DMF/acetonitrile (50:50; v/v) mixture. 0.69 g of the expected product is obtained, m.p.=145–147° C.

$[\alpha]_D^{20} = -0.3°$ (c = 0.5; MeOH).

EXAMPLE 50

1-[2-(3-Chlorophenyl)acetyl]-3-(3,4-dichlorophenyl)-3-[2-[4-(N,N-dimethylcarbamoyl)-4-phenyl-1-piperidyl]ethyl]piperidine hydrochloride monohydrate, (–) isomer A) 1-[2-(3-Chlorophenyl)acetyl]-3-(3,4-dichlorophenyl)-3-(2-hydroxyethyl)piperidine, (–) isomer.

7 g of triethylamine and 16.9 g of BOP are added to a solution of 9.6 g of the compound obtained in PREPARATION 2.7 in 300 ml of DCM, the mixture is then cooled to 5° C., a solution of 5.9 g of 3-chlorophenylacetic acid in 30 ml of DCM is added dropwise and the mixture is left stirring for 3 hours while allowing the temperature to rise to RT. The mixture is concentrated under vacuum, the residue is extracted with ether, the organic phase is washed with water, with 2N HCl solution, with saturated NaCl solution, with 10% NaOH solution and with saturated NaCl solution and dried over $Na_2SO_4$ and the solvent is evaporated off under vacuum. 15.14 g of the expected product are obtained.

$[\alpha]_D^{20} = -23.8°$ (c = 0.5; MeOH).

B) 1-[2-(3-Chlorophenyl)acetyl]-3-(3,4-dichlorophenyl)-3-[2-(methanesulphonyloxy)ethyl]-piperidine.

A solution of 13.44 g of the compound obtained in the preceding step and 4.8 ml of triethylamine in 80 ml of DCM is cooled to 0° C., a solution of 2.6 ml of methanesulphonyl chloride in 80 ml of DCM is added dropwise and the mixture is left stirring while the temperature is allowed to rise to RT. The mixture is concentrated under vacuum, the residue is extracted with AcOEt, the organic phase is washed with water, with 2N HCl solution, with water and with saturated NaCl solution and dried over $Na_2SO_4$ and the solvent is evaporated off under vacuum. 16.39 g of the expected product are obtained.

C) 1-[2-(3-Chlorophenyl)acetyl]-3-(3,4-dichlorophenyl)-3-[2-[4-(N,N-dimethylcarbamoyl)-4-phenyl-1-piperidyl]ethyl]piperidine hydrochloride monohydrate, (–) isomer A mixture of 1.5 g of the compound obtained in the preceding step, 0.78 g of the compound obtained in PREPARATION 1.23 and 0.82 g of $K_2CO_3$ in 10 ml of a DMF/acetonitrile (50:50; v/v) mixture is heated to 100° C. for 4 hours. After cooling, the reaction mixture is poured into water, the product is extracted with AcOEt, the organic phase is washed with water and with saturated NaCl solution and dried over $Na_2SO_4$ and the solvent is evaporated off under vacuum. The residue is chromatographed on silica H, eluting with a DCM/MeOH mixture from (99:1; v/v) to (96:4; v/v). The product obtained is dissolved in AcOEt, ethereal hydrogen chloride is added until the pH=1 and the precipitate formed is drained. 1.15 g of the expected product are obtained after cyrstallization in ether, m.p.=145–150° C.

$[\alpha]_D^{20} = -11.2°$ (c = 0.5; MeOH).

EXAMPLE 51

1-[2-(3-Chlorophenyl)acetyl]-3-(3,4-dichlorophenyl)-3-[2-[4-(1-pyrrolidinylcarbonyl)-4-phenyl-1-piperidyl]ethyl]piperidine hydrochloride monohydrate, (–) isomer This compound is prepared according to the procedure described in step C of EXAMPLE 50, from 1.5 g of the compound obtained in step B of EXAMPLE 50, 0.92 g of the compound obtained in PREPARATION 1.21 and 0.82 g of $K_2CO_3$ in 14 ml of a DMF/acetonitrile (50:50; v/v) mixture. 1.05 g of the expected product are obtained, m.p.=150–155° C.

$[\alpha]_D^{20} = -12.0°$ (c = 0.5; MeOH).

We claim:
1. A compound of formula:

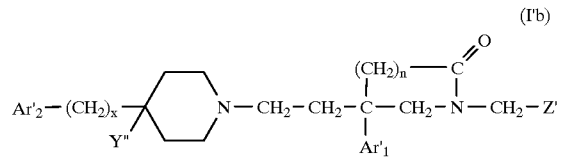

(I'b)

in which:

x is zero or one;

n is one, two or three;

Y" represents a group chosen from:
- $Y_3$) —O—$CH_2CH_2$—$OR_4$;
- $Y_6$) —$(CH_2)_q$—OCONH—$(C_1$–$C_7)$alkyl;
- $Y_9$) —$NR_{11}COR_{12}$;
- $Y_{11}$) —$(CH_2)_q$—$NR_{13}COOR_{15}$;
- $Y_{12}$) —$(CH_2)_q$—$NR_{13}SO_2R_{16}$;
- $Y_{13}$) —$(CH_2)_q$—$NR_{13}CONR_{17}R_{18}$;
- $Y_{14}$) —$CONR_{19}R_{20}$;
- $Y_{15}$) —$CH_2$—$COOR_{21}$;
- $Y_{17}$)

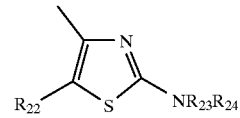

$Y_{18}$)

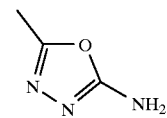

$Y_{19}$) —CO—$NR_{25}$—$NR_{26}R_{27}$;

in which groups:

q is zero, one or two $R_4$ represents a hydrogen; a $(C_1$–$C_7)$alkyl; a formyl; a $(C_1$–$C_7)$alkylcarbonyl;

$R_{11}$ represents a hydrogen or a $(C_1-C_7)$alkyl;

$R_12$ represents a $(C_3-C_7)$cycloalkyl unsubstituted or substituted with one or more methyls; a phenyl; a benzyl; a vinyl; a pyridyl; a furyl; a thienyl; a pyrrolyl; an imidazolyl;

or alternatively $R_{11}$ and $R_{12}$ together represent a group $-(CH_2)_m-$ in which m is three or four;

$R_{13}$ represents a hydrogen or a $(C_1-C_7)$alkyl;

$R_{15}$ represents a $(C_1-C_7)$ alkyl or a phenyl;

$R_{16}$ represents a $(C_1-C_7)$alkyl; an amino, free or substituted with one or two $(C_1-C_7)$alkyls; a phenyl unsubstituted or substituted one or more times with a substituent chosen from: a halogen atom, a $(C_1-C_7)$alkyl, a trifluoromethyl, a hydroxyl, a $(C_1-C_7)$alkoxy, a carboxyl, a $(C_1-C_7)$alkoxycarbonyl, a $(C_1-C_7)$ alkylcarbonyloxy, a cyano, a nitro, an amino, free or substituted with one or two $(C_1-C_7)$alkyls, the said substituents being identical or different;

$R_{17}$ and $R_{18}$ each independently represent a hydrogen or a $(C_1-C_7)$alkyl; $R_{18}$ can, in addition, represent a $(C_3-C_7)$ cycloalkyl, a $(C_3-C_7)$ cycloalkylmethyl, a hydroxyl, a $(C_1-C_4)$alkoxy, a benzyl or a phenyl;

or alternatively $R_{17}$ and $R_{18}$, together with the nitrogen atom to which they are linked, constitute a heterocycle chosen from azetidine, pyrrolidine, piperidine, morpholine, thiomorpholine, perhydroazepine and piperazine unsubstituted or substituted at position 4 with a $(C_1-C_4)$alkyl;

$R_{19}$ represents a hydrogen or a $(C_1-C_7)$alkyl;

$R_{20}$ represents a $(C_3-C_7)$cycloalkyl; a $(C_3-C_7)$cycloalkylmethyl; a hydroxyl; a $(C_1-C_4)$alkoxy; a benzyl; a phenyl; $R_{20}$ can, in addition, represent a hydrogen or a $(C_1-C_7)$alkyl when n is two or three;

or alternatively $R_{19}$ and $R_{20}$, together with the nitrogen atom to which they are linked, constitute a heterocycle chosen from azetidine, thiomorpholine, perhydroazepine and piperazine; $R_{19}$ and $R_{20}$, together with the nitrogen atom to which they are linked, can, in addition, constitute a heterocycle chosen from pyrrolidine, piperidine, morpholine and piperazine substituted at position 4 with a $(C_1-C_4)$alkyl when n is three or three;

$R_{21}$ represents a hydrogen or a $(C_1-C_7)$alkyl;

$R_{22}$ represents a hydrogen or a $(C_1-C_7)$alkyl;

$R_{23}$ and $R_{24}$ each independently represent a hydrogen or a $(C_1-C_7)$alkyl; $R_{24}$ can, in addition, represent a formyl or a $(C_1-C_7)$alkylcarbonyl;

$R_{25}$ represents a hydrogen or a $(C_1-C_7)$alkyl;

$R_{26}$ and $R_{27}$ each independently represent a hydrogen or a $(C_1-C_7)$alkyl;

$Ar'_1$ represents a phenyl unsubstituted or substituted one or more times with a substituent chosen from: a halogen atom, a hydroxyl, a $(C_1-C_4)$alkoxy, a $(C_1-C_4)$alkyl, a trifluoromethyl, a methylenedioxy, the said substituents being identical or different;

$Ar'_2$ represents a phenyl unsubstituted or substituted one or more times with a substituent chosen from: a halogen atom, a hydroxyl, a $(C_1-C_4)$alkoxy, a $(C_1-C_4)$alkyl, a trifluoromethyl, a methylenedioxy, the said substituents being identical or different;

Z' represents:
a phenyl unsubstituted or substituted one or more times with a substituent chosen from: a halogen atom; a trifluoromethyl; a cyano; a hydroxyl; a nitro; a phenyl unsubstituted or substituted one or more times with a halogen, a trifluoromethyl, a $(C_1-C_4)$ alkyl, a hydroxyl, a $(C_1-C_4)$alkoxy, the said substituents being identical or different; an amino unsubstituted or substituted once or twice with a $(C_1-C_4)$ alkyl; a benzylamino; a carboxyl; a $(C_1-C_{10})$alkyl; a $(C_3-C_8)$ cycloalkyl unsubstituted or substituted one or more times with a methyl; a $(C_1-C_{10})$alkoxy; a $(C_3-C_8)$cycloalkyloxy unsubstituted or substituted one or more times with a methyl; a mercapto; a $(C_1-C_{10})$alkylthio; a formyloxy; a $(C_1-C_6)$ alkylcarbonyloxy; a formylamino; a $(C_1-C_6)$ alkylcarbonylamino; a benzoylamino; a $(C_1-C_4)$ alkoxycarbonyl; a $(C_3-C_7)$cycloalkyloxycarbonyl; a carbamoyl unsubstituted or substituted once or twice with a $(C_1-C_4)$alkyl; a ureido unsubstituted or substituted once or twice at position 3 with a $(C_1-C_4)$ alkyl or a $(C_3-C_7)$cycloalkyl; a (1-pyrrolidinyl) carbonylamino, the said substituents being identical or different;
a naphthyl unsubstituted or substituted one or more times with a halogen, a trifluoromethyl, a $(C_1-C_4)$ alkyl, a hydroxyl, a $(C_1-C_4)$alkoxy;
a pyridyl; a thienyl; an indolyl; a quinolyl; a benzothienyl; an imidazolyl;

and its salts with inorganic or organic acids.

2. A compound of formula:

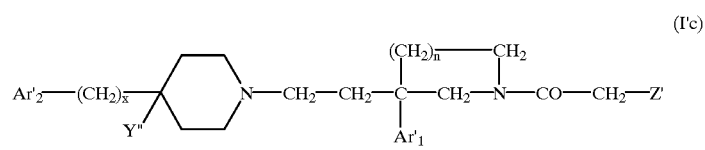

(I'c)

in which:

x is zero or one;

n is one, two or three;

Y" represents a group chosen from:
$Y_3$) $-O-CH_2CH_2-OR_4$;
$Y_6$) $-(CH_2)_q-OCONH-(C_1-C_7)$alkyl;
$Y_9$) $-NR_{11}COR_{12}$;
$Y_{11}$) $-(CH_2)_q-NR_{13}COOR_{15}$;
$Y_{12}$) $-(CH_2)_q-NR_{13}SO_2R_{16}$;
$Y_{13}$) $-(CH_2)_q-NR_{13}CONR_{17}R_{18}$;
$Y_{14}$) $-CONR_{19}R_{20}$;
$Y_{15}$) $-CH_2-COOR_{21}$;

$Y_{17}$)

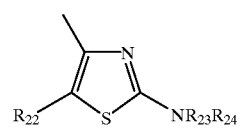

$Y_{18}$)

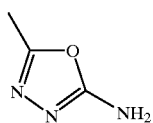

$Y_{19}$) —CO—NR$_{25}$—NR$_{26}$R$_{27}$;

in which groups:

q is zero, one or two;

R$_4$ represents a hydrogen; a (C$_1$–C$_7$)alkyl; a formyl; a (C$_1$–C$_7$)alkylcarbonyl;

R$_{11}$ represents a hydrogen or a (C$_1$–C$_7$)alkyl;

R$_{12}$ represents a (C$_3$–C$_7$)cycloalkyl unsubstituted or substituted with one or more methyls; a phenyl; a benzyl; a vinyl; a pyridyl; a furyl; a thienyl; a pyrrolyl; an imidazolyl;

or alternatively R$_{11}$ and R$_{12}$ together represent a group —(CH$_2$)$_m$— in which m is three or four;

R$_{13}$ represents a hydrogen or a (C$_1$–C$_7$)alkyl;

R$_{15}$ represents a (C$_1$–C$_7$)alkyl or a phenyl;

R$_{16}$ represents a (C$_1$–C$_7$)alkyl; an amino, free or substituted with one or two (C$_1$–C$_7$)alkyls; a phenyl unsubstituted or substituted one or more times with a substituent chosen from: a halogen atom, a (C$_1$–C$_7$)alkyl, a trifluoromethyl, a hydroxyl, a (C$_1$–C$_7$)alkoxy, a carboxyl, a (C$_1$–C$_7$)alkoxycarbonyl, a (C$_1$–C$_7$) alkylcarbonyloxy, a cyano, a nitro, an amino, free or substituted with one or two (C$_1$–C$_7$)alkyls, the said substituents being identical or different;

R$_{17}$ and R$_{18}$ each independently represent a hydrogen or a (C$_1$–C$_7$)alkyl; R$_{18}$ can, in addition, represent a (C$_3$–C$_7$)cycloalkyl, a (C$_3$–C$_7$)cycloalkylmethyl, a hydroxyl, a (C$_1$–C$_4$)alkoxy, a benzyl or a phenyl;

or alternatively R$_{17}$ and R$_{18}$, together with the nitrogen atom to which they are linked, constitute a heterocycle chosen from azetidine, pyrrolidine, piperidine, morpholine, thiomorpholine, perhydroazepine and piperazine unsubstituted or substituted at position 4 with a (C$_1$–C$_4$)alkyl;

R$_{19}$ represents a hydrogen or a (C$_1$–C$_7$)alkyl;

R$_{20}$ represents a (C$_3$–C$_7$)cycloalkyl; a (C$_3$–C$_7$)cycloalkylmethyl; a hydroxyl; a (C$_1$–C$_4$)alkoxy; a benzyl; a phenyl; R$_{20}$ can, in addition, represent a hydrogen or a (C$_1$–C$_7$)alkyl when n is two or three;

or alternatively R$_{19}$ and R$_{20}$, together with the nitrogen atom to which they are linked, constitute a heterocycle chosen from azetidine, thiomorpholine, perhydroazepine and piperazine; R$_{19}$ and R$_{20}$, together with the nitrogen atom to which they are linked, can, in addition, constitute a heterocycle chosen from pyrrolidine, piperidine, morpholine and piperazine substituted at position 4 with a (C$_1$–C$_4$)alkyl when n is two or three;

R$_{21}$ represents a hydrogen or a (C$_1$–C$_7$)alkyl;

R$_{22}$ represents a hydrogen or a (C$_1$–C$_7$)alkyl;

R$_{23}$ and R$_{24}$ each independently represent a hydrogen or a (C$_1$–C$_7$)alkyl; R$_{24}$ can, in addition, represent a formyl or a (C$_1$–C$_7$)alkylcarbonyl;

R$_{25}$ represents a hydrogen or a (C$_1$–C$_7$)alkyl;

R$_{26}$ and R$_{27}$ each independently represent a hydrogen or a (C$_1$–C$_7$)alkyl;

Ar'$_2$ represents a phenyl unsubstituted or substituted one or more times with a substituent chosen from: a halogen atom, a hydroxyl, a (C$_1$–C$_4$)alkoxy, a (C$_1$–C$_4$)alkyl, a trifluoromethyl, a methylenedioxy, the said substituents being identical or different;

Ar'$_2$ represents a phenyl unsubstituted or substituted one or more times with a substituent chosen from: a halogen atom, a hydroxyl, a (C$_1$–C$_4$)alkoxy, a (C$_1$–C$_4$)alkyl, a trifluoromethyl, a methylenedioxy, the said substituents being identical or different;

Z' is:

a phenyl unsubstituted or substituted one or more times with a substituent chosen from: a halogen atom; a trifluoromethyl; a cyano; a hydroxyl; a nitro; a phenyl unsubstituted or substituted one or more times with a halogen, a trifluoromethyl, a (C$_1$–C$_4$) alkyl, a hydroxyl, a (C$_1$–C$_4$)alkoxy, the said substituents being identical or different; an amino unsubstituted or substituted once or twice with a (C$_1$–C$_4$) alkyl; a benzylamino; a carboxyl; a (C$_1$–C$_{10}$)alkyl; a (C$_3$–C$_8$) cycloalkyl unsubstituted or substituted one or more times with a methyl; a (C$_1$–C$_{10}$)alkoxy; a (C$_3$–C$_8$)cycloalkyloxy unsubstituted or substituted one or more times with a methyl; a mercapto; a (C$_1$–C$_{10}$)alkylthio; a formyloxy; a (C$_1$–C$_6$) alkylcarbonyloxy; formylamino; a (C$_1$–C$_6$) alkylcarbonylamino; a benzoylamino; a (C$_1$–C$_4$) alkoxycarbonyl; a (C$_3$–C$_7$)cycloalkyloxycarbonyl; a carbamoyl unsubstituted or substituted once or twice with a (C$_1$–C$_4$)alkyl; a ureido unsubstituted or substituted once or twice at position 3 with a (C$_1$–C$_4$) alkyl or a (C$_3$–C$_7$)cycloalkyl; a (1-pyrrolidinyl) carbonylamino, the said substituents being identical or different;

a naphthyl unsubstituted or substituted one or more times with a halogen, a trifluoromethyl, a (C$_1$–C$_4$) alkyl, a hydroxyl, a (C$_1$–C$_4$)alkoxy;

a pyridyl; a thienyl; an indolyl; a quinolyl; a benzothienyl; an imidazolyl;

and its salts with inorganic or organic acids.

3. An optically pure compound according to claim 1, of formula:

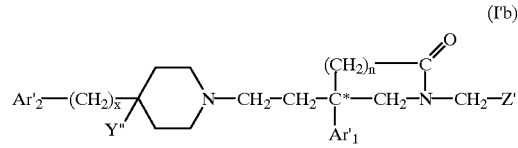

(I'b)

in which:

"*" means that the carbon atom thus labelled has the particular (+) or (–) absolute configuration;

n, x, Y", Ar'$_1$, Ar'$_2$, and Z' are as defined for a compound of formula (I) in claim 1;

and its salts with inorganic or organic acids.

4. An optically pure compound according to claim 2, of formula:

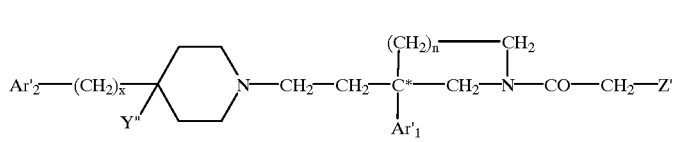

(I'c)

in which:

"*" means that the carbon atom thus labelled has the particular (+) or (−) absolute configuration;

x, n, Y", Ar'$_1$, Ar'$_2$, and Z' are as defined for a compound of formula (I) in claim 2;

and its salts with inorganic or organic acids.

5. A compound according to claim 1, of formula:

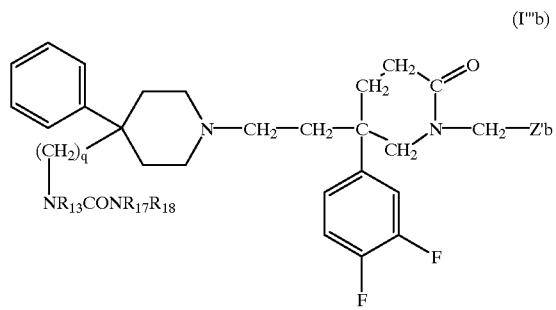

(I'''b)

6. A compound according to claim 5, of formula (I'''b), in optically pure form, and its salts with inorganic or organic acids.

7. A compound according to claim 1, of formula:

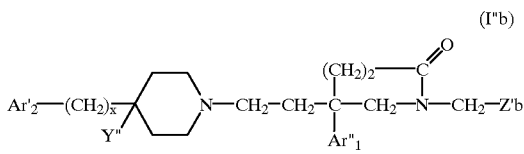

(I"b)

in which:

x and Y" are as defined for a compound of formula (I'b) of claim 7;

Ar"$_1$ represents a 3,4-dichlorophenyl or a 3,4-difluorophenyl;

Ar"$_2$ represents an unsubstituted phenyl;

Z'b represents an unsubstituted phenyl, a 3,5-bis(trifluoromethyl)phenyl, a 3,5-dimethylphenyl or a 2,4-bis(trifluoromethyl)phenyl;

and their salts with inorganic or organic acids.

8. A compound according to claim 7 in optically pure form and its salts with organic or inorganic acids.

9. A compound according to claim 2, of formula:

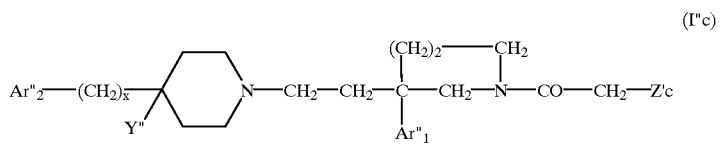

(I"c)

in which:

Z'b represents an unsubstituted phenyl, a 3,5-bis(trifluoromethyl)phenyl, a 3,5-dimethylphenyl or a 2,4-bis(trifluoromethyl)phenyl;

q is is zero, one or two;

R$_{13}$ represents a hydrogen or a (C$_1$–C$_7$)alkyl;

R$_{17}$ and R$_{18}$ each independently represent a hydrogen or a (C$_1$–C$_7$)alkyl; R$_{18}$ can, in addition, represent a (C$_3$–C$_7$)cycloalkyl, a (C$_3$–C$_7$)cycloalkylmethyl, a hydroxyl, a (C$_1$–C$_4$)alkoxy, a benzyl or a phenyl;

or alternatively R$_{17}$ and R$_{18}$, together with the nitrogen atom to which they are linked, constitute a heterocycle chosen from azetidine, pyrrolidine, piperidine, morpholine, thiomorpholine, perhydroazepine and piperazine unsubstituted or substituted at position 4 with a (C$_1$–C$_4$)alkyl;

and its salts with inorganic or organic acids.

x and Y" are as defined for a compound of formula (I'c) in claim 2;

Ar"$_1$ and Ar"$_2$ are as defined for a compound of formula (I"b) in claim 7;

Z'c represents a phenyl substituted at position 3 with a halogen or a (C$_1$–C$_{10}$)alkoxy group;

and their salts with inorganic or organic acids.

10. A compound according to claim 9 in optically pure form and its salts with organic or inorganic acids.

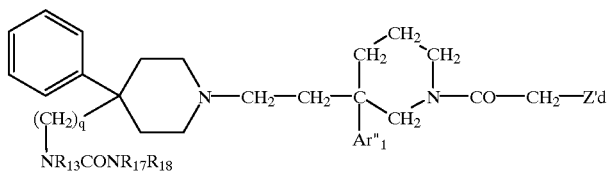

(I'''c)

11. A compound having the formula:
in which:
q is zero, one or two;
Ar"$_1$ represents a 3,4-dichlorophenyl or a 3,4-difluorophenyl;
Z'd represents a phenyl substituted one or two times with a substituent chosen from : a halogen atom, a trifluoromethyl ; a ($C_1$–$C_{10}$)alkyl ; a ($C_1$–$C_{10}$)alkoxy, the said susbtituents being identical or different;
$R_{13}$, $R_{17}$ and $R_{18}$ are as defined for a compound of formula (I'''b) in claim 5;
and their salts with inorganic or organic acids.

12. A compound according to claim 11 in optically pure form and its salts with organic or inorganic acids.

13. Pharmaceutical composition containing as active principle a compound according to claim 1 or one of its pharmaceutically acceptable salts in combination with a pharmaceutically acceptable carrier, excipient or diluent.

14. Pharmaceutical composition containing as active principle a compound according to claim 2 or one of its pharmaceutically acceptable salts in combination with a pharmaceutically acceptable carrier, excipient or diluent.

15. Pharmaceutical composition according to claim 13 or 14, in the form of a dosage unit in which the active principle is mixed with at least one pharmaceutical excipient.

16. Pharmaceutical composition according to claim 15, containing 0.5 to 1000 mg of active principle.

17. Pharmaceutical composition according to claim 16 containing 2.5 to 250 mg of active principle.

18. A pharmaceutical composition which comprises the compound of claim 5 or 6 in combination with a pharmaceutically acceptable carrier, excipient or diluent.

19. A pharmaceutical composition which comprises the compound of claim 7 or 8 in combination with a pharmaceutically acceptable carrier, excipient or diluent.

20. A pharmaceutical composition which comprises the compound of claim 9 or 10 in combination with a pharmaceutically acceptable carrier, excipient or diluent.

21. A pharmaceutical composition which comprises the compound of claim 11 or 12 in combination with a pharmaceutically acceptable carrier, excipient or diluent.

* * * * *